United States Patent
Wood et al.

(10) Patent No.: US 10,149,907 B2
(45) Date of Patent: Dec. 11, 2018

(54) COMBINATIONS OF A PHOTOSENSITIZER WITH A HYDROGEN SULFIDE DONOR, THIOREDOXIN INHIBITOR OR NITROXIDE FOR USE IN PHOTODYNAMIC THERAPY

(71) Applicant: UNIVERSITY OF EXETER, Exeter (GB)

(72) Inventors: Mark Elliott Wood, Exeter (GB); Paul Graham Winyard, Exeter (GB); Daniel Colin Jeremy Ferguson, Bristol (GB); Matthew Whiteman, Bradninch (GB); Alison Curnow, Cornwall (GB); Alexis Perry, Exeter (GB)

(73) Assignee: University of Exeter, Exeter (GB)

(*) Notice: Subject to any disclaimer, the term of this patent is extended or adjusted under 35 U.S.C. 154(b) by 0 days.

(21) Appl. No.: 15/890,576

(22) Filed: Feb. 7, 2018

(65) Prior Publication Data
US 2018/0161430 A1   Jun. 14, 2018

Related U.S. Application Data

(63) Continuation of application No. 15/315,699, filed as application No. PCT/GB2015/051608 on Jun. 2, 2015, now Pat. No. 9,919,049.

(30) Foreign Application Priority Data

Jun. 2, 2014 (GB) .................................. 1409792.7
Oct. 21, 2014 (GB) .................................. 1418676.1

(51) Int. Cl.
A61K 41/00 (2006.01)
A61K 31/385 (2006.01)
(Continued)

(52) U.S. Cl.
CPC ........ *A61K 41/0061* (2013.01); *A61K 31/385* (2013.01); *A61K 31/44* (2013.01);
(Continued)

(58) Field of Classification Search
None
See application file for complete search history.

(56) References Cited

U.S. PATENT DOCUMENTS

| 3,635,945 A | 1/1972 | Nemeth et al. |
| 9,919,049 B2 | 3/2018 | Wood et al. |

(Continued)

FOREIGN PATENT DOCUMENTS

| CA | 2 354 743 A1 | 2/2003 |
| CN | 103012394 A | 4/2013 |

(Continued)

OTHER PUBLICATIONS

Google patents Machine Translation of EP 2440179, retrieved from the internet on Jul. 23, 2018 at https://patents.google.com/patent/EP2440179A2/en?oq=%222440179%22.*

(Continued)

*Primary Examiner* — Karl J Puttlitz

(57) ABSTRACT

The invention relates to a combination comprising
(i) a compound A comprising a mitochondrial targeting group linked to a group capable of releasing hydrogen sulfide or a pharmaceutically acceptable salt thereof or a prodrug thereof, an inhibitor of the thioredoxin antioxidant system or a pharmaceutically acceptable salt thereof or a prodrug thereof, and/or a nitroxide or a pharmaceutically acceptable salt thereof or a prodrug thereof; and
(ii) a photosensitizer or photosensitizer precursor;
for use in photodynamic therapy.

8 Claims, 40 Drawing Sheets

(51) Int. Cl.
| | |
|---|---|
| A61K 31/44 | (2006.01) |
| A61K 31/7135 | (2006.01) |
| A61K 33/24 | (2006.01) |
| A61K 31/445 | (2006.01) |
| A61K 31/454 | (2006.01) |
| A61K 31/67 | (2006.01) |
| A61K 47/54 | (2017.01) |

(52) U.S. Cl.
CPC .......... *A61K 31/445* (2013.01); *A61K 31/454* (2013.01); *A61K 31/67* (2013.01); *A61K 31/7135* (2013.01); *A61K 33/24* (2013.01); *A61K 41/0071* (2013.01); *A61K 47/54* (2017.08)

(56) References Cited

U.S. PATENT DOCUMENTS

| | | |
|---|---|---|
| 2007/0010506 A1 | 1/2007 | Chang et al. |
| 2008/0004245 A1 | 1/2008 | Wallace et al. |
| 2010/0273743 A1 | 10/2010 | Moore et al. |
| 2015/0196034 A1 | 7/2015 | Wood et al. |
| 2017/0202966 A1 | 7/2017 | Wood et al. |

FOREIGN PATENT DOCUMENTS

| | | |
|---|---|---|
| CN | 103610667 A | 3/2014 |
| WO | 2006/113914 A2 | 10/2006 |
| WO | 2007/046729 A1 | 4/2007 |
| WO | 2008/146105 A1 | 12/2008 |
| WO | 2009/012534 A1 | 1/2009 |
| WO | 2009/065926 A2 | 5/2009 |
| WO | 2010/001102 A2 | 1/2010 |
| WO | 2010/052310 A1 | 5/2010 |
| WO | 2010/110684 A1 | 9/2010 |
| WO | 2011/134275 A1 | 11/2011 |
| WO | 2013/045951 A1 | 4/2013 |
| WO | 2014/033477 A1 | 3/2014 |
| WO | 2014/075574 A1 | 5/2014 |
| WO | 2015/185918 A1 | 12/2015 |

OTHER PUBLICATIONS

Casini et al., "Gold(III) compounds as anticancer agents: Relevance of gold-protein interactions for their mechanism of action", Journal of Inorganic Biochemistry, 2008, pp. 564-575, vol. 102.
Fuchs et al., "Cutaneous tolerance to nitroxide free radicals and nitrone spin traps in the guinea pig", Toxicology, 1998, pp. 33-40, vol. 126.
GB Search Report from Application No. GB1409792.7, dated Feb. 6, 2015, 5 pgs.
GB Search Report from Application No. GB1418676.1, dated Jul. 2, 2015, 5 pgs.
Kean et al., "Disease-Modifying Drugs, Series Editor: T. Puller, Auranofin", British Journal of Rheumatology, 1997, pp. 560-572, vol. 36, No. 5.
Kinoshita et al., "In vivo evaluation of novel nitroxyl radicals with reduction stability", Free Radical Biology & Medicine, 2010, pp. 1703-1709, vol. 49.
Metz et al., "A Phase I Study of Topical Tempol for the Prevention of Alopecia Induced by Whole Brain Radiotherapy", Clinical Cancer Research, 2004, pp. 6411-6417, vol. 10.
Mirabelli et al., "Evaluation of the in Vivo Antitumor Activity and in Vitro Cytotoxic Properties of Auranofin, a Coordinated Gold Compound, in Murine Tumor Models", Cancer Research, 1985, pp. 32-39, vol. 45.
Regala et al., "Atypical Protein Kinase Cι Expression and Aurothiomalate Sensitivity in Human Lung Cancer Cells", Cancer Research, 2008, pp. 5888-5895, vol. 68.
Sadler et al., "The Chemistry of Gold Drugs", Metal-Based Drugs, 1994, pp. 107-144, vol. 1, Nos. 2-3.
Sannella et al., "New uses for old drugs. Auranofin, a clinically established antiarthritic metallodrug, exhibits potent antimalarial effects in vitro: Mechanistic and pharmacological implications", FEBS Letters, 2008, pp. 844-847, vol. 582.
Wachowska et al., "Aminolevulinic Acid (ALA) as a Prodrug in Photodynamic Therapy of Cancer", Molecules, 2011, pp. 4140-4164, vol. 16.
Wilcox, "Effects of tempol and redox-cycling nitroxides in models of oxidative stress", Pharmacology & Therapeutics, 2010, pp. 119-145, vol. 126.
Wondrak, "Redox-Directed Cancer Therapeutics: Molecular Mechanisms and Opportunities", Antioxidants & Redox Signaling, 2009, pp. 3013-3069, vol. 11, No. 12.
Arner et al., "1-Chloro-2,4-dinitrobenzene Is an Irreversible Inhibitor of Human Thioredoxin Reductase: Loss of Thioredoxin Disulfide Reductase Activity Is Accompanied by a Large Increase in NADPH Oxidase Activity", The Journal of Biological Chemistry, 1995, pp. 3479-3482, vol. 270, No. 8.
Berge et al., "Pharmaceutical Salts", Journal of Pharmaceutical Sciences, 1977, pp. 1-19, vol. 66, No. 1.
Busch et al., "Diallylpolysulfides induce growth arrest and apoptosis", International Journal of Oncology, 2010, pp. 743-749, vol. 36.
Cai et al., "Small molecule inhibitors of mammalian thioredoxin reductase", Free Radical Biology & Medicine, 2012, pp. 257-265, vol. 52, No. 2.
Caliendo et al., "Synthesis and Biological Effects of Hydrogen Sulfide (H2S): Development of H2S-Releasing Drugs as Pharmaceuticals", Journal of Medicinal Chemistry, 2010, pp. 6275-6286, vol. 53, No. 17.
Cortese-Krott et al., "Nitrosopersulfide (SSNO—) accounts for sustained NO bioactivity of S-nitrosothiols following reaction with sulfide", Redox Biology, 2014, pp. 234-244, vol. 2.
D'Souza et al., "DQAsome-mediated delivery of plasmid DNA toward mitochondria in living cells", Journal of Controlled Release, 2003, pp. 189-197, vol. 92, Nos. 1-2.
D'Souza et al., "Mitochondrial leader sequence-plasmid DNA conjugates delivered into mammalian cells by DQAsomes co-localize with mitochondria", Mitochondrion, 2005, pp. 352-358, vol. 5.
Ferguson et al., "Potentiation of Methyl Aminolevulinate (MAL)-Induced Photodynamic Therapy (PDT) Killing of Skin Cancer Cells by Mitochondria-Targeted Hydrogen Sulfide (H2S) Donors", Free Radical Biology & Medicine, 2014, p. S135, vol. 76.
Finkelstein et al., "Auranofin. New oral gold compound for treatment of rheumatoid arthritis", Annals of the Rheumatic Diseases, 1976, pp. 251-257, vol. 35.
Gromer et al., "Human Placenta Thioredoxin Reductase: Isolation of the Selenoenzyme, Steady State Kinetics, and Inhibition by Therapeutic Gold Compounds", The Journal of Biological Chemistry, 1998, pp. 20096-20101, vol. 273, No. 32.
Horinouchi et al., "Photoinduced Nitric Oxide Release from a Nitrobenzene Derivative in Mitochondria", European Journal of Chemistry, 2011, pp. 4809-4813, vol. 17, No. 17.
Horton et al., "Mitochondria-Penetrating Peptides", Chemistry & Biology, 2008, pp. 375-382, vol. 15.
Hoye et al., "Targeting Mitochondria", Accounts of Chemical Research, 2008, pp. 87-97, vol. 41, No. 1.
International Search Report and Written Opinion from related International Application No. PCT/GB2015/051608, dated Oct. 13, 2015, 16 pgs.
Kanai et al., "Mitochondrial targeting of radioprotectants using peptidyl conjugates", Org. Biomol. Chem., 2007, pp. 307-309, vol. 5, No. 2.
Kang et al., "Combinatorial drug design targeting multiple cancer signaling networks controlled by mitochondrial Hsp90", The Journal of Clinical Investigation, 2009, pp. 454-464, vol. 119, No. 3.
Krishna et al., "Oxoammonium cation intermediate in the nitroxide-catalyzed dismutation of superoxide", Proc. Natl. Acad. Sci. USA, 1992, pp. 5537-5541, vol. 89.
Le Trionnaire et al., "The synthesis and functional evaluation of a mitochondria-targeted hydrogen sulfide donor, (10-oxo-10-(4-(3-

(56) References Cited

OTHER PUBLICATIONS thioxo-3H-1,2-dithiol-5-yl)-phenoxy) decyl)triphenylphosphonium bromide (AP39)", Med. Chem. Commun., 2014, pp. 728-736, vol. 5.
Li et al., "Characterization of a Novel, Water-Soluble Hydrogen Sulfide-Releasing Molecule (GYY4137): New Insights into the Biology of Hydrogen Sulfide", Circulation, 2008, pp. 2351-2360, vol. 117.
Liu et al., "Capture and Visualization of Hydrogen Sulfide via a Fluorescent Probe", Angew Chem Int Ed Engl., 2011, pp. 10327-10329, vol. 50, No. 44.
Luo et al., "Hydrogen sulfide prevents hypoxia-induced apoptosis via inhibition of an H2O2-activated calcium signaling pathway in mouse hippocampal neurons", Biochemical and Biophysical Research Communications, 2012, pp. 473-477, vol. 425.
Maiti et al., "Guanidine-Containing Molecular Transporters: Sorbitol-Based Transporters Show High Intracellular Selectivity toward Mitochondria", Angew. Chem. Int. Ed., 2007, pp. 5880-5884, vol. 46.
Modica-Napolitano et al., "Selective Damage to Carcinoma Mitochondria by the Rhodacyanine MKT-077", Cancer Research, 1996, pp. 544-550, vol. 56.
Monti et al., "Protective Effect of the Nitroxide Ternpol Against the Cardiotoxicity of Adriamycin", Free Radical Biology & Medicine, 1996, pp. 463-470, vol. 21, No. 4.
Murphy et al., "Targeting Antioxidants to Mitochondria by Conjugation to Lipophilic Cations", Annual Review of Pharmacology and Toxicology, 2007, pp. 629-656, vol. 47.
Rapozzi et al., "Nitric oxide-mediated activity in anti-cancer photodynamic therapy", Nitric Oxide, 2013, pp. 26-35, vol. 30.
Senkal et al., "Potent Antitumor Activity of a Novel Cationic Pyridinium-Ceramide Alone or in Combination with Gemcitabine against Human Head and Neck Squamous Cell Carcinomas in Vitro and in Vivo", The Journal of Pharmacology and Experimental Therapeutics, 2006, pp. 1188-1199, vol. 317, No. 3.
Szczesny et al., "AP 39 [10-oxo-10-(4-(3-thioxo-3H-1,2-dithiol-5yl)phenoxy)decyl) triphenyiphosphonium bromide], a mitochondrially targeted hydrogen sulfide donor, stimulates cellular bioenergetics, exerts cytoprotective effects and protects against the loss of mitochondrial DNA integrity in oxidatively stressed endothelial cells in vitro", Nitric Oxide, 2014, pp. 120-130, vol. 41.
Tanito et al., "Protective Effect of TEMPOL Derivatives against Light-Induced Retinal Damage in Rats", Investigative Ophthalmology & Visual Science, 2007, pp. 1900-1905, vol. 48, No. 4.
Wang et al., "Cu-Labeled Triphenylphosphonium and Triphenylarsonium Cations as Highly Tumor-Selective Imaging Agents", Journal of Medicinal Chemistry, 2007, pp. 5057-5069, vol. 50, No. 21.
Weiss et al., "Dequaliniun, a topical antimicrobial agent, displays anticarcinoma activity based on selective mitochondrial accumulation", Proc. Natl. Acad. Sci. USA, 1987, pp. 5444-5448, vol. 84.
Whiteman et al., "The novel neuromodulator hydrogen sulfide: an endogenous peroxynitrite 'scavenger'?", Journal of Neurochemistry, 2004, pp. 765-768, vol. 90, No. 3.
Whiteman et al., "Hydrogen sulphide: a novel inhibitor of hypochlorous acid-mediated oxidative damage in the brain?", Biochemical and Biophysical Research Communications, 2005, pp. 794-798, vol. 326, No. 4.
Whiteman et al., "Evidence for the formation of a novel nitrosothiol from the gaseous mediators nitric oxide and hydrogen sulphide", Biochemical and Biophysical Research Communications, 2006, pp. 303-310, vol. 343, No. 1.
Zimmer et al., "Effect of the triaminopyridine flupirtine on calcium uptake, membrane potential and ATP synthesis in rat heart mitochondria", British Journal of Pharmacology, 1998, pp. 1154-1158, vol. 123, No. 6.
Rafalowska et al., "Metabolic Changes in Rat Brain Synaptosomes After Exposure to Sulfide in Vivo", Toxicology Letters, 1986, pp. 193-200, vol. 34.

Reynolds, "Potential Relevance of Bell-Shaped and U-Shaped Dose-Responses for the Therapeutic Targeting of Angiogenesis in Cancer", Dose-Response, 2010, pp. 253-284, vol. 8.
Nicholson et al., "Inhibition of Respiratory and Bioenergetic Mechanisms by Hydrogen Sulfide in Mammalian Brain", Journal of Toxicology and Environmental Health, Part A: Current Issues, 1998, pp. 491-507, vol. 54.
Schiller et al., "Synthesis and in vitro opioid activity profiles of DALDA analogues", European Journal of Medicinal Chemistry, 2000, pp. 895-901, vol. 35, No. 10.
Tazzari et al., "New aryldithiolethione derivatives as potent histone deacetylase inhibitors", Bioorganic & Medicinal Chemistry, 2010, pp. 4187-4194, vol. 18.
Tomasova et al., "Effects of AP39, a novel triphenylphosphonium derivatised anethole dithiolethione hydrogen sulfide donor, on rat haemodynamic parameters and chloride and calcium Cav3 and RyR2 channels", Nitric Oxide, 2015, pp. 131-144, vol. 46.
Truong et al., "Molecular Mechanisms of Hydrogen Sulfide Toxicity", Drug Metabolism Reviews, 2006, pp. 733-744, vol. 38.
Vacek et al., "Hydrogen sulfide protects against vascular remodeling from endothelial damage", Amino Acids, 2010, pp. 1161-1169, vol. 39.
Vauzour et al., "Champagne Wine Polyphenols Protect Primary Cortical Neurons against Peroxynitrite-Induced Injury", Journal of Agricultural and Food Chemistry, 2007, pp. 2854-2860, vol. 55, No. 8.
Virieux et al., "A review of methods to prepare alkylphosphonium salts", Science of Synthesis, 2009, vol. 42; English Abstract Only.
Wagner, "Hydrogen sulfide: a new gaseous signal molecule and blood pressure regulator", Journal of Nephrology, 2009, pp. 173-176, vol. 22.
Wallace et al., "Gastrointestinal Safety and Anti-Inflammatory Effects of a Hydrogen Sulfide-Releasing Diclofenac Derivative in the Rat", Gastroenterology, 2007, pp. 261-271, vol. 132.
Wang et al., "Generation of a Stable Antioxidant Response Element-Driven Reporter Gene Cell Line and Its Use to Show Redox-Dependent Activation of Nrf2 by Cancer Chemotherapeutic Agents", Cancer Research, 2006, pp. 10983-10994, vol. 66, No. 22.
Wang et al., "The use of mitochondrial targeting resveratrol liposomes modified with a dequalinium polyethylene glycol-distearoylphosphatidyl ethanolamine conjugate to induce apoptosis in resistant lung cancer cells," Biomaterials, 2011, pp. 5673-5687, vol. 32, No. 24.
Warenycia et al., "Monoamine oxidase inhibition as a sequel of hydrogen sulfide intoxication: increases in brain catecholamine and 5-hydroxytryptamine levels", Archives of Toxicology, 1989, pp. 131-136, vol. 63.
Warenycia et al., "Acute Hydrogen Sulfide Poisoning: Demonstration of Selective Uptake of Sulfide by the Brainstem by Measurement of Brain Sulfide Levels", Biochemical Pharmacology, 1989, pp. 973-981, vol. 38, No. 6.
Whiteman et al., "Peroxynitrite mediates calcium-dependent mitochondrial dysfunction and cell death via activation of calpains", The FASEB Journal, 2004, 35 pgs., vol. 18.
Whiteman et al., "Detection and Measurement of Reactive Oxygen Intermediates in Mitochondria and Cells", Methods in Molecular Biology, 2008, pp. 29-50, vol. 476.
Whiteman et al., "Hydrogen sulfide and the vasculature: a novel vasculoprotective entity and regulator of nitric oxide bioavailability?", J. Cell. Mol. Med., 2009, pp. 488-507, vol. 13, No. 3.
Whiteman et al., "Hydrogen sulfide and inflammation: the good, the bad, the ugly and the promising", Expert Reviews in Clinical Pharmacology, 2011, pp. 13-32, vol. 4, No. 1.
Yamada et al., "MITO-Porter: A liposome-based carrier system for delivery of macromolecules into mitochondria via membrane fusion", Biochimica et Biophysica Acta, 2008, pp. 423-432, vol. 1778, No. 2.
Yoshida et al., "α-Thiocarbonyl-stabilized Triphenylphosphonium Ylides: Preparation, Structure, and Alkylation Reactions", Bulletin of the Chemical Society of Japan, 1975, pp. 2907-2910, vol. 48, No. 10.
Zabbarova et al., "Targeted Delivery of Radioprotective Agents to Mitochondria", Mol. Interv., 2008, pp. 294-302, vol. 8, No. 6.

(56) References Cited

OTHER PUBLICATIONS

Zhang et al., "Role of Hydrogen Sulfide in Severe Burn Injury—Induced Inflammation in Mice", Mol. Med., 2010, pp. 417-424, vol. 16.
Zhao et al., "AP39, a Mitochondria-Targeted Hydrogen Sulfide Donor, Supports Cellular Bioenergetics and Protects against Alzheimer's Disease by Preserving Mitochondrial Function in APP/PS1 Mice and Neurons", Oxidative Medicine and Cellular Longevity, 19 pgs., vol. 2016, Article ID 8360738.
Ahmad et al., "AP39, A Mitochondrially Targeted Hydrogen Sulfide Donor, Exerts Protective Effects in Renal Epithelial Cells Subjected to Oxidative Stress in vitro and in Acute Renal Injury in vivo", SHOCK, 2016, pp. 88-97, vol. 45, No. 1.
Ahmad et al., "Both the H2S biosynthesis inhibitor aminooxyacetic acid and the mitochondrially targeted H2S donor AP39 exert protective effects in a mouse model of burn injury", Pharmacological Research, 2016, pp. 348-355, vol. 113.
Bhatia, "Hydrogen Sulfide as a Vasodilator", IUBMB Life, 2005, pp. 603-606, vol. 57, No. 9.
Bhatia et al., "Treatment with H2S-Releasing Diclofenac Protects Mice Against Acute Pancreatitis-Associated Lung Injury", SHOCK, 2008, pp. 84-88, vol. 29, No. 1.
Carballal et al., "Reactivity of hydrogen sulfide with peroxynitrite and other oxidants of biological interest", Free Radical Biology & Medicine, 2011, pp. 196-205, vol. 50.
Chatzianastasiou et al., "Cardioprotection by H2S Donors: Nitric Oxide-Dependent and -Independent Mechanisms", The Journal of Pharmacology and Experimental Therapeutics, 2016, pp. 431-440, vol. 358.
Chopra et al., "Contrasting Effects of 'Fast' and 'Slow' Releasing H2S Donors on β Cell Viability in the Diabetic Milieu", Free Radical Biology & Medicine, 2010, p. S43, vol. 49, Suppl. 1.
Eghbal et al., "H2S cytotoxicity mechanism involves reactive oxygen species formation and mitochondrial depolarisation", Toxicology, 2004, pp. 69-76, vol. 203.
EPA, "Toxicological Review of Hydrogen Sulfide", U.S. Environmental Protection Agency, Washington, DC, Jun. 2003, (CAS No. 7783-06-4), 74 pgs.
Fiorucci et al., "Hydrogen Sulfide-Based Therapies: Focus on H2S Releasing NSAIDs", Inflammation & Allergy—Drug Targets, 2011, pp. 133-140, vol. 10, No. 2.
Fox et al., "Inducible hydrogen sulfide synthesis in chondrocytes and mesenchymal progenitor cells: is H2S a novel cytoprotective mediator in the inflamed joint?", Journal of Cellular and Molecular Medicine, 2012, pp. 896-910, vol. 16, No. 4.
Fujita et al., "A Fatal Case of Acute Hydrogen Sulfide Poisoning Caused by Hydrogen Sulfide: Hydroxocobalamin Therapy for Acute Hydrogen Sulfide Poisoning", Journal of Analytical Toxicology, 2011, pp. 119-123, vol. 35.
GB Search Report from related GB Application No. GB1117095.8, dated Jan. 23, 2012; 5 pgs.
Gero et al., "The novel mitochondria-targeted hydrogen sulfide (H2S) donors AP123 and AP39 protect against hyperglycemic injury in microvascular endothelial cells in vitro", Pharmacological Research, 2016, pp. 186-198, vol. 113.
Guidotti, "Occupational exposure to hydrogen sulfide in the sour gas industry: some unresolved issues", Int Arch Occup Environ Health, 1994, pp. 153-160, vol. 66.
Ikeda et al., "Mitochondria-targeted hydrogen sulfide donor AP39 improves neurological outcomes after cardiac arrest in mice", Nitric Oxide, 2015, pp. 90-96, vol. 49.
International Preliminary Report on Patentability from related International Application No. PCT/GB2012/052424, dated Apr. 1, 2014; 7 pgs.
International Search Report and Written Opinion from related International Application No. PCT/GB2012/052424, dated Feb. 8, 2013; 13 pgs.
Kage et al., "Fatal hydrogen sulfide poisoning at a dye works", Legal Medicine, 2004, pp. 182-186, vol. 6.
Kimura et al., "Hydrogen sulfide increases glutathione production and suppresses oxidative stress in mitochondria", J. Pharmacol. Sci., 2010, 112 (Suppl. 1), p. 88P, Abstract No. OIE-1-3.
Kozlov et al., "Phosphorus-substituted carbothioamides", Russian Chemical Bulletin, International Edition, Apr. 2004, pp. 925-931, vol. 53, No. 4.
Kozlov et al., "Factors Determining the Stereochemical Structure of 2-(Phosphorus Substituted) Methylidene-thiazolidine-4-ones in Solid State and in Solution", Phosphorus, Sulfur, and Silicon, 2009, pp. 830-845, vol. 184, No. 4.
Lee et al., "Effects of Hydrogen Sulfide-releasing L-DOPA Derivatives on Glial Activation", The Journal of Biological Chemistry, 2010, pp. 17318-17328, vol. 285, No. 23.
Lee et al., "The Slow-Releasing Hydrogen Sulfide Donor, GYY4137, Exhibits Novel Anti-Cancer Effects In Vitro and In Vivo", PLoS ONE, 2011, e21077, pp. 1-7, vol. 6, No. 6.
Li et al., "GYY4137, a novel hydrogen sulfide-releasing molecule, protects against endotoxic shock in the rat", Free Radical Biology & Medicine, 2009, pp. 103-113, vol. 47, No. 1.
Lisjak et al., "A novel hydrogen sulfide donor causes stomatal opening and reduces nitric oxide accumulation", Plant Physiology and Biochemistry, 2010, pp. 931-935, vol. 48, No. 12.
Lobb et al., "Hydrogen Sulfide Protects Renal Grafts Against Prolonged Cold Ischemia-Reperfusion Injury via Specific Mitochondrial Actions", American Journal of Transplantation, 2016, pp. 1-12.
Maebashi et al., "Toxicological analysis of 17 autopsy cases of hydrogen sulfide poisoning resulting from the Inhalation of intentionally generated hydrogen sulfide gas", Forensic Science International, 2011, pp. 91-95, vol. 207.
Malekova et al., "H2S and HS- donor NaHS inhibits intracellular chloride channels", General Physiology and Biophysics, 2009, pp. 190-194, vol. 28.
Martell et al., "Physiopathology of splanchnic vasodilation in portal hypertension", World Journal of Hepatology, 2010, pp. 208-220, vol. 2, No. 6.
Milby et al., "Hydrogen Sulfide Poisoning: Clarification of Some Controversial Issues", American Journal of Industrial Medicine, 1999, pp. 192-195, vol. 35.
Minamishima et al., "Emerging Role of Hydrogen Sulfide in Organ Protection and Survival", ICU and CCU, 2009, pp. 993-1000, vol. 33, No. 12, with partial English Translation.
Olson, "The therapeutic potential of hydrogen sulfide: separating hype from hope", American Journal of Physiology—Regulatory Integrative and Comparative Physiology, 2011, pp. R297-R312, vol. 301, No. 2.
Osha Fact Sheet, "Hydrogen Sulfide (H2S)", U.S. Department of Labor, Oct. 2005, 2 pgs.
Predmore et al., "Hydrogen sulfide-mediated myocardial pre- and post-conditioning", Expert Review of Clinical Pharmacology, 2011, pp. 83-96, vol. 4, No. 1.
Querellou et al., "Intoxication accidentelle mortelle par hydrogene sulfure Fatal outcome of an hydrogen sulfide poisoning", Annales Francaises d' Anesthesie et de Reanimation, 2005, pp. 1302-1304, vol. 24.
Quintanilla et al., "Caspase-cleaved Tau Expression Induces Mitochondrial Dysfunction in Immortalized Cortical Neurons", The Journal of Biological Chemistry, 2009, pp. 18754-18766, vol. 284, No. 28.

\* cited by examiner

COMBINATIONS OF A PHOTOSENSITIZER WITH A HYDROGEN SULFIDE DONOR, THIOREDOXIN INHIBITOR OR NITROXIDE FOR USE IN PHOTODYNAMIC THERAPY

CROSS-REFERENCE TO RELATED APPLICATIONS

This patent application is a continuation of U.S. patent application Ser. No. 15/315,699, filed Dec. 1, 2016, which is a National Stage of International Patent Application No. PCT/GB2015/051608, filed Jun. 2, 2015, which claims benefit of GB 1418676.1, filed Oct. 21, 2014, and GB 1409792.7, filed Jun. 2, 2014, the disclosure of each is hereby incorporated by reference in its entirety.

FIELD OF THE INVENTION

This invention relates to combinations for use in photodynamic therapy, as well as related uses, methods and compositions.

In particular, though not exclusively, the present invention relates to a combination comprising: (i) a compound A comprising a mitochondrial targeting group linked to a group capable of releasing hydrogen sulfide or a pharmaceutically acceptable salt thereof or a prodrug thereof, an inhibitor of the thioredoxin antioxidant system or a pharmaceutically acceptable salt thereof or a prodrug thereof, and/or a nitroxide or a pharmaceutically acceptable salt thereof or a prodrug thereof; and (ii) a photosensitizer or photosensitizer precursor; for use in photodynamic therapy. Aspects of the invention relate to the use of this combination in photodynamic treatment for cosmetic purposes; and to a composition comprising components (i) and (ii).

BACKGROUND TO THE INVENTION

Photodynamic therapy (PDT) is a therapy employed routinely in the treatment of superficial dermatological malignancies and is under investigation for a range of additional tumour types. Most applications of PDT involve the use of an active compound, known as a photosensitizer, and a light source, the wavelength of which can be chosen to be appropriate for exciting the photosensitizer to produce reactive oxygen species. This leads to the destruction of any tissues which have either selectively taken up the photosensitizer or have been locally exposed to light.

For example, a PDT treatment of human skin cancer may involve the following steps. Firstly, a photosensitizer precursor is administered to the patient. The photosensitizer precursor is taken up by the cells and converted to a photosensitizer. The area to be treated is then exposed to light of the appropriate wavelength. The photosensitizer absorbs light and reacts with nearby tissue oxygen, resulting in reactive oxygen species. These reactive oxygen species react with biomolecules, fatally damaging some of the cells in the treatment area.

PDT has particularly found a niche in the treatment of dermatological tumours where light can be readily applied to the surface of the skin; clinically substantial subsets of skin tumours are difficult to treat by conventional therapies (because of size, site or multiple lesions presentation). In the treatment of skin conditions, the photosensitizer or photosensitizer precursor can be applied topically, and locally excited by a light source. In the local treatment of internal cancer cells, on the other hand, photosensitizers or photosensitizer precursors can for example be administered intravenously and light can be delivered to the target area using endoscopes and fibre optic catheters. Compared to normal healthy tissues, most types of cancer cells are especially active in both the uptake and accumulation of photosensitizers, which makes cancer cells especially vulnerable to PDT, since having more photosensitizer present in a cell leads to more damage to that cell during PDT.

Photosensitizer precursors currently employed in dermatological PDT include aminolaevulinic acid (ALA), methyl aminolaevulinate (MAL) and hexyl aminolaevulinate (HAL). If ALA, MAL or HAL is used as a photosensitizer precursor, it is converted by the cells to the photosensitizer protoporphyrin IX (PpIX).

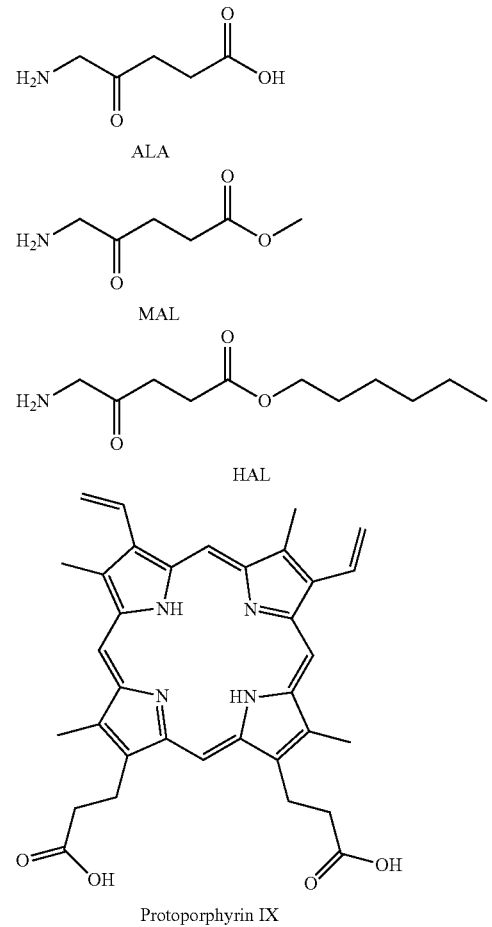

Porphyrins have long been considered as suitable agents for tumour photodiagnosis and tumour PDT because cancer cells exhibit a significantly greater uptake and affinity for porphyrins compared to normal quiescent tissues; cancer cells therefore naturally accumulate porphyrins. An additional feature of the photosensitizer protoporphyrin IX (PpIX) is its ability to fluoresce, which in combination with cancer cells' natural accumulation of porphyrins allows for photodiagnosis (PD) of tumours. PD has been used by surgeons for enabling greater precision in the removal of tumours, such as for example brain tumours.

PpIX is naturally present in all nucleated mammalian cells at low concentrations; it is an intermediate in the biosynthesis of haem. In the haem biosynthesis, ALA is converted to PpIX (via a number of intermediate steps), after which PpIX is converted to haem by the insertion of a $Fe^{2+}$ ion into PpIX by the enzyme ferrochelatase.

In order for PDT to be effective, it is necessary to increase the amount of PpIX which is present in a cell, which can be achieved by adding more ALA, MAL or HAL to a cell, which will be converted to PpIX. However, the haem biosynthesis pathway has a maximum limit over which additional precursor administration does not produce any additional benefit. Furthermore, excessive ALA oral administration has been demonstrated to induce liver toxicity in humans. Usually, the presence of free haem acts as a negative feedback mechanism inhibiting ALA synthesis. However, the exogenous administration of large amounts of ALA or MAL bypasses this negative feedback signal and results in a temporary accumulation of PpIX within the cells, since the insertion of $Fe^{2+}$ into PpIX to form haem is relatively slow.

Known ways to improve the activity profile in photodynamic therapy include limiting the iron supply in a cell by using the iron chelator CP94, which slows down the step of converting PpIX to haem by insertion of $Fe^{2+}$, allowing PpIX to accumulate in the cell.

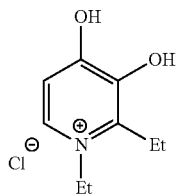

CP94

A need however remains for other ways to improve the activity profile in photodynamic therapy, especially since currently photodynamic therapy is not effective for all tumour types.

STATEMENTS OF THE INVENTION

Aspects of the invention relate to a combination comprising components (i) and (ii) as defined below. The combination may be for use in photodynamic therapy, or use in photodynamic treatment for cosmetic purposes. The combination may also be comprised in a composition.

According to a first aspect of the invention there is provided a combination comprising
(i) a compound A comprising a mitochondrial targeting group linked to a group capable of releasing hydrogen sulfide or a pharmaceutically acceptable salt thereof or a prodrug thereof, an inhibitor of the thioredoxin antioxidant system or a pharmaceutically acceptable salt thereof or a prodrug thereof, and/or a nitroxide or a pharmaceutically acceptable salt thereof or a prodrug thereof; and
(ii) a photosensitizer or photosensitizer precursor;
for use in photodynamic therapy.

In an embodiment, the inhibitor of the thioredoxin antioxidant system is a thioredoxin reductase inhibitor or a thioredoxin inhibitor. In an embodiment, the inhibitor of the thioredoxin antioxidant system is a thioredoxin reductase inhibitor. In an embodiment, the inhibitor of the thioredoxin antioxidant system is a thioredoxin inhibitor.

For the avoidance of doubt, the term "combination" is used herein to signify that the components may be provided in any suitable form for administration to a patient for concurrent or combined action in photodynamic therapy.

Thus the combination may comprise one or more combined compositions comprising both components (i) and (ii), or a kit comprising a plurality of compositions together providing the components (i) and (ii). A kit may suitably comprise one or more compositions comprising one only of the components. In an embodiment, a kit comprises a first composition comprising component (i) and a second composition comprising component (ii). The compositions or components may be of any suitable form to achieve administration of the components to a patient for concurrent or combined action in photodynamic therapy. For example, the compositions or components may be adapted for topical, oral, intravenous, intraperitoneal, intradermal or intra-articular administration.

Using a "combination" comprising component (i) and component (ii) in photodynamic therapy means that both of the components are administered to a patient undergoing photodynamic therapy, either simultaneously or sequentially. The components may be administered as part of the same composition or separately.

For the avoidance of doubt, use in photodynamic therapy herein means that cells are exposed to both components (i) and (ii) after which those cells are then exposed to light, resulting in at least some of the cells being fatally damaged. In other words, both components (i) and (ii) are used for killing cells on exposure of the cells to light.

In an embodiment, the cells are mammalian cells, such as for example human cells.

In an embodiment, the effect of the photosensitizer or photosensitizer precursor (component (ii)) on cell death is synergistically enhanced by component (i), which means that the effect of the combination of components (i) and (ii) on cell death is greater than the sum of the effects of components (i) and (ii) when they are used individually.

In an embodiment of the first aspect of the invention, the combination for use in photodynamic therapy comprises
(i) said compound A comprising a mitochondrial targeting group linked to a group capable of releasing hydrogen sulfide, or a pharmaceutically acceptable salt thereof or a prodrug thereof, and
(ii) said photosensitizer or a photosensitizer precursor.

Slow release hydrogen sulfide donors (SRHDs) can be mitochondrially targeted by linking an $H_2S$ releasing group to a mitochondrial targeting group. Mitochondrially targeted SRHDs were previously described in WO 2013/045951, which describes investigations into the ability of non-targeted SHRD GYY4137 and mitochondrially targeted SRHDs AP39-C10 and AP123-C10 to attenuate oxidative stress and damage in human brain microvascular endothelial cells (HMEC). WO 2013/045951 showed that AP39-C10 and GYY4137 inhibit cell death, mitochondrial dysfunction, mitochondrial and cytoplasmic oxidative stress when cells are challenged with a range of physiological oxidant species, and that mitochondrial targeting of $H_2S$ confers greater cytoprotection than non-targeted donor molecules. Le Trionnaire S et al., Med. Chem. Commun., 2014, 5, 728-736, and Szczesnya B et al., Nitric Oxide, 2014, DOI: 10.1016/j.niox.2014.04.008 describe that significant protective effects were observed for GYY4137 as well as AP39-C10 and AP123-C10, with AP39-C10 and AP123-C10 being found significantly more potent. The loss of mitochondrial membrane potential was attenuated by all of the SRHDs investigated and the generation of reactive oxygen species (ROS) was considerably decreased.

This embodiment of the first aspect of the invention is concerned with using SRHDs in conjunction with a pro-oxidant treatment, namely photodynamic therapy. As can be seen from Example 1, the inventors have found that the use of non-targeted H$_2$S releasing compounds GYY4137, ADT-OH and 4-HTB in combination with MAL and irradiation had no statistically significant effect on photodynamic cell killing, exhibiting similar levels of cell death compared to MAL only with irradiation. Surprisingly, however, the use of mitochondrially targeted SRHDs AP39-C8, AP39-C10, AP39-C12, AP123-C8, AP123-C10 or AP123-C12 in combination with MAL and irradiation significantly increased cell killing compared to MAL only with irradiation (see FIGS. 1 and 3).

This observed result runs counter to the vast majority of the research that has been carried out investigating H$_2$S and its role in oxidative stress. For the most part, endogenous H$_2$S is thought to be responsible for maintaining redox homeostasis through scavenging of ONOO$^-$, H$_2$O$_2$, ClO$^-$, O$_2^{\cdot-}$ and/or $\cdot$NO. By mediating the reduction of these reactive oxygen species (ROS), H$_2$S has been shown to prevent the oxidation of proteins and lipoproteins (Whiteman M et al., Biochem Biophys Res Commun, 2006, Apr. 28, 343(1):303-10; Whiteman M et al., J Neurochem., 2004 August, 90(3):765-8; Luo Y et al., Biochem Biophys Res Commun, 2012, 425, 473-7; Whiteman M et al., Biochem Biophys Res Commun, 2005, 326, 794-8).

Without wishing to be bound by theory, the observation that mitochondrially-targeted SRHDs significantly enhanced photodynamic cell killing may be due to the relatively high concentration of the donors localised to the mitochondria. These concentrated donors could release concentrated and localised H$_2$S, potentially eliciting localised effects far more rapidly than the non-targeted alternatives. Although these mechanisms are not yet elucidated, it may be possible that short-term incubation of cells with mitochondrially targeted SRHD is enough to elicit an inhibition of glucose metabolism, which in turn may sensitise the cells to photodynamic cell killing.

Without wishing to be bound by theory, another explanation may involve the potential interaction between the mitochondrially targeted SRHD and irradiation in the presence of a photosensitizer (such as for example PpIX), which could potentially be inducing photo-dissociation of parts of the H$_2$S releasing moieties. Experiments carried out in a cell-free system (see Example 1 and FIGS. 5 and 6) found that this may be occurring, as irradiation of AP39-C10 and AP123-C10 in the presence of photosensitizer PpIX was found to increase the release of H$_2$S.

Additionally, without wishing to be bound by theory, the interaction between light and hydrogen sulfide in the presence of a photosensitizer (such as for example PpIX) may lead to the generation of polysulfides, thiyl or sulfanyl (HS.) radicals. Additionally or alternatively, it may lead to the generation of persulfides, thiosulfate or sulfite. Polysulfides have been shown to inhibit cell growth and induce apoptosis in cancer cells, which has been highlighted as a possible mechanism of action for the anti-cancer properties of garlic extracts (Busch et al., Int J Oncol, 2010, 36, 743-9). If HS. radicals are formed during photodynamic irradiation of a photosensitizer (such as for example PpIX) in the presence of high concentrations of H$_2$S, it is possible that this could lead to cyclical generation of O$_2$-based radicals such as O$_2^{\cdot-}$, leading to an increased generation of damaging ROS, increasing cell killing.

As can be seen from Example 1, the mitochondrially-targeted SRHDs AP39-C8, AP39-C10, AP39-C12, AP123-C8, AP123-C10 or AP123-C12 proved surprisingly effective at increasing the efficacy of photosensitizer-based photodynamic cell killing, resulting in predominantly apoptotic cell death.

The compound A is a hydrogen sulfide releasing compound. In particular, the compound A comprises a group that is capable of releasing hydrogen sulfide. Typically, the group is capable of releasing hydrogen sulfide in vivo and/or in vitro. In general, the group undergoes a reaction in vivo and/or in vitro to generate H$_2$S and species derived from H$_2$S under physiological conditions, such as for example HS$^-$, sulfane sulfur, polysulfides, and/or S$^{2-}$. Additionally or alternatively, the group may undergo a reaction in vivo and/or in vitro to generate thiosulfate or sulfite.

Generally, the group is a moiety capable of releasing hydrogen sulfide that is linked, either directly or via a linker, to a mitochondrial targeting group. The mitochondrial targeting group can be attached at any convenient position on the compound that is capable of releasing hydrogen sulfide.

Compounds capable of releasing hydrogen sulfide are well known in the art, see for example G. Caliendo et al (J. Med. Chem., 2010, 53(17), 6275-6286). Examples of compounds capable of releasing hydrogen sulfide include N-acetyl-penicillamine, S-allyl-cysteine, bucillamine, carbocysteine, cysteamine, cystathionine, homocysteine, mecysteine, methionine, pantetheine, penicilla mine, penicillamine disulfide, thioacetic acid, thiodiglycolic acid, thioglycolic acid, thiolactic acid, 2-thiolhistidine, thiomalic acid, thiosalicylic acid, tiopronin, 5-(p-hydroxyphenyl)-3H-1,2-dithiol-3-thione, 1,3-dithiol-2-thione-5-carboxylic acid, 3-thioxo-3H-1,2-dithiole-5-carboxylic acid and 3-thioxo-3H-1,2-dithiole-4-carboxylic acid.

The group capable of releasing hydrogen sulfide can, for example, comprise a sulfide, a disulfide or a polysulfide moiety. Additionally or alternatively, the group capable of releasing hydrogen sulfide can, for example, comprise a persulfide, a thiosulfate or a perthiol.

In an embodiment, the group capable of releasing hydrogen sulfide comprises a thiocarbamoyl group, a 5-thioxo-5H-1,2-dithiol-3-yl group, a 5-thioxo-5H-1,2-dithiol-4-yl group, a 5-oxo-5H-1,2-dithiol-3-yl group, a 5-oxo-5H-1,2-dithiol-4-yl group, a 5-hydroxyimino-5H-1,2-dithiol-3-yl group, a 5-hydroxyimino-5H-1,2-dithiol-4-yl group, a phosphinodithioate group, a phosphinodithioic acid group, a thioketone group, or a thioaldehyde group.

In an embodiment, the group capable of releasing hydrogen sulfide comprises a thiocarbamoyl group or a 5-thioxo-5H-1,2-dithiol-3-yl group. Suitably, the thiocarbamoyl group may form part of a thiobenzamide group (thiobenzamidyl) in the compound A as a whole.

In an embodiment, the group capable of releasing hydrogen sulfide is selected from:

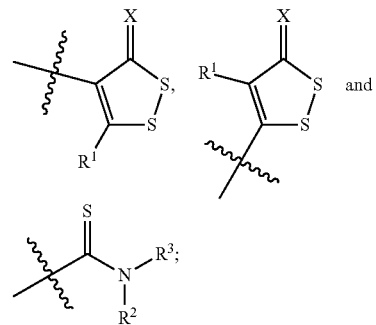

wherein:
X represents S, O or N—OH;
R$^1$, R$^2$ and R$^3$ each independently represent hydrogen, C$_{1-12}$ alkyl, C$_{1-12}$ alkoxy or C$_{6-10}$ aryl, wherein each C$_{1-12}$ alkyl, C$_{1-12}$ alkoxy or C$_{6-10}$ aryl group is unsubstituted or substituted by one or more substituents selected from a halogen atom, hydroxy, C$_{1-12}$ alkoxy, C$_{1-12}$ alkyl, hydroxy-C$_{1-12}$-alkyl, halo-C$_{1-12}$-alkyl and halo-C$_{1-12}$-alkoxy substituents.

In an embodiment, X is S or O. In an embodiment, X is S.

In an embodiment, R$^1$, R$^2$ and R$^3$ each independently represent hydrogen, C$_{1-12}$ alkyl, or C$_{1-12}$ alkoxy. In an embodiment, R$^1$, R$^2$ and R$^3$ each independently represent hydrogen, or C$_{1-12}$ alkyl. In an embodiment, R$^1$, R$^2$ and R$^3$ each independently represent hydrogen.

In an embodiment, the group capable of releasing hydrogen sulfide is:

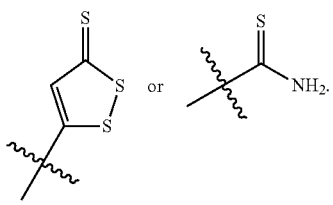

In an embodiment, the group capable of releasing hydrogen sulfide is:

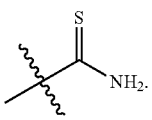

As can be seen from Example 1, mitochondrially targeted 4-HTB derivatives were found to sensitise A431 cells to photodynamic cell killing even more than the mitochondrially targeted ADT-OH derivatives.

A mitochondrial targeting group is a group which is capable of concentrating the compound in the mitochondria of a cell. For example, following incubation of a cell with a compound comprising a mitochondrial targeting group, the concentration of the compound in the mitochondria will be higher than the concentration of the compound in the cytosol. Mitochondrial targeting groups are well known and examples of appropriate mitochondrial targeting groups are discussed in Souza et al (Mitochondrion 5 (2005) 352-358), Kang et al (The Journal of Clinical Investigation, 119, 3, 454-464), Horton et al (Chemistry and Biology 15, 375-382), Wang et al (J. Med. Chem., 2007, 50 (21), 5057-5069), Souza et al (Journal of Controlled Release 92 (2003) 189-197), Maiti et al (Angew. Chem. Int. Ed., 2007, 46, 5880-5884), Kanai et al (Org. Biomol. Chem., 2007, 5, 307-309), Senkal et al (J Pharmacol Exp Ther., 317(3), 1188-1199), Weiss et al (Proc Natl Acad Sci USA, 84, 5444-5488), Zimmer et al (Br J Pharmacol., 1998, 123(6), 1154-8), Modica-Napolitano et al (Cancer Res., 1996, 56, 544-550), Murphy et al (Ann Rev. Pharm Toxicol., (2007), 47, 629-656), and Hoye et al (Accounts of Chemical Research, 41, 1, 87-97). All of these documents are incorporated by reference. For the avoidance of doubt, all of the mitochondrial targeting groups disclosed in these articles can be used in the compounds comprising a mitochondrial targeting group linked to a group capable of releasing hydrogen sulfide.

In an embodiment, the mitochondrial targeting group is a group which is capable of concentrating the compound specifically in the mitochondrial matrix of a cell.

In an embodiment, the mitochondrial targeting group is a lipophilic cation or a mitochondrial targeting peptide. In an embodiment, the lipophilic cation is a phosphonium cation, an arsonium cation, an ammonium cation, flupritine, MKT-077, a pyridinium ceramide, a quinolium, a liposomal cation, a sorbitol guanidine, a cyclic guanidine or a rhodamine.

Flupritine and MKT-077 are described in Zimmer et al. (Br J Pharmacol., 1998, 123(6), 1154-8) and Modica-Napolitano et al (Cancer Res., 1996, 56, 544-550). Mitochondrial targeting peptides are described in Horton et al (Chemistry and Biology, 2008, 15, 375-382) and Hoye et al (Accounts of Chemical Research, 2008, 41, 1, 87-97).

In an embodiment, the mitochondrial targeting group is a phosphonium cation. In an embodiment, the phosphonium cation has the formula:

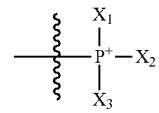

wherein X$_1$, X$_2$ and X$_3$ each independently represent C$_{1-12}$ alkyl, C$_{6-10}$ aryl, or C$_{1-12}$alkylene-C$_{6-10}$-aryl, wherein the alkyl and alkylene groups and moieties are unsubstituted or substituted by one or more, for example 1, 2 or 3, halogen atoms, hydroxyl, C$_{1-12}$ alkoxy or halo-C$_{1-12}$-alkoxy groups, and each aryl group or moiety is unsubstituted or substituted by one, two or three halogen atoms, hydroxyl, C$_{1-12}$ alkoxy or halo-C$_{1-12}$-alkoxy groups.

In an embodiment, each alkyl or alkylene group or moiety is unsubstituted or substituted by one or more, such as 1 or 2, halogen atoms. In an embodiment, the alkyl and/or alkylene group or moiety is unsubstituted.

In an embodiment, X$_1$, X$_2$ and X$_3$ are each a C$_{6-10}$ aryl group, for example a phenyl group. In an embodiment, X$_1$, X$_2$ and X$_3$ are the same.

In an embodiment, the mitochondrial targeting group is a triphenylphosphonium cation (TPP$^+$) of the formula:

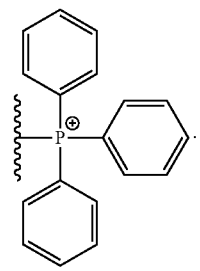 [SMILES: *[P+](c1ccccc1)(c1ccccc1)c1ccccc1]

The group capable of releasing hydrogen sulfide may be linked to one, two, three or more mitochondrial targeting groups. When the group capable of releasing hydrogen sulfide is linked to more than one mitochondrial targeting group, each mitochondrial targeting group can be the same or different. In an embodiment, the group capable of releasing hydrogen sulfide is linked to one mitochondrial targeting group.

In an embodiment, the mitochondrial targeting group is covalently linked to the group capable of releasing hydrogen sulfide.

The or each mitochondrial targeting group may be linked to the group capable of releasing hydrogen sulfide directly or via a linker. Where there is more than one mitochondrial targeting group, all of the mitochondrial targeting groups may be covalently linked directly to the group capable of releasing hydrogen sulfide or all of the mitochondrial targeting groups may be linked via a linker to the group capable of releasing hydrogen sulfide.

In an embodiment, there is one mitochondrial targeting group that is linked via a linker to the group capable of releasing hydrogen sulfide.

The linker may be any moiety capable of linking a mitochondrial targeting group to the group capable of releasing hydrogen sulfide.

The linker may have a molecular weight of 14 to 1000, such as 28 to 500, for example 44 to 300.

In an embodiment, the linker is a $C_{1-20}$ alkylene which is unsubstituted or substituted by one or more substituents selected from a halogen atom, hydroxy, $C_{1-12}$ alkoxy, $C_{1-12}$ alkyl, hydroxy-$C_{1-12}$-alkyl, halo-$C_{1-12}$-alkyl and a halo-$C_{1-12}$-alkoxy group, wherein zero or one to ten carbon atoms in the alkylene chain are replaced by spacer moieties selected from $C_{6-10}$ arylene, —O—, —S—, —NR$^4$—, —C(O)NR$^4$—, —NR$^4$C(O)—, —C(O)—, —OC(O)—, —C(O)O— moieties, wherein R$^4$ is hydrogen or $C_{1-12}$ alkyl and the $C_{6-10}$ arylene moiety is unsubstituted or substituted by one, two, three or four substituents selected from a halogen atom, hydroxy, $C_{1-12}$ alkyl and a $C_{1-12}$ alkoxy group.

In an embodiment, the spacer moieties are selected from $C_{6-10}$ arylene, —O—, —S—, —NR$^4$—, —C(O)NR$^4$—, —NR$^4$C(O)—, —C(O)—, —OC(O)—, —C(O)O— moieties. In an embodiment, the alkylene group consists of 1, 2, 3, 4 or 5 spacer moieties. In an embodiment, the alkylene group consists of 1 to 3 spacer moieties. In an embodiment, the alkylene group consists of 1 or 2 spacer moieties.

In an embodiment, the spacer moieties comprise 0 to 2 $C_{6-10}$ arylene, 0 to 2 —S—, 0 to 2 —O—, 0 to 2 —NR$^4$—, 0 to 2 —C(O)NR$^4$—, 0 to 2 —NR$^4$C(O)—, 0 to 2 —C(O)—, 0 to 2 —OC(O)—, and 0 to 2 —C(O)O— moieties.

In an embodiment, the linker comprises at least one $C_{6-10}$ arylene and at least one of the —OC(O)— or —C(O)O— spacer moieties.

In an embodiment, the alkylene group is a $C_{1-20}$ alkylene. In an embodiment, the alkylene group is a $C_{2-18}$ alkylene, such as a $C_{3-16}$ alkylene.

In an embodiment, the alkylene is a straight chain alkylene.

In an embodiment, the alkylene is unsubstituted or substituted by one or more, such as 1 or 2, halogen atoms. In an embodiment, said alkylene group is unsubstituted.

In an embodiment, the arylene spacer moiety is unsubstituted or substituted with one, two or three halogen atoms, hydroxy groups or $C_{1-12}$ alkyl groups. When the arylene spacer moiety carries 2 or more substituents, the substituents may be the same or different. In an embodiment, the arylene spacer moiety is unsubstituted.

In an embodiment, the arylene spacer moiety is a phenylene group, which is unsubstituted or substituted by one, two, three or four substituents selected from a halogen atom, hydroxy, $C_{1-12}$ alkyl and a $C_{1-12}$ alkoxy group.

In an embodiment, the linker is represented by the formula:

-L'-Y—Z— wherein:

L' represents a direct bond or a straight chain $C_{1-20}$ alkylene group, such as a straight chain $C_{2-18}$ alkylene group, which is unsubstituted or substituted by one or more substituents selected from a halogen atom, hydroxy, $C_{1-12}$ alkoxy, $C_{1-12}$ alkyl, hydroxy-$C_{1-12}$-alkyl, halo-$C_{1-12}$-alkyl and a halo-$C_{1-12}$-alkoxy group;

Y represents a direct bond, —OC(O)—, —C(O)O—, —O—, —C(O)NR$^4$— or —NR$^4$C(O)— wherein R$^4$ is hydrogen or $C_{1-12}$ alkyl;

Z represents a direct bond or a phenylene group, which is unsubstituted or substituted by one, two, three or four substituents selected from a halogen atom, hydroxy, $C_{1-12}$ alkyl and a $C_{1-12}$ alkoxy group.

In an embodiment, the alkylene group is unsubstituted or is substituted with one, two or three substituents selected from a halogen atom, hydroxy, $C_{1-12}$ alkoxy, $C_{1-12}$ alkyl. In an embodiment, the alkylene group is unsubstituted.

In an embodiment, L' is a straight chain alkylene group having the formula:

—(CH$_2$)$_n$— wherein n is an integer from 1 to 19.

In an embodiment, n is an integer from 2 to 19. In an embodiment, n is an integer from 2 to 18, from 2 to 17, from 2 to 16, from 2 to 15, from 2 to 14, from 2 to 13, from 2 to 12, from 2 to 11, from 3 to 19, from 3 to 17, from 3 to 16, from 3 to 15, from 3 to 14, from 3 to 13, from 3 to 12, from 3 to 11, from 4 to 19, from 4 to 17, from 4 to 16, from 4 to 15, from 4 to 14, from 4 to 13, from 4 to 12, from 4 to 11, from 5 to 19, from 5 to 17, from 5 to 16, from 5 to 15, from 5 to 14, from 5 to 13, from 5 to 12, from 5 to 11, from 6 to 19, from 6 to 17, from 6 to 16, from 6 to 15, from 6 to 14, from 6 to 13, from 6 to 12, from 6 to 11, from 7 to 19, from 7 to 17, from 7 to 16, from 7 to 15, from 7 to 14, from 7 to 13, from 7 to 12, or from 7 to 11. In an embodiment, n is 7, 9, or 11. In an embodiment, n is 11.

In an embodiment, Y is a direct bond, —OC(O)— or —C(O)O—. In an embodiment, Y is —OC(O)— or —C(O)O—. In an embodiment, Y is a —C(O)O— group.

In an embodiment, Z is a phenylene group.

In an embodiment, Z is a para-phenylene group.

In an embodiment, the moiety —Y—Z— has the formula:

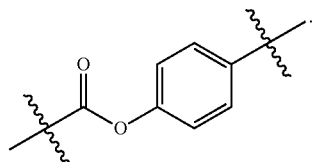 [SMILES: *C(=O)Oc1ccc(*)cc1]

In an embodiment, the compound A comprising a mitochondrial targeting group linked to a group capable of releasing hydrogen sulfide is represented by the formula:

MTG-L-Q wherein:

Q is a group capable of releasing hydrogen sulfide selected from:

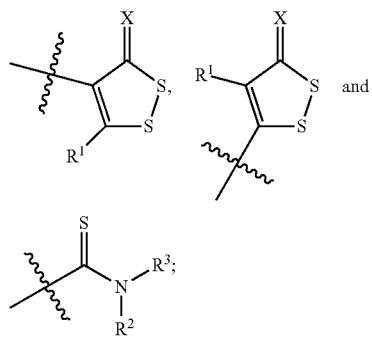

atom, hydroxy, $C_{1-12}$ alkoxy, $C_{1-12}$ alkyl, hydroxy-$C_{1-12}$-alkyl, halo-$C_{1-12}$-alkyl and a halo-$C_{1-12}$-alkoxy group, wherein zero or one to ten carbon atoms in the alkylene chain are replaced by spacer moieties selected from $C_{6-10}$ arylene, —O—, —S—, —NR$^4$—, —C(O)NR$^4$—, —NR$^4$C(O)—, —C(O)—, —OC(O)—, —C(O)O— moieties, wherein R$^4$ is hydrogen or $C_{1-12}$ alkyl and the $C_{6-10}$ arylene moiety is unsubstituted or substituted by one, two, three or four substituents selected from a halogen atom, hydroxy, $C_{1-12}$ alkyl and a $C_{1-12}$ alkoxy group; and MTG represent a mitochondrial targeting group, such as, for example, a phosphonium cation;

or a pharmaceutically acceptable salt thereof.

In the compounds that have the formula MTG-L-Q, the mitochondrial targeting group, the linker and the group capable of releasing hydrogen sulfide can be as defined above.

In an embodiment, the compound A comprises a cation selected from:

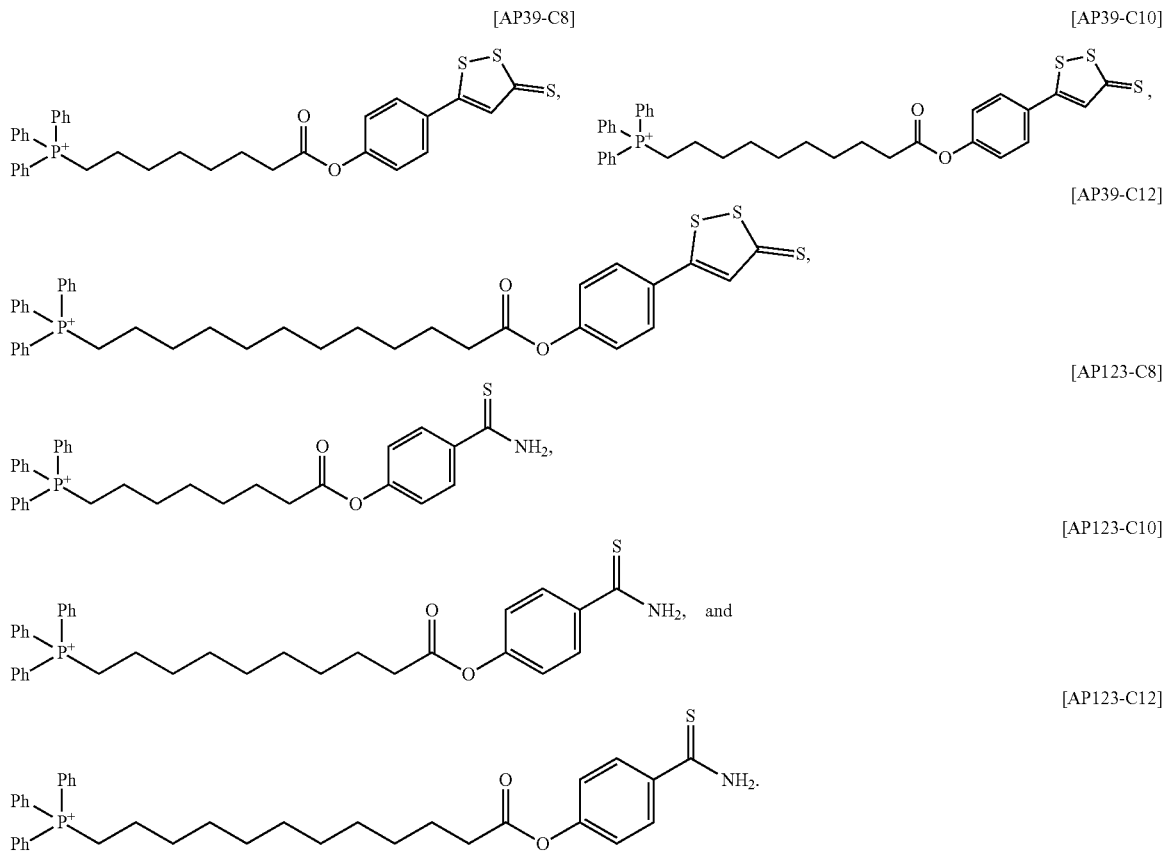

X represents S, O or N—OH;

R$^1$, R$^2$ and R$^3$ each independently represent hydrogen, $C_{1-12}$ alkyl, $C_{1-12}$ alkoxy or $C_{6-10}$ aryl, wherein each $C_{1-12}$ alkyl, $C_{1-12}$ alkoxy or $C_{6-10}$ aryl group is unsubstituted or substituted by one or more substituents selected from a halogen atom, hydroxy, $C_{1-12}$ alkoxy, $C_{1-12}$ alkyl, hydroxy-$C_{1-12}$-alkyl, halo-$C_{1-12}$-alkyl and halo-$C_{1-12}$-alkoxy substituents;

L represents a direct bond or a linker, wherein the linker is a $C_{1-20}$ alkylene which is unsubstituted or substituted by one or more substituents selected from a halogen In an embodiment, the compound comprising a mitochondrial targeting group linked to a group capable of releasing hydrogen sulfide comprises a cation having a structure as set out above and an anion that is a halogen (i.e. F$^-$, Cl$^-$ or Br$^-$). In an embodiment, the anion is a bromide anion.

The compounds comprising a mitochondrial targeting group linked to a group capable of releasing hydrogen sulfide can, for example, be prepared using the methods described in WO 2013/045951 or by routine modifications thereof, or by using conventional methods known in the art.

In an embodiment of the first aspect of the invention, the combination for use in photodynamic therapy comprises
(i) said inhibitor of the thioredoxin antioxidant system, or a pharmaceutically acceptable salt thereof or a prodrug thereof, and
(ii) said photosensitizer or photosensitizer precursor.

The term "inhibitors of the thioredoxin antioxidant system" comprises inhibitors of thioredoxin (Trx) and inhibitors of thioredoxin reductase.

In an embodiment, the inhibitor of the thioredoxin antioxidant system is a thioredoxin reductase inhibitor or a thioredoxin inhibitor.

In an embodiment, the inhibitor of the thioredoxin antioxidant system is a thioredoxin reductase inhibitor.

Thioredoxin reductase forms part of the thioredoxin antioxidant system; thioredoxin reductase enzymatically reduces the active site disulfide ($S_2$) of oxidised thioredoxin to a dithiol ($SH_2$).

Compounds which are known to inhibit thioredoxin reductase are called thioredoxin reductase inhibitors. Evidence has shown that low concentrations of some thioredoxin reductase inhibitors can effectively inhibit the thioredoxin system whilst maintaining cell viability (Cai et al., Free Radic Biol Med, 2012, 52, 257-65).

This embodiment of the first aspect of the invention is concerned with using thioredoxin reductase inhibitors in conjunction with a pro-oxidant treatment, namely photodynamic therapy. As can be seen from Example 2, the inventors have found that surprisingly, the use of a thioredoxin reductase inhibitor in combination with a photosensitizer precursor and irradiation significantly increased cell killing compared to a photosensitizer precursor only with irradiation (see FIG. 9).

In an embodiment, the thioredoxin reductase inhibitor is a gold-containing compound.

In an embodiment, the gold-containing compound comprises a gold atom linked to a sulfur atom.

In an embodiment, the gold-containing compound comprises a gold(I) complex.

In an embodiment, the gold-containing compound comprises a gold(I) thiolate. In an embodiment, the gold-containing compound comprises auranofin, aurothiomalate, aurothiosulfate, and/or aurothioglucose.

In an embodiment, the gold-containing compound is auranofin.

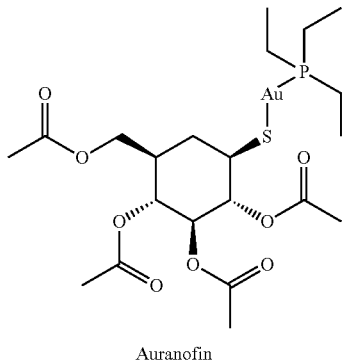

Auranofin

Auranofin (3,4,5-triacetyloxy-6-(acetyloxymethyl)oxane-2-thiolate; triethylphosphanium) is a potent thioredoxin reductase inhibitor. The organic gold compound was originally used to treat rheumatoid arthritis, effectively decreasing blood IgG levels and joint swelling (Finkelstein, A. E. et al., Annals of the Rheumatic Diseases, 1976, 35, 251-7). Inhibition of thioredoxin reductase by auranofin is thought to be due to its high reactivity with the active site selenocysteine, a property that is shared by many gold-containing compounds (Gromer, S. et al., J Biol Chem, 1998, 273, 20096-101).

In an embodiment, the gold-containing compound is sodium aurothiomalate or sodium aurothiosulfate.

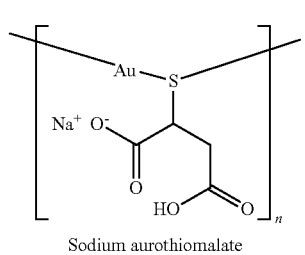

Sodium aurothiomalate

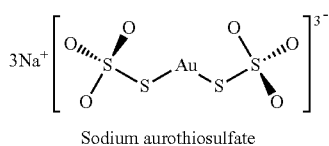

Sodium aurothiosulfate

In an embodiment, the gold-containing compound is aurothioglucose. Aurothioglucose is thought to exist as a polymer, but the polymerised structure has not yet been established. Speculative structures of aurothioglucose include:

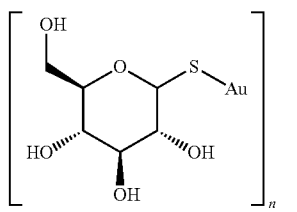

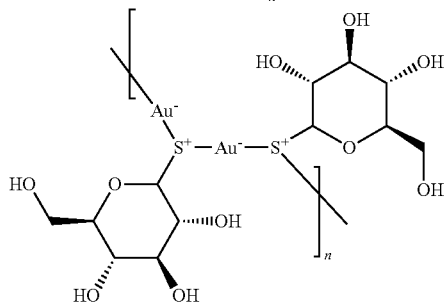

Aurothioglucose

In an embodiment, the thioredoxin reductase inhibitor is DNCB.

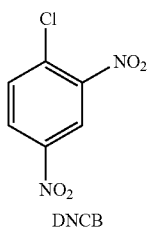

DNCB

DNCB (1-chloro-2,4-dinitrobenzene) is an alkylating agent, often used to deplete intracellular glutathione (GSH) levels, that was discovered to irreversibly inactivate thioredoxin reductase at low concentrations. Furthermore, this inactivation effect is in the region of 10,000-fold faster than the alkylation of GSH (Arner, E. S. et al., J Biol Chem, 1995, 270, 3479-82). Complete inactivation of 50 nM reduced thioredoxin reductase was achieved after 5 minutes incubation with 100 μM DNCB. This inactivation only occurred in the presence of NAD(P)H and persisted upon removal of DNCB. This persistence led to the theory that DNCB mediated inactivation of thioredoxin reductase was induced by alkylation of the active site thiols.

In an embodiment, the inhibitor of the thioredoxin antioxidant system is a thioredoxin inhibitor.

In an embodiment, the thioredoxin inhibitor is PX12.

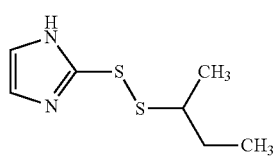

PX12

In an embodiment of the first aspect of the invention, the combination for use in photodynamic therapy comprises
(i) said nitroxide, or a pharmaceutically acceptable salt thereof or a prodrug thereof, and
(ii) said photosensitizer or photosensitizer precursor.

Nitroxides are known to be effective antioxidants which can protect against oxidative damage. For example, the nitroxide TEMPOL (4-hydroxy-2,2,6,6-tetra methylpiperidine 1-oxyl) has been studied as a protective agent against pro-oxidant doxorubicin-induced cardiac toxicity (Monti, E. et al., Free Radic Biol Med, 1996, 21, 463-70). In isolated rat hearts, TEMPOL was shown to significantly decrease the contractile impairment associated with doxorubicin toxicity. This was reflected by a decrease in oxidative damage, primarily lipid peroxidation. Derivatives of TEMPOL, OT-551 and OT-674 have also shown promise in the protection of light-induced retinal photoreceptor damage (Tanito, M. et al., Invest Ophthalmol Vis Sci, 2007, 48, 1900-5). Rats that had been treated with $H_2O$, OT-551 or OT-674 were exposed to 2700 lux white light for 6 hours. Retinal damage was evaluated histopathologically 5-7 days after exposure. Rats treated with $H_2O$ lost electroretinogram b-wave amplitudes and the retinal outer nuclear layer thickness was significantly decreased. Additionally, increased levels of 4-HNE were observed, which is known to cause lipid peroxidation and protein modification. TEMPOL derivatives OT-551 and OT-674 therefore significantly protected against light-induced damage in a dose-dependent manner and at the highest dose, OT-551 completely inhibited 4-HNE mediated protein modification.

This embodiment of the first aspect of the invention is concerned with using nitroxides in conjunction with a pro-oxidant treatment, namely photodynamic therapy. Despite the nitroxides' well-known protective effects, as can be seen from Example 3 the inventors have surprisingly found that the use of a nitroxide in combination with a photosensitizer precursor and irradiation did not have an inhibitory effect on photodynamic cell killing but instead significantly increased cell death compared to a photosensitizer precursor alone with irradiation (see FIG. 12).

Nitroxides can exist in three different oxidation states, namely in the nitroxide, oxoammonium cation or hydroxylamine form. The ability of nitroxides to efficiently undergo one-electron reductions has proven useful in the dismutation of $O_2^-$ and the reduction process is said to be SOD-mimetic (where SOD stands for superoxide dismutase), in that it is a catalytic reaction yielding the same products as SOD-mediated dismutation of $O_2^-$ (Krishna, M. C. et al., Proc Natl Acad Sci USA, 1992, 89, 5537-41). For example, shown below are the redox transformations between the nitroxide (top), oxoammonium cation (left) and hydroxylamine (right) oxidation states of TEMPO (2,2,6,6-tetramethyl-1-piperidinyloxy) and TEMPOL (4-hydroxy-TEMPO or 4-hydroxy-2,2,6,6-tetramethylpiperidine 1-oxyl), which are stable free radical cyclic nitroxides known to possess SOD-mimetic properties.

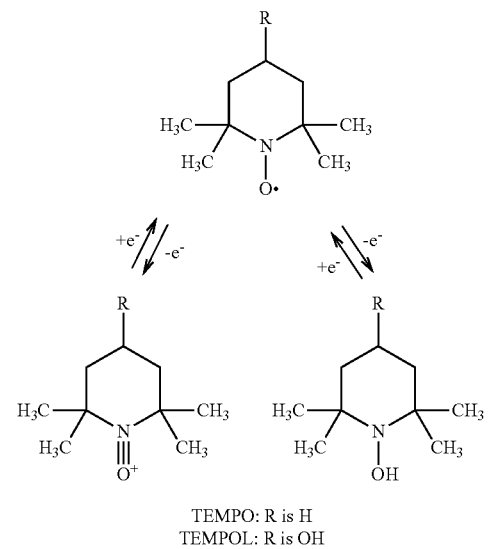

TEMPO: R is H
TEMPOL: R is OH

The SOD-mimetic properties are thought to contribute to the nitroxides' well-documented protective effects against oxidative damage.

Despite the nitroxides' well-known protective effects, as can be seen from Example 3, nitroxides proved surprisingly effective at increasing the efficacy of photosensitizer-based photodynamic cell killing.

In an embodiment, the nitroxide is optionally substituted TEMPO.

In an embodiment, the nitroxide is TEMPO optionally substituted in the 4-position.

In an embodiment, the nitroxide is a compound of the formula:

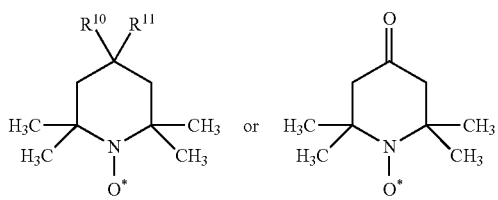

wherein

R[10] and R[11] are independently selected from —H, —OR[12], —OC(O)R[12], —C(O)OR[12], —C(O)R[12], —NR[12]R[13], —C(O)NR[12]R[13], —NR[12]C(O)R[13], —NCS, optionally substituted alkyl, optionally substituted cycloalkyl, optionally substituted alkenyl, optionally substituted alkynyl, optionally substituted aryl, optionally substituted heteroaryl, optionally substituted heterocyclyl, or a protecting group, or R[10] and R[11] may be joined together to form part of an optionally substituted cyclic group; and R[12] and R[13] are independently selected from —H, optionally substituted alkyl, optionally substituted cycloalkyl, optionally substituted alkenyl, optionally substituted alkynyl, optionally substituted aryl, optionally substituted heteroaryl, optionally substituted heterocyclyl, or alkoxyl, or R[12] and R[13] may be joined together to form part of an optionally substituted cyclic group.

In an embodiment, at least one of R[10] and R[11] is —H.

In an embodiment, the nitroxide is any one of the following compounds:

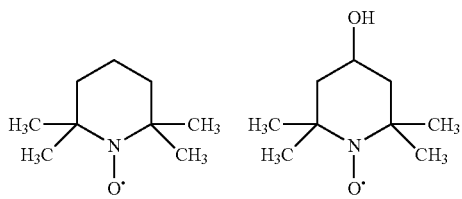

TEMPO  TEMPOL

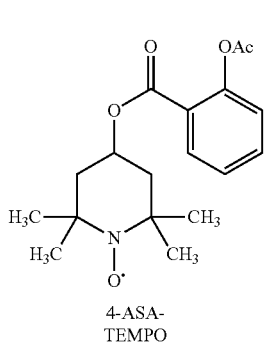

4-ASA-TEMPO

-continued

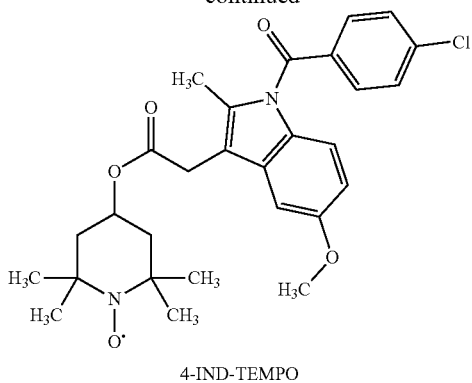

4-IND-TEMPO

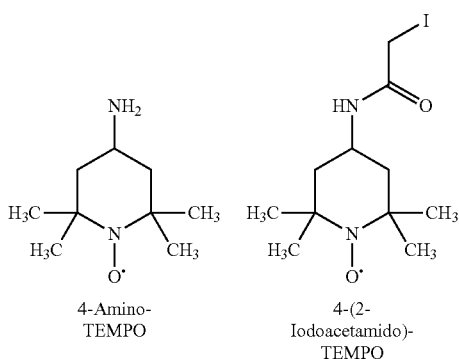

4-Amino-TEMPO    4-(2-Iodoacetamido)-TEMPO

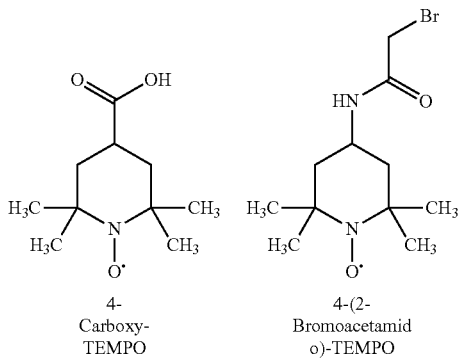

4-Carboxy-TEMPO    4-(2-Bromoacetamido)-TEMPO

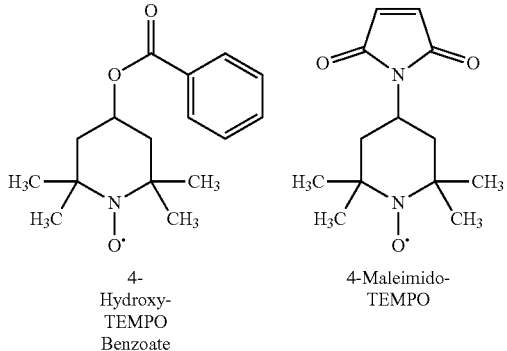

4-Hydroxy-TEMPO Benzoate    4-Maleimido-TEMPO

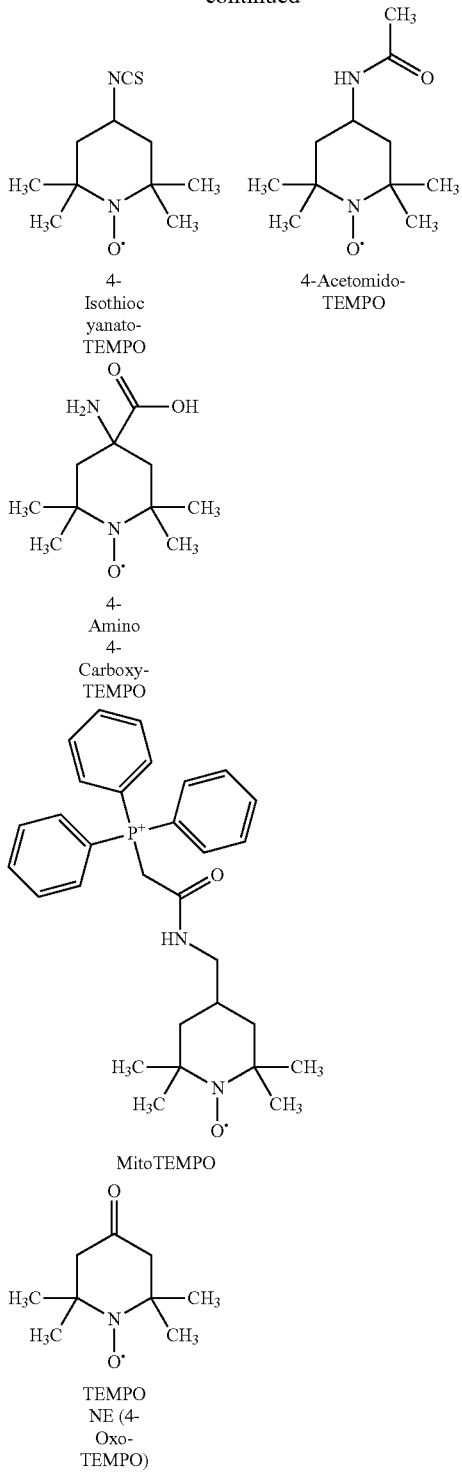

4-Isothiocyanato-TEMPO

4-Acetomido-TEMPO

4-Amino 4-Carboxy-TEMPO

MitoTEMPO

TEMPONE (4-Oxo-TEMPO)

In an embodiment, the nitroxide is TEMPO or TEMPOL.

In an embodiment, the combination for use in photodynamic therapy comprises a prodrug of the nitroxide. In an embodiment, the prodrug is a nitrone.

In an embodiment of the first aspect of the invention, the photosensitizer or photosensitizer precursor is a photosensitizer precursor. In an embodiment, the photosensitizer precursor comprises a precursor of protoporphyrin IX (PpIX). In an embodiment, the photosensitizer precursor comprises aminolaevulinic acid (ALA), methyl aminolaevulinate (MAL), and/or hexyl aminolaevulinate (HAL). In an embodiment, the photosensitizer precursor comprises methyl aminolaevulinate (MAL).

In an embodiment, the photosensitizer or photosensitizer precursor is a photosensitizer. In an embodiment, the photosensitizer comprises protoporphyrin IX (PpIX).

In an embodiment of the first aspect of the invention, the combination comprising the components (i) and (ii) is for use in treating a medical condition which is responsive to photodynamic therapy. In an embodiment, the combination is for use in treating a condition, which is caused by and/or exacerbated by the abnormal proliferation of cells, by photodynamic therapy. In an embodiment, the combination is for use in treating cancer, by photodynamic therapy.

In an embodiment, the combination comprising the components (i) and (ii) is for use in treating scleroderma, lichen sclerosus, psoriasis or warts, by photodynamic therapy. In an embodiment, the combination is for use in treating chronic wounds, by photodynamic therapy. Such chronic wounds may, for example, be leg ulcers in the elderly. In an embodiment, the combination is for use in treating acne, by photodynamic therapy. In an embodiment, the combination is for use in treating a microbial infection, by photodynamic therapy. Such a microbial infection may, for example, be caused by bacteria, fungi, viruses and/or yeasts. In an embodiment, the combination is for use in treating a parasitic infestation, by photodynamic therapy. In an embodiment, the combination is for use in treating rheumatoid arthritis, by photodynamic therapy. In an embodiment, the combination is for use in bone marrow purging, by photodynamic therapy, in the treatment of leukaemia. In an embodiment, the combination is for use in treating pulmonary fibrosis, by photodynamic therapy. In an embodiment, the combination is for use in treating restenosis, by photodynamic therapy.

In an embodiment, the combination comprising the components (i) and (ii) for use according to the first aspect of the invention is administered topically. In an embodiment, the combination is administered orally. In an embodiment, the combination is administered intravenously. In an embodiment, the combination is administered intraperitoneally. In an embodiment, the combination is administered intradermally. In an embodiment, the combination is administered intra-articularly.

According to a second aspect of the invention there is provided the use of a combination comprising (i) a compound A comprising a mitochondrial targeting group linked to a group capable of releasing hydrogen sulfide or a pharmaceutically acceptable salt thereof or a prodrug thereof, an inhibitor of the thioredoxin antioxidant system or a pharmaceutically acceptable salt thereof or a prodrug thereof, and/or a nitroxide or a pharmaceutically acceptable salt thereof or a prodrug thereof; and (ii) a photosensitizer or photosensitizer precursor, in photodynamic treatment for cosmetic purposes.

In an embodiment, the inhibitor of the thioredoxin antioxidant system is a thioredoxin reductase inhibitor or a thioredoxin inhibitor. In an embodiment, the inhibitor of the thioredoxin antioxidant system is a thioredoxin reductase inhibitor. In an embodiment, the inhibitor of the thioredoxin antioxidant system is a thioredoxin inhibitor.

In an embodiment of the second aspect of the invention, the combination comprises (i) the compound A comprising a mitochondrial targeting group linked to a group capable of releasing hydrogen sulfide, or a pharmaceutically acceptable salt thereof or a prodrug thereof, and (ii) the photosensitizer or photosensitizer precursor. In an embodiment, the compound A is as described for the first aspect of the invention and/or the photosensitizer or photosensitizer precursor is as described for the first aspect of the invention.

In an embodiment of the second aspect of the invention, the combination comprises (i) the inhibitor of the thioredoxin antioxidant system, or a pharmaceutically acceptable salt thereof or a prodrug thereof, and (ii) the photosensitizer or photosensitizer precursor. In an embodiment, the inhibitor of the thioredoxin antioxidant system is as described for the first aspect of the invention and/or the photosensitizer or photosensitizer precursor is as described for the first aspect of the invention.

In an embodiment of the second aspect of the invention, the combination comprises (i) the nitroxide, or a pharmaceutically acceptable salt thereof or a prodrug thereof, and (ii) the photosensitizer or photosensitizer precursor. In an embodiment, the nitroxide is as described for the first aspect of the invention and/or the photosensitizer or photosensitizer precursor is as described for the first aspect of the invention.

In an embodiment of the second aspect of the invention, the combination is used in the photodynamic treatment for cosmetic purposes of hypertrophic scars, acne scars, wrinkles (rhytides), actinically damaged skin (also known as photodamaged skin or sun damaged skin), rosacea, actinic keratosis, sebaceous gland hyperplasia, lentigines, hirsutism, telangiectasias, port wine stains, erythema, poikiloderma, melisma, dyschromia, hyperpigmentation, mottled or blotchy pigmentation, rough skin patches, poor skin texture, enlarged pores, and/or skin laxity. In an embodiment, the combination is used in cosmetic photorejuvenation of skin by photodynamic treatment.

According to a third aspect of the invention there is provided a method of treatment of a human or animal patient suffering from or at risk of suffering from a condition which is caused by and/or exacerbated by the abnormal proliferation of cells, the method involving administering to the patient a therapeutically effective amount of a combination comprising (i) a compound A comprising a mitochondrial targeting group linked to a group capable of releasing hydrogen sulfide or a pharmaceutically acceptable salt thereof or a prodrug thereof, an inhibitor of the thioredoxin antioxidant system or a pharmaceutically acceptable salt thereof or a prodrug thereof, and/or a nitroxide or a pharmaceutically acceptable salt thereof or a prodrug thereof; and (ii) a photosensitizer or photosensitizer precursor; and exposing a region of the patient containing the combination to light as part of a photodynamic therapy.

In an embodiment, the inhibitor of the thioredoxin antioxidant system is a thioredoxin reductase inhibitor or a thioredoxin inhibitor. In an embodiment, the inhibitor of the thioredoxin antioxidant system is a thioredoxin reductase inhibitor. In an embodiment, the inhibitor of the thioredoxin antioxidant system is a thioredoxin inhibitor.

In an embodiment of the third aspect of the invention, the combination comprises (i) the compound A comprising a mitochondrial targeting group linked to a group capable of releasing hydrogen sulfide, or a pharmaceutically acceptable salt thereof or a prodrug thereof, and (ii) the photosensitizer or photosensitizer precursor. In an embodiment, the compound A is as described for the first aspect of the invention and/or the photosensitizer or photosensitizer precursor is as described for the first aspect of the invention.

In an embodiment of the third aspect of the invention, the combination comprises (i) the inhibitor of the thioredoxin antioxidant system, or a pharmaceutically acceptable salt thereof or a prodrug thereof, and (ii) the photosensitizer or photosensitizer precursor. In an embodiment, the inhibitor of the thioredoxin antioxidant system is as described for the first aspect of the invention and/or the photosensitizer or photosensitizer precursor is as described for the first aspect of the invention.

In an embodiment of the third aspect of the invention, the combination comprises (i) the nitroxide, or a pharmaceutically acceptable salt thereof or a prodrug thereof, and (ii) the photosensitizer or photosensitizer precursor. In an embodiment, the nitroxide is as described for the first aspect of the invention and/or the photosensitizer or photosensitizer precursor is as described for the first aspect of the invention.

According to a fourth aspect of the invention there is provided a composition comprising (i) a compound A comprising a mitochondrial targeting group linked to a group capable of releasing hydrogen sulfide or a pharmaceutically acceptable salt thereof or a prodrug thereof, an inhibitor of the thioredoxin antioxidant system or a pharmaceutically acceptable salt thereof or a prodrug thereof, and/or a nitroxide or a pharmaceutically acceptable salt thereof or a prodrug thereof; and (ii) a photosensitizer or photosensitizer precursor.

In an embodiment, the inhibitor of the thioredoxin antioxidant system is a thioredoxin reductase inhibitor or a thioredoxin inhibitor. In an embodiment, the inhibitor of the thioredoxin antioxidant system is a thioredoxin reductase inhibitor. In an embodiment, the inhibitor of the thioredoxin antioxidant system is a thioredoxin inhibitor.

In an embodiment of the fourth aspect of the invention, the combination comprises (i) the compound A comprising a mitochondrial targeting group linked to a group capable of releasing hydrogen sulfide, or a pharmaceutically acceptable salt thereof or a prodrug thereof, and (ii) the photosensitizer or photosensitizer precursor. In an embodiment, the compound A is as described for the first aspect of the invention and/or the photosensitizer or photosensitizer precursor is as described for the first aspect of the invention.

In an embodiment of the fourth aspect of the invention, the combination comprises (i) the inhibitor of the thioredoxin antioxidant system, or a pharmaceutically acceptable salt thereof or a prodrug thereof, and (ii) the photosensitizer or photosensitizer precursor. In an embodiment, the inhibitor of the thioredoxin antioxidant system is as described for the first aspect of the invention and/or the photosensitizer or photosensitizer precursor is as described for the first aspect of the invention.

In an embodiment of the fourth aspect of the invention, the combination comprises (i) the nitroxide, or a pharmaceutically acceptable salt thereof or a prodrug thereof, and (ii) the photosensitizer or photosensitizer precursor. In an embodiment, the nitroxide is as described for the first aspect of the invention and/or the photosensitizer or photosensitizer precursor is as described for the first aspect of the invention.

In an embodiment of the fourth aspect of the invention, the composition is a pharmaceutical composition which further comprises a pharmaceutically acceptable carrier. In an embodiment, components (i) and (ii) are present in the composition in a pharmaceutically effective amount. Throughout this specification, the term "pharmaceutical" includes veterinary. In an embodiment, the composition is a topical skin treatment formulation.

According to a fifth aspect of the invention there is provided a compound A comprising a mitochondrial targeting group linked to a group capable of releasing hydrogen sulfide or a pharmaceutically acceptable salt thereof or a prodrug thereof, for use in photodynamic therapy for the purpose of enhancing cell death, wherein the photodynamic therapy comprises the use of a combination of the compound A or a pharmaceutically acceptable salt thereof or a prodrug thereof and a photosensitizer or a photosensitizer precursor. In an embodiment, the compound A is as described for the first aspect of the invention and/or the photosensitizer or photosensitizer precursor is as described for the first aspect of the invention.

According to a sixth aspect of the invention there is provided an inhibitor of the thioredoxin antioxidant system or a pharmaceutically acceptable salt thereof or a prodrug thereof, for use in photodynamic therapy for the purpose of enhancing cell death, wherein the photodynamic therapy comprises the use of a combination of the inhibitor of the thioredoxin antioxidant system or a pharmaceutically acceptable salt thereof or a prodrug thereof and a photosensitizer or a photosensitizer precursor. In an embodiment, the inhibitor of the thioredoxin antioxidant system is as described for the first aspect of the invention and/or the photosensitizer or photosensitizer precursor is as described for the first aspect of the invention.

In an embodiment, the inhibitor of the thioredoxin antioxidant system is a thioredoxin reductase inhibitor or a thioredoxin inhibitor. In an embodiment, the inhibitor of the thioredoxin antioxidant system is a thioredoxin reductase inhibitor. In an embodiment, the inhibitor of the thioredoxin antioxidant system is a thioredoxin inhibitor.

According to a seventh aspect of the invention there is provided a nitroxide or a pharmaceutically acceptable salt thereof or a prodrug thereof, for use in photodynamic therapy for the purpose of enhancing cell death, wherein the photodynamic therapy comprises the use of a combination of the nitroxide or a pharmaceutically acceptable salt thereof or a prodrug thereof and a photosensitizer or a photosensitizer precursor. In an embodiment, the nitroxide is as described for the first aspect of the invention and/or the photosensitizer or photosensitizer precursor is as described for the first aspect of the invention.

For the avoidance of doubt, in the second, third, fourth, fifth, sixth and seventh aspects of the invention, the compound A, the inhibitor of the thioredoxin antioxidant system, the nitroxide and/or the photosensitizer or photosensitizer precursor can be as defined above for the first aspect of the invention.

Definitions

It is to be understood that the wavy line in any chemical structures or moieties represented herein, such as shown below, indicates the point of attachment of that structure or moiety.

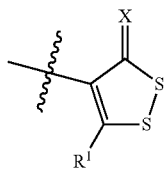

Any reference to groups or compounds for "releasing" or that are capable of "releasing" hydrogen sulfide as used herein refers to a group or a compound that undergoes a chemical reaction, e.g. in vivo and/or in vitro, to produce $H_2S$, $HS^-$, $S^{2-}$ and/or further derived species such as for example sulfane sulfur and/or polysulfides. Additionally or alternatively, the group may undergo a reaction in vivo and/or in vitro to generate thiosulfate or sulfite. In aqueous solution, $H_2S$ dissociates to form two dissociation states; the hydrosulfide anion ($HS^-$) and the sulfide anion ($S^{2-}$). The group or compound may therefore produce $H_2S$, $HS^-$, $S^{2-}$, sulfane sulfur and/or polysulfides, depending on the surrounding physiological conditions. Additionally or alternatively, the group may produce thiosulfate or sulfite.

The compound A comprising a mitochondrial targeting group linked to a group capable of releasing hydrogen sulfide and/or the inhibitor of the thioredoxin antioxidant system (for example a thioredoxin reductase inhibitor) may be present in the form of a pharmaceutically acceptable salt. Prodrugs of the compound A comprising a mitochondrial targeting group linked to a group capable of releasing hydrogen sulfide, the inhibitor of the thioredoxin antioxidant system (for example a thioredoxin reductase inhibitor) and/or the nitroxide may also be present in the form of a pharmaceutically acceptable salt. For use in pharmaceutical compositions, the salts of the compounds refer to non-toxic "pharmaceutically acceptable salts". Examples of pharmaceutically acceptable salts are discussed in Berge et al (J. Pharm. Sci., 1977, 66, 1-19).

Pharmaceutically acceptable salt forms include pharmaceutically acceptable acidic/anionic or basic/cationic salts.

Examples of pharmaceutically acceptable acidic/anionic salts include acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate, and triethiodide salts.

Examples of pharmaceutically acceptable basic/cationic salts include sodium, potassium, calcium, magnesium, diethanolamine, N-methyl-D-glucamine, L-lysine, L-arginine, ammonium, ethanolamine, piperazine and triethanolamine salts.

If the compound is anionic, or has a functional group which may be anionic, then a salt may be formed with a suitable cation. Examples of suitable inorganic cations include alkali metal ions, such as $Na^+$ and $K^+$, alkaline earth cations, such as $Ca^{2+}$ and $Mg^{2+}$, and other cations such as $Al^{3+}$. Examples of suitable organic cations include ammonium ion (i.e., $NH_4^+$) and substituted ammonium ions (e.g. $NH_3R^+$, $NH_2R_2^+$, $NHR_3^+$, $NR_4^+$, where R is an alkyl group).

If the compound is cationic, or has a functional group which may be cationic, then a salt may be formed with a suitable anion. Examples of suitable inorganic anions include those derived from the following inorganic acids: hydrochloric, hydrobromic, hydroiodic, sulfuric, sulfurous, nitric, nitrous, phosphoric, and phosphorous. Examples of suitable organic anions include those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, gluchheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric.

If the compound has both a cationic functional group, or a functional group that can become cationic, and an anionic functional group, or a functional group that can become anionic, then the compound may be present as a zwitterion.

The compound A comprising a mitochondrial targeting group linked to a group capable of releasing hydrogen sulfide, the inhibitor of the thioredoxin antioxidant system (for example a thioredoxin reductase inhibitor) and/or the nitroxide may be present in the form of a prodrug. A prodrug of a compound is a form of the compound which can be converted to the compound in vivo, for example through a normal metabolic process.

The term "hydrogen" or "hydrogen atom" as used herein refers to a —H moiety.

The term "halogen" or "halogen atom" as used herein refers to a —F, —Cl, —Br or —I moiety.

The term "hydroxy" as used herein refers to an —OH moiety.

The term "alkyl" as used herein refers to a monovalent moiety obtained by removing a hydrogen atom from a carbon atom of a hydrocarbon compound having from 1 to 12 carbon atoms (unless otherwise specified), which may be aliphatic or alicyclic, which may be saturated or unsaturated (e.g. partially unsaturated or fully unsaturated), and which may be linear or branched. Thus, the term "alkyl" includes the sub-classes alkenyl, alkynyl, cycloalkyl, cycloalkenyl and cycloalkynyl below.

In the context of alkyl groups, the prefix $C_{1-12}$ denotes the number of carbon atoms, or range of number of carbon atoms present in that group. Thus, the term "$C_{1-12}$ alkyl" refers to an alkyl group having from 1 to 12 carbon atoms. The first prefix may vary according to the nature of the alkyl group. Thus, if the alkyl group is an alkenyl or alkynyl group, then the first prefix must be at least 2 (e.g. $C_{2-12}$). For cyclic (e.g. cycloalkyl, cycloalkenyl, cycloalkynyl) or branched alkyl groups, the first prefix must be at least 3 (e.g. $C_{3-12}$).

Examples of saturated alkyl groups include methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$) and decyl ($C_{10}$). Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$). Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

The term "alkenyl" refers to an alkyl group having one or more carbon-carbon double bonds. Examples of unsaturated alkenyl groups include ethenyl (vinyl, —CH=CH$_2$), 1-propenyl (—CH=CH—CH$_3$) and 2-propenyl (allyl, —CH—CH=CH$_2$).

The term "alkynyl" refers to an alkyl group having one or more carbon-carbon triple bonds. Examples of unsaturated alkynyl groups include, but are not limited to, ethynyl (ethinyl, —C≡CH) and 2-propynyl (propargyl, —CH$_2$—C≡CH).

The term "cycloalkyl" refers an alkyl group which is also a cyclyl group; that is, a monovalent moiety obtained by removing a hydrogen atom from an alicyclic ring atom of a carbocyclic compound (i.e. a compound where all of the ring atoms are carbon atoms). The ring may be saturated or unsaturated (e.g. partially unsaturated or fully unsaturated), which moiety has from 3 to 12 carbon atoms (unless otherwise specified). Thus, the term "cycloalkyl" includes the sub-classes cycloalkenyl and cycloalkynyl. In an embodiment, each ring has from 3 to 7 ring carbon atoms. Examples of cycloalkyl groups include those derived from (i) saturated monocyclic hydrocarbon compounds: cyclopropane ($C_3$), cyclobutane ($C_4$), cyclopentane ($C_5$), cyclohexane ($C_6$), cycloheptane ($C_7$) and methylcyclopropane ($C_4$); (ii) unsaturated monocyclic hydrocarbon compounds: cyclopropene ($C_3$), cyclobutene ($C_4$), cyclopentene ($C_5$), cyclohexene ($C_6$), methylcyclopropene ($C_4$) and dimethyl-cyclopropene ($C_5$); (iii) saturated polycyclic hydrocarbon compounds: thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin ($C_{10}$); (iv) unsaturated polycyclic hydrocarbon compounds: camphene ($C_{10}$), limonene ($C_{10}$), pinene ($C_{10}$); and (v) polycyclic hydrocarbon compounds having an aromatic ring: indene ($C_9$), indane ($C_9$) and tetraline ($C_{10}$).

In an embodiment, a reference to an alkyl group described herein is a $C_{1-12}$ alkyl group, such as a $C_{1-8}$ alkyl group, for example a $C_{1-6}$ alkyl group, or a $C_{1-4}$ alkyl group. The alkyl groups in the invention can be saturated alkyl groups or saturated cycloalkyl groups, for example saturated, unbranched alkyl groups.

The phrase "optionally substituted" as used herein refers to a parent group which may be unsubstituted or which may be substituted with one or more, for example one or two, substituents. The substituents on an "optionally substituted" group may for example be selected from alkyl, cycloalkyl, alkenyl, alkynyl, aryl, heteroaryl and heterocyclyl groups; carboxylic acids and carboxylate ions; carboxylate esters; carbamates; alkoxyl groups; ketone and aldehyde groups; amine and amide groups; —OH; —CN; —NO$_2$; and halogens.

The term "substituents" is used herein in the conventional sense and refers to a chemical moiety, which is covalently attached to, or if appropriate, fused to, a parent group.

The term "aryl" as used herein refers to a monovalent moiety obtained by removing a hydrogen atom from an aromatic ring atom of an aromatic compound, which moiety has from 6 to 10 ring carbon atoms (unless otherwise specified). In an embodiment, the aryl group is a phenyl group.

The term "heteroaryl" as used herein refers to a monovalent moiety obtained by removing a hydrogen atom from a heteroaromatic compound, which moiety may for example be a monocyclic or bicyclic group. The heteroaryl moiety may contain from 1 to 12 carbon atoms (unless otherwise specified) and one or more N, O or S atoms. The heteroaryl moiety may be a 5 or 6-membered ring containing one or more N atoms.

The term "heterocyclyl" as used herein refers to a monovalent moiety obtained by removing a hydrogen atom from a ring atom of a heterocyclic compound, which moiety may for example be a monocyclic or bicyclic group. The heterocyclyl group may contain from 1 to 12 carbon atoms (unless otherwise specified) and one or more N, O or S atoms.

The term "alkoxy" used herein refers to an alkyl-oxy group, where the alkyl group is as defined above and has from 1 to 12 carbon atoms (unless otherwise specified). In an embodiment, the alkyl moiety in an alkoxy group is a saturated alkyl group or a saturated cycloalkyl group. In an embodiment, the alkyl moiety is a saturated, unbranched alkyl group. Examples of $C_{1-12}$ alkoxy groups include —OMe (methoxy), —OEt (ethoxy), —O($^n$Pr) (n-propoxy), —O($^i$Pr) (isopropoxy), —O($^n$Bu) (n-butoxy), —O($^s$Bu) (sec-butoxy), —O($^i$Bu) (isobutoxy), and —O($^t$Bu) (tert-butoxy).

The term "alkylene" as used herein refers to a bidentate moiety obtained by removing two hydrogen atoms, either both from the same carbon atom, or one from each of two different carbon atoms, of a hydrocarbon compound having from 1 to 20 carbon atoms (unless otherwise specified), which may be aliphatic or alicyclic, and which may be saturated, partially unsaturated, or fully unsaturated. Thus, the term "alkylene" includes the sub-classes alkenylene, alkynylene, cycloalkylene as discussed below. The prefix (e.g. $C_{1-4}$, $C_{1-7}$, $C_{1-20}$) denotes the number of carbon atoms, or a range for the number of carbon atoms. For example, the term "$C_{1-20}$alkylene" used herein, refers to an alkylene group having from 1 to 20 carbon atoms.

Examples of linear saturated $C_{1-20}$alkylene groups include —$(CH_2)_n$— where n is an integer from 1 to 20, such as —$CH_2$— (methylene), —$CH_2CH_2$— (ethylene), —$CH_2CH_2CH_2$— (propylene), and —$CH_2CH_2CH_2CH_2$— (butylene). Examples of branched saturated $C_{1-20}$alkylene groups include —$CH(CH_3)$—, —$CH(CH_3)CH_2$—, and —$CH(CH_3)CH_2CH_2$—. Examples of linear partially unsaturated $C_{2-20}$alkylene groups include —CH=CH— (vinylene), —CH=CHCH$_2$—, —CH$_2$—CH=CH$_2$—, and —CH=CHCH$_2$CH$_2$—. Examples of branched partially unsaturated $C_{1-20}$alkylene groups include —C(CH$_3$)=CH—, —C(CH$_3$)=CHCH$_2$— and —CH=CHCH(CH$_3$)—. Examples of alicyclic saturated $C_{3-20}$alkylene groups include cyclopentylene (e.g. cyclopent-1,3-ylene) and cyclohexylene (e.g. cyclohex 1,4 ylene). Examples of alicyclic partially unsaturated $C_{2-20}$alkylene groups include cyclopentenylene (e.g. 4-cyclopenten-1,3-ylene), cyclohexenylene (e.g. 2 cyclohexen-1,4-ylene; 3 cyclohexen-1,2-ylene; 2,5 cyclohexadien-1,4-ylene).

In an embodiment, a reference to an alkylene group described herein is a $C_{1-20}$alkylene group, such as a $C_{1-12}$alkylene group, for example a $C_{2-8}$alkylene group, or a $C_{3-7}$alkylene group. In an embodiment, the alkylene groups can be saturated alkyl groups or saturated cycloalkyl groups, such as saturated, unbranched alkyl groups (i.e. straight chain alkylene group).

The term "arylene" as used herein refers to a bidentate moiety obtained by removing two hydrogen atoms, one from each of two different aromatic ring atoms of an aromatic compound, which moiety has from 6 to 10 ring atoms (unless otherwise specified). In an embodiment, each ring has from 6 to 8 ring atoms. In this context, the prefix (e.g. $C_{6-10}$) denotes the number of ring atoms, or a range for the number of ring carbon atoms.

In some embodiments, substituents can themselves be substituted. For example, a $C_{1-12}$alkyl group may be substituted with, for example, hydroxy (referred to as a hydroxy-$C_{1-12}$alkyl group) or a halogen atom (referred to as a halo-$C_{1-12}$alkyl group), and a $C_{1-12}$alkoxy group may be substituted with, for example, a halogen atom (referred to as a halo-$C_{1-12}$alkoxy group).

The term "alkylene-arylene" used herein refers to a bidentate moiety comprising an alkylene moiety, -alkylene-, linked to an arylene moiety, -arylene-, that is, -alkylene-arylene-. Examples of alkylene-arylene groups include $C_{1-20}$alkylene-$C_{6-10}$arylene, such as methylene-phenylene, ethylene-phenylene, propylene-phenylene, and ethenylene-phenylene (also known as vinylene-phenylene).

The term "phosphinodithioate" as used herein refers to a >P(S)S$^-$ group.

The term "phosphinodithioic acid" as used herein refers to a >P(S)SH group.

The term "protecting group" as used herein refers to a group capable of protecting a heteroatom (such as an oxygen atom), which protecting group may, subsequent to the reaction for which protection is employed, be removed without disturbing the remainder of the molecule. Protecting groups are well known and listed in standard texts such as Kocienski P. J., Protecting Groups, 3rd ed., Georg Thieme Verlag, New York, 2005; and Greene T. W., Wuts P. G. M., Protective Groups In Organic Synthesis, 3rd ed., John Wiley & Sons, New York, 1998.

Certain compounds may exist in one or more particular geometric, enantiomeric, diasteriomeric, tautomeric, or conformational forms. Unless otherwise specified, a reference to a particular compound includes all such isomeric forms, including (wholly or partially) racemic and other mixtures thereof. Methods for the preparation and separation of such isomeric forms are either known in the art.

Throughout the description and claims of this specification, the words "comprise" and "contain" and variations of the words, for example "comprising" and "comprises", mean "including but not limited to", and do not exclude other moieties, additives, components, integers or steps. Moreover the singular encompasses the plural unless the context otherwise requires: in particular, where the indefinite article is used, the specification is to be understood as contemplating plurality as well as singularity, unless the context requires otherwise.

Preferred features of each aspect of the invention may be as described in connection with any of the other aspects. Other features of the invention will become apparent from the following examples. Generally speaking the invention extends to any novel one, or any novel combination, of the features disclosed in this specification (including any accompanying claims and drawings). Thus features, integers, characteristics, compounds, chemical moieties or groups described in conjunction with a particular aspect, embodiment or example of the invention are to be understood to be applicable to any other aspect, embodiment or example described herein unless incompatible therewith. Moreover unless stated otherwise, any feature disclosed herein may be replaced by an alternative feature serving the same or a similar purpose.

Where upper and lower limits are quoted for a property, then a range of values defined by a combination of any of the upper limits with any of the lower limits may also be implied.

In this specification, references to compound properties are—unless stated otherwise—to properties measured under ambient conditions, i.e. at atmospheric pressure and at a temperature of from 16 to 22 or 25° C., or from 18 to 22 or 25° C., for example about 20° C. or about 25° C.

The present invention will now be further described with reference to the following non-limiting examples, and the accompanying illustrative drawings, of which:

FIG. 1 shows percentage A431 cell death induced by photodynamic cell killing following treatment with MAL in the absence and presence of the slow release hydrogen sulfide donor ADT-OH and its mitochondrially targeted derivatives (AP39-C8, AP39-C10 and AP39-C12). ns=p>0.05, =p<0.01, *=p<0.001, Student's t-test compared to untreated control. +++=p<0.001, Student's t-test compared to the MAL group. Error bars represent one standard deviation, n=4.

ns=p>0.05, =p<0.01, *=p<0.001, Student's t-test compared to untreated control. ++=p<0.01, +++=p<0.001, Student's t-test compared to the MAL group. Error bars represent one standard deviation, n=4.

Figure 4:
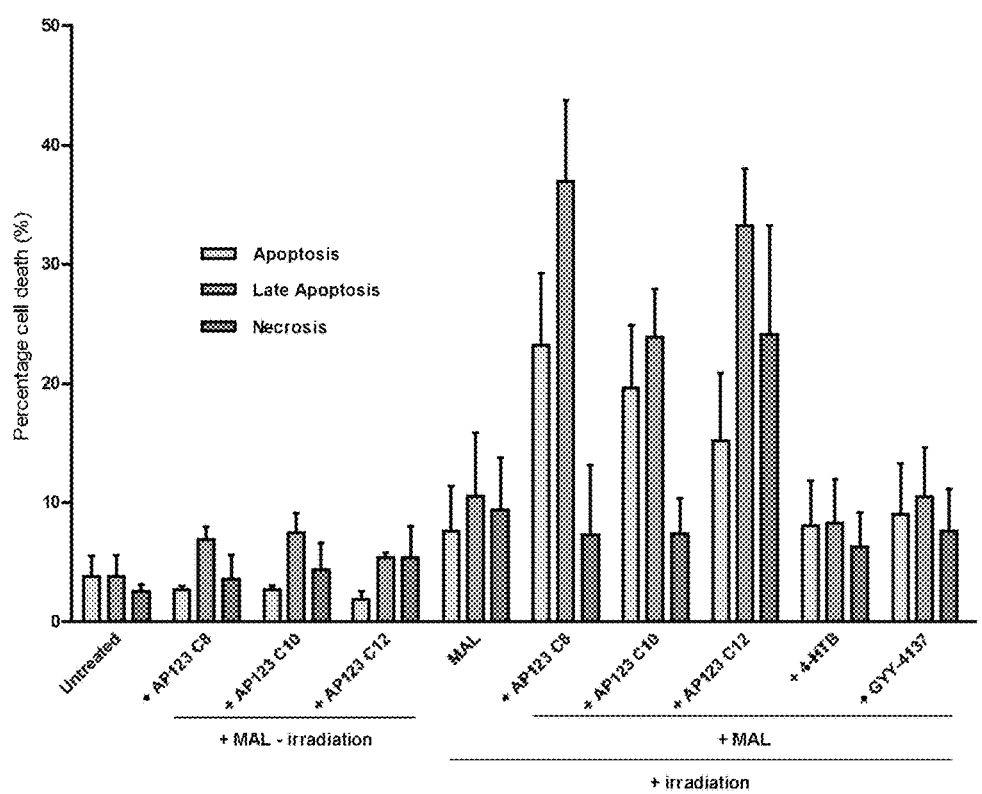

FIG. 4 shows modes of A431 cell death induced by photodynamic cell killing following treatment with MAL in the absence and presence of the slow release hydrogen sulfide donor 4-HTB and its mitochondrially targeted derivatives (AP123-C8, AP123-C10 and AP123-C12). Error bars represent one standard deviation, n=4.

Figure 5:
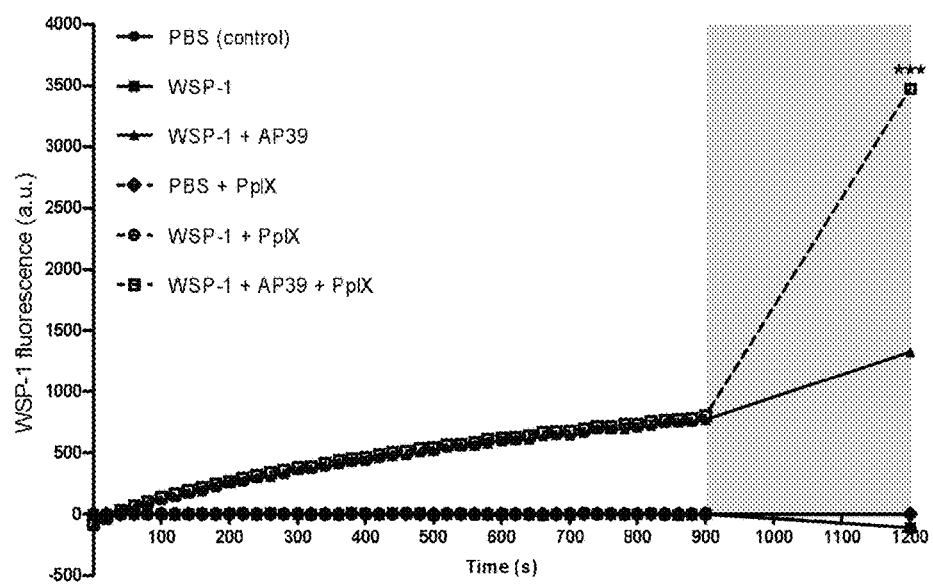

FIG. 5 shows the release of $H_2S$ by AP39-C10 as measured by fluorogenic probe WSP-1. The fluorescence of each well was measured without irradiation for 900 seconds, after which the wells were irradiated, which is the grey section in the figure. Following irradiation, a final fluorescent measurement was recorded for each well (t=1200 s). ***=p<0.001 compared to WSP-1+AP39. Representative of n=4.

Figure 6:
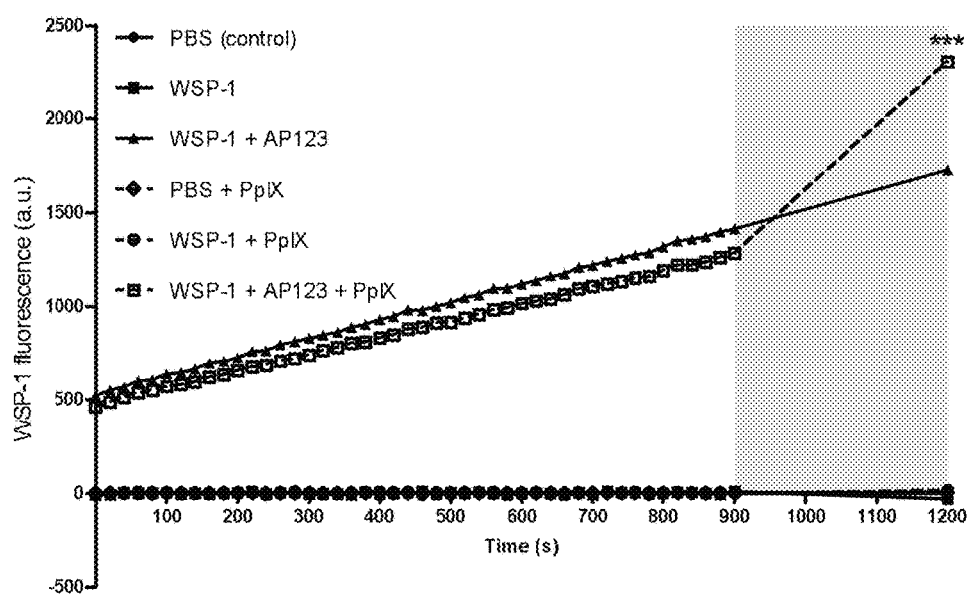

FIG. 6 shows the release of $H_2S$ by AP123-C10 as measured by fluorogenic probe WSP-1. The fluorescence of each well was measured without irradiation for 900 seconds, after which the wells were irradiated, which is the grey section in the figure. Following irradiation, a final fluorescent measurement was recorded for each well (t=1200 s). ***=p<0.001 compared to WSP-1+AP123. Representative of n=4.

Figure 7:
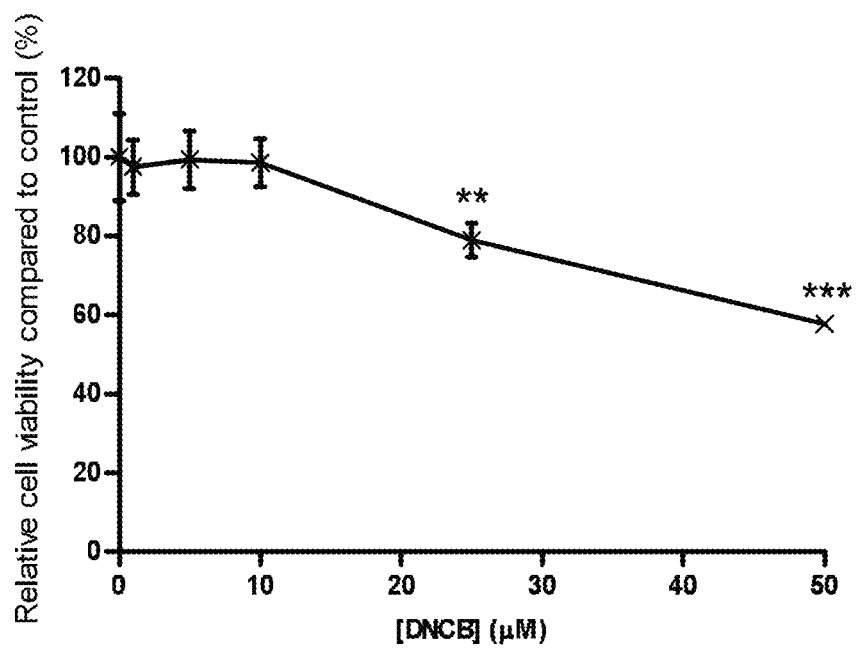

FIG. 7 shows a concentration-response plot of cell viability following treatment of A431 cells with the thioredoxin reductase inhibitor DNCB. Results are plotted as a percentage of viability compared to the untreated control cells (0 µM DNCB). =p<0.01, *=p<0.001, Student's t-test compared to untreated cells. Error bars represent one standard deviation, n=6.

Figure 8:
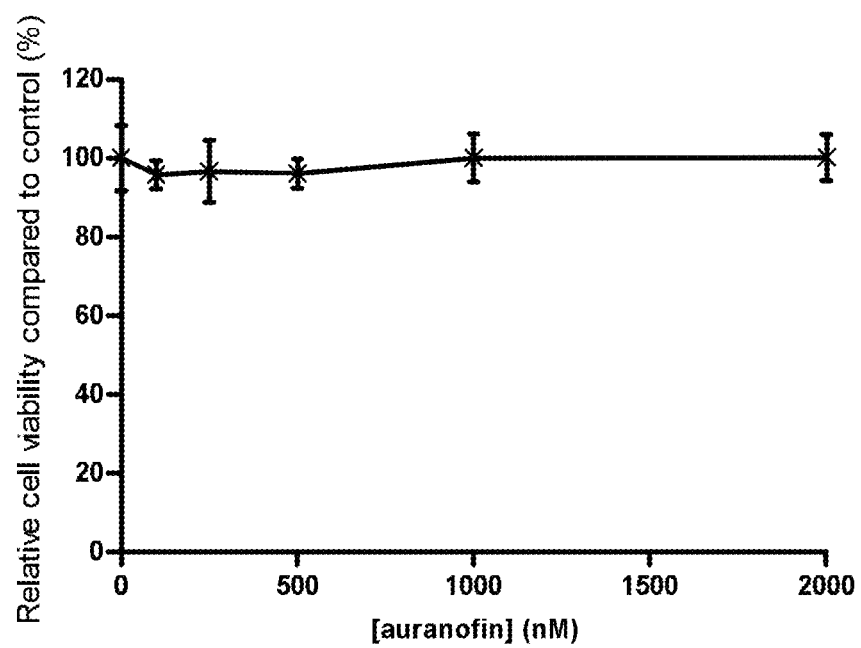

FIG. 8 shows a concentration-response plot of cell viability following treatment of A431 cells with the thioredoxin reductase inhibitor auranofin. Results are plotted as a percentage of viability compared to the untreated control cells (0 nM auranofin). Error bars represent one standard deviation, n=5.

Figure 9:
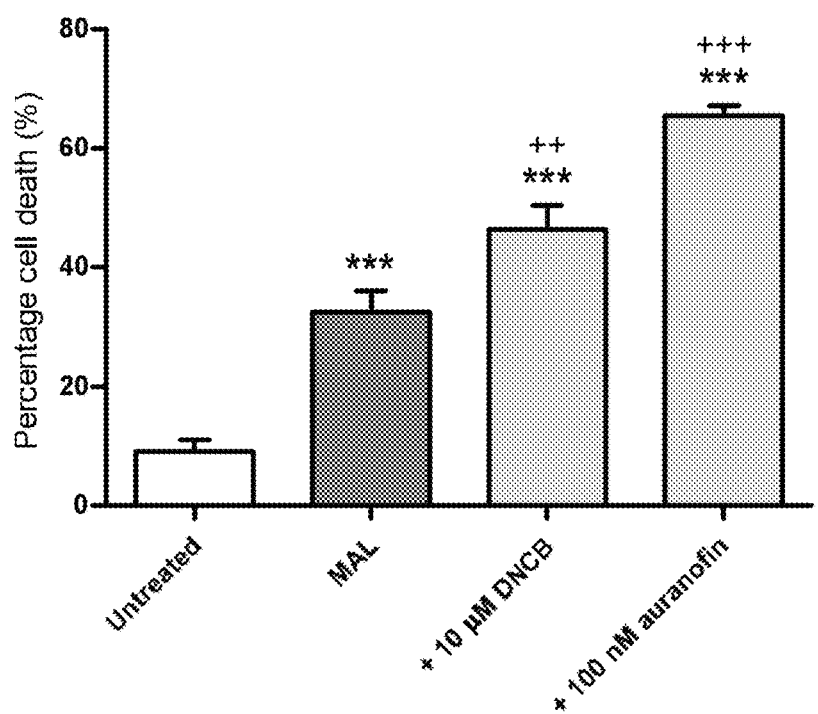

FIG. 9 shows cell death induced by photodynamic cell killing of A431 cells treated with MAL in the absence and presence of the thioredoxin reductase inhibitors auranofin or DNCB. ***=p<0.001, Student's t-test compared to untreated group. ++=p<0.01, +++=p<0.001, Student's t-test compared to MAL-only group. Error bars represent one standard deviation, n=4.

Figure 10:
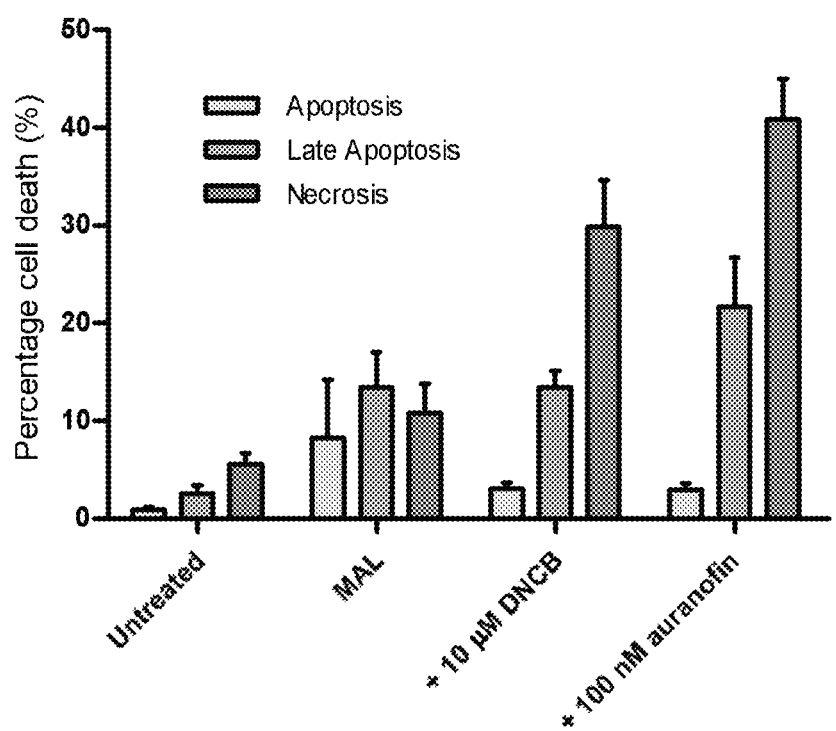

FIG. 10 Modes of cell death following photodynamic cell killing of A431 cells treated with MAL in the absence and presence of thioredoxin reductase inhibitors auranofin or DNCB. Error bars represent one standard deviation, n=4.

Figure 11:
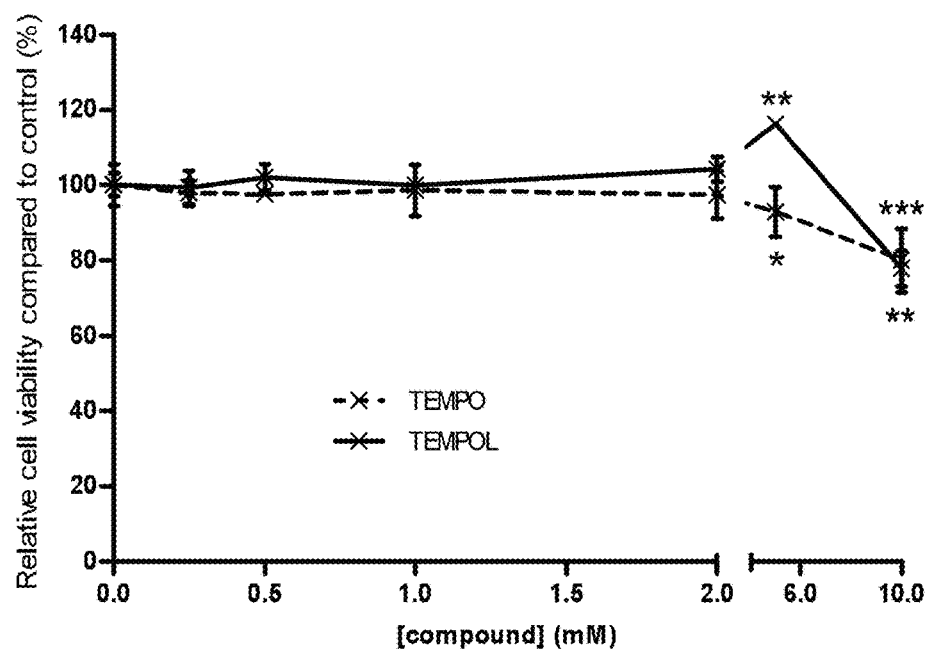

FIG. 11 shows a concentration-response plot of cell viability following treatment of A431 cells with the superoxide scavengers TEMPO and TEMPOL. Results are plotted as a percentage of viability compared to the untreated control cells (0 mM TEMPO or TEMPOL). *=p<0.05, =p<0.01, *=p<0.001, Student's t-test compared to untreated cells. Error bars represent one standard deviation, n=4-5.

Figure 12:
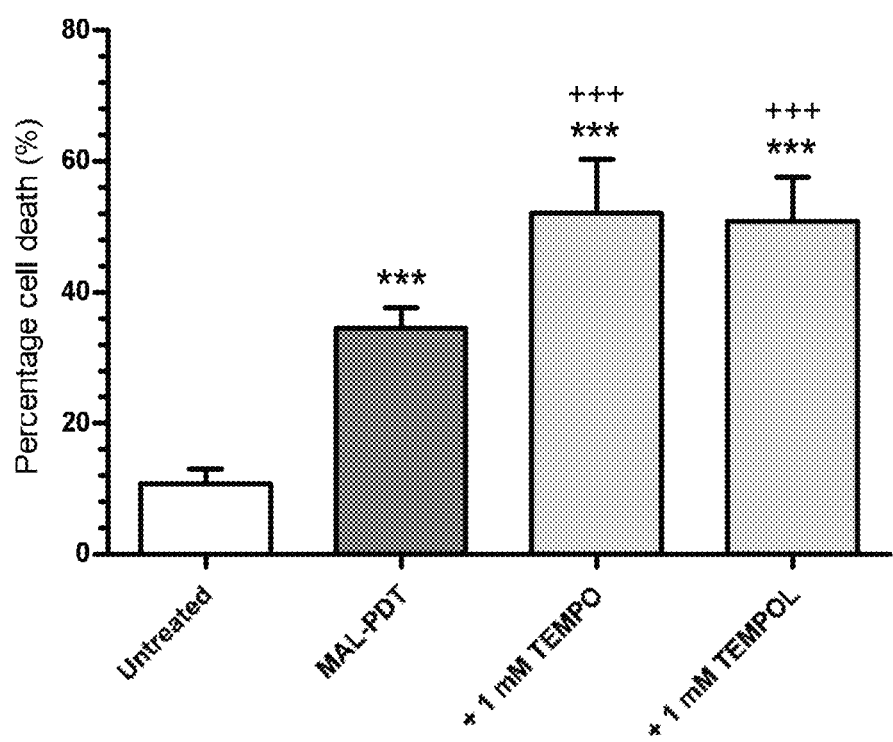

FIG. 12 shows cell death induced by photodynamic cell killing of A431 cells treated with MAL in the absence and presence of TEMPO or TEMPOL. Error bars represent one standard deviation, n=6. =p<0.01, *=p<0.001, Student's t-test compared to untreated group. +++=p<0.001, Student's t-test compared to MAL-only group.

Figure 13:
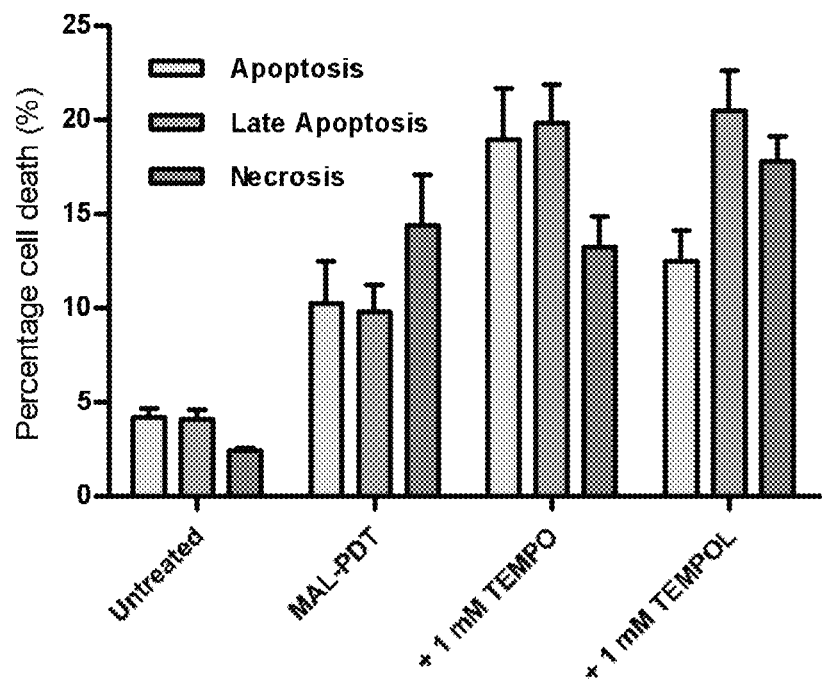

FIG. 13 shows modes of cell death induced by photodynamic cell killing of A431 cells treated with MAL in the absence and presence of TEMPO or TEMPOL. Error bars represent one standard deviation, n=6.

Figure 14:
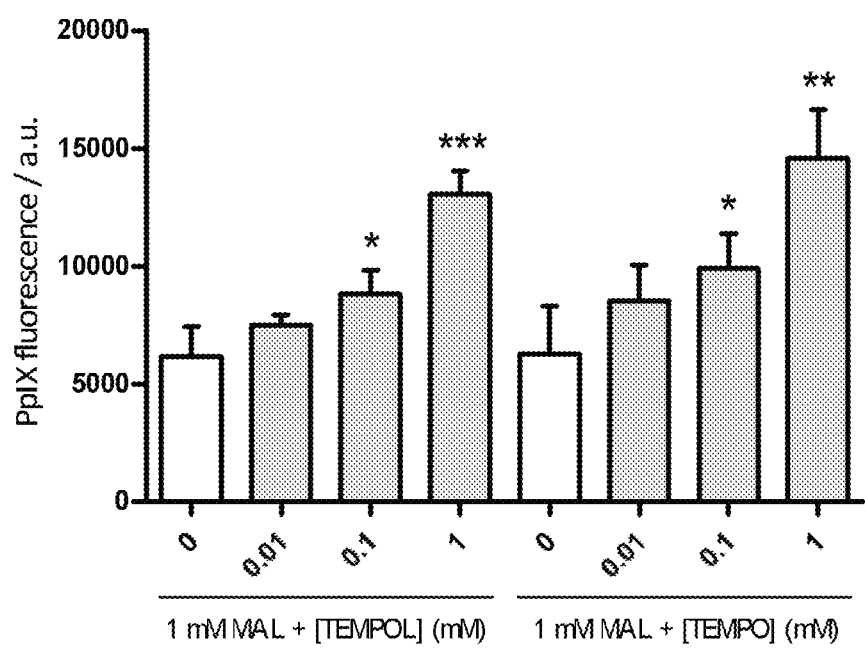

FIG. 14 shows A431 PpIX accumulation following treatment with MAL in the absence and presence of the small molecule antioxidants TEMPOL or TEMPO. Error bars represent one standard deviation, n=4. *=p<0.05, =p<0.01, *=p<0.001, Student's t-test compared to 1 mM MAL-only.

Figure 15:
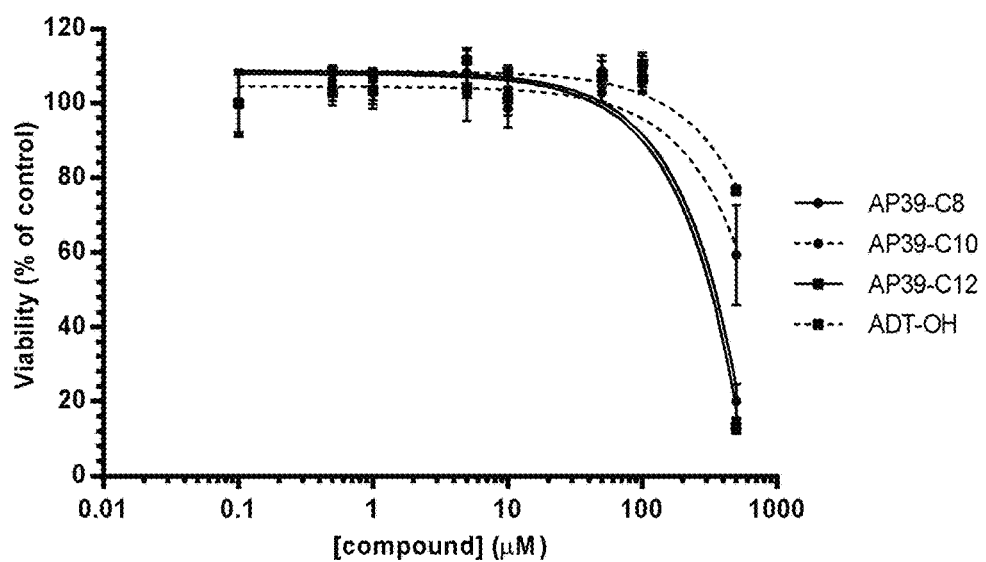

FIG. 15 shows a concentration-response plot of cell viability following treatment of A431 cells with the mitochondria-targeted derivatives (AP39-C8, AP39-C10 and AP39-C12) of the non-targeted slow-releasing hydrogen sulfide donor, ADT-OH. Data are expressed as mean±S.D percentage of cell viability compared to untreated cells. n=4.

Figure 16:
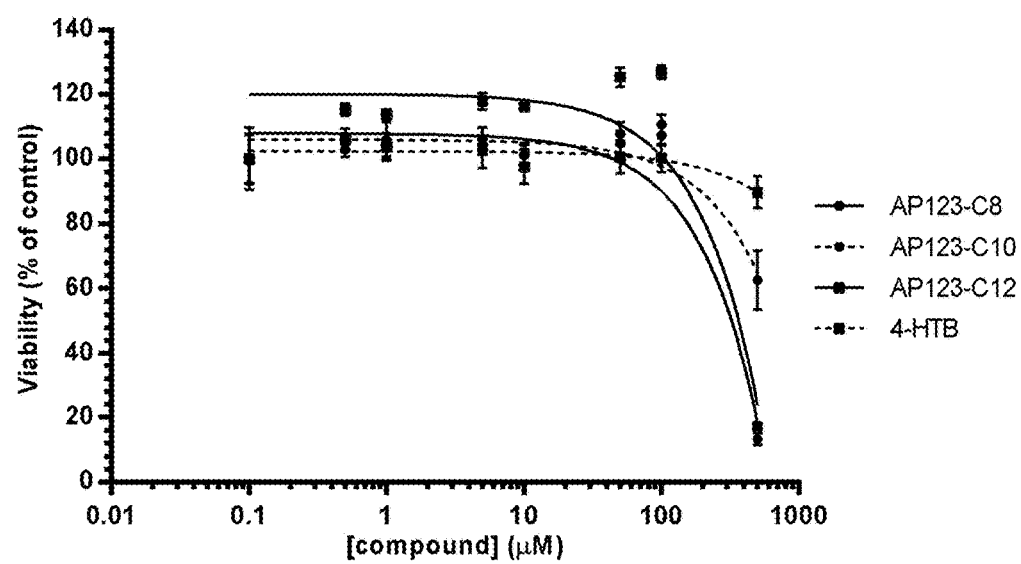

FIG. 16 shows a concentration-response plot of cell viability following treatment of A431 cells with the mitochondria-targeted derivatives (AP123-C8, AP123-C10 and AP123-C12) of the non-targeted slow-releasing hydrogen sulfide donor, 4-HTB. Data are expressed as mean±S.D percentage of cell viability compared to untreated cells. n=4.

Figure 17:
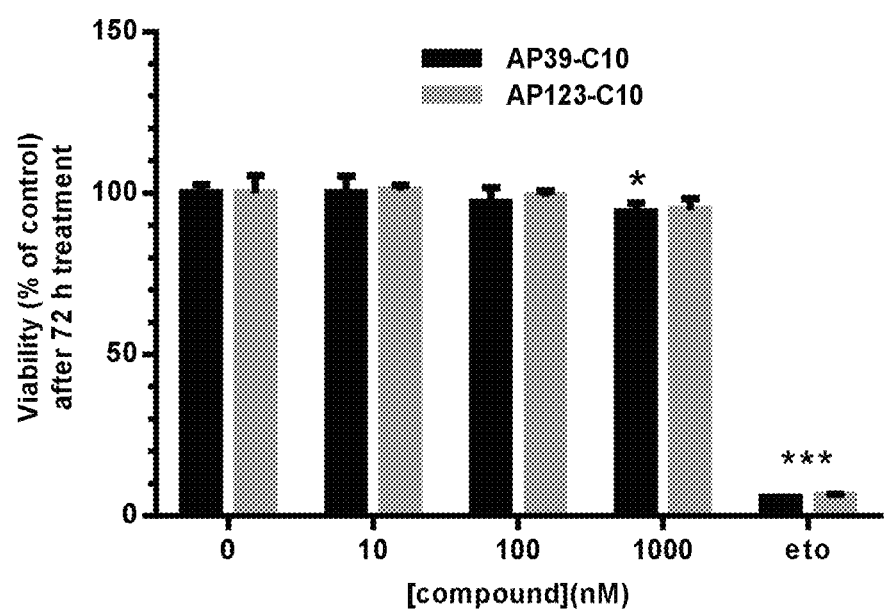

FIG. 17 shows viability of A431 cells following treatment with AP39-C10 and AP123-C10 for 72 hours. Data are expressed as mean±S.D. percentage of cell viability compared to untreated cells. *=p<0.05, ***=p<0.001, Student's t-test c.f. untreated cells (0 nM). n=6.

Figure 18:
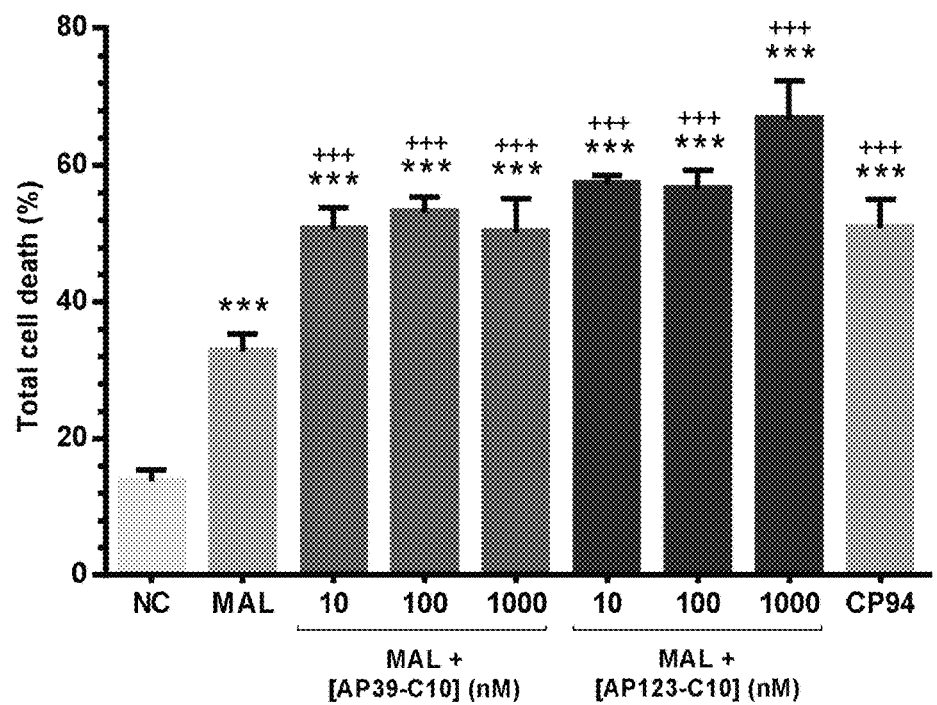

FIG. 18 shows A431 cell death induced by photodynamic cell killing following treatment with MAL in the absence and presence of the slow release hydrogen sulfide donors AP39-C10 and AP123-C10. Data are expressed as mean±S.D. percentage of cell death. ***=p<0.001, Student's t-test c.f. untreated control. +++=p<0.001, Student's t-test c.f. the MAL group. Error bars represent one standard deviation, n=5.

Figure 19:
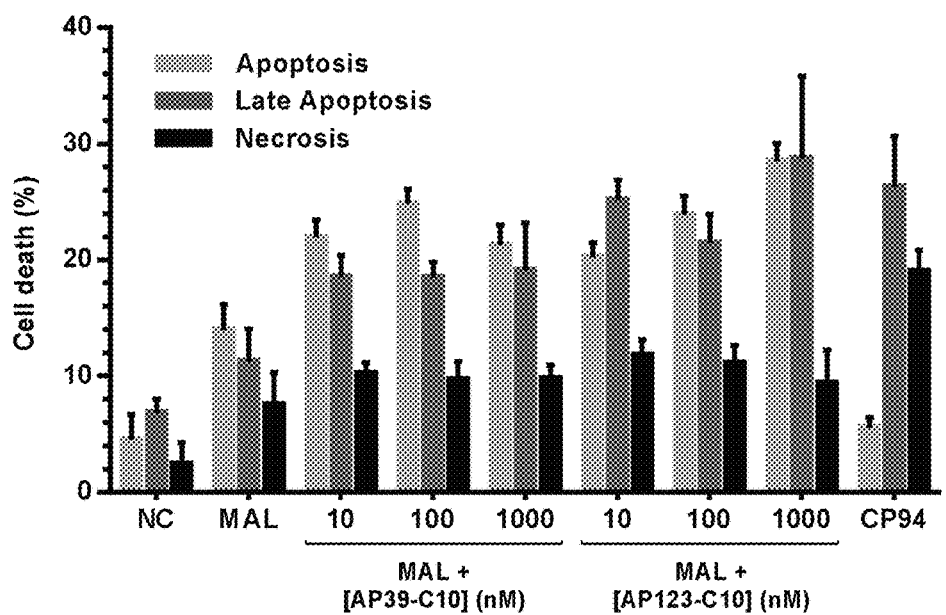

FIG. 19 shows modes of A431 cell death induced by photodynamic cell killing following treatment with MAL in the absence and presence of the slow release hydrogen sulfide donors AP39-C10 and AP123-C10. Data are expressed as mean±S.D. percentage cell death. n=5.

Figure 20:
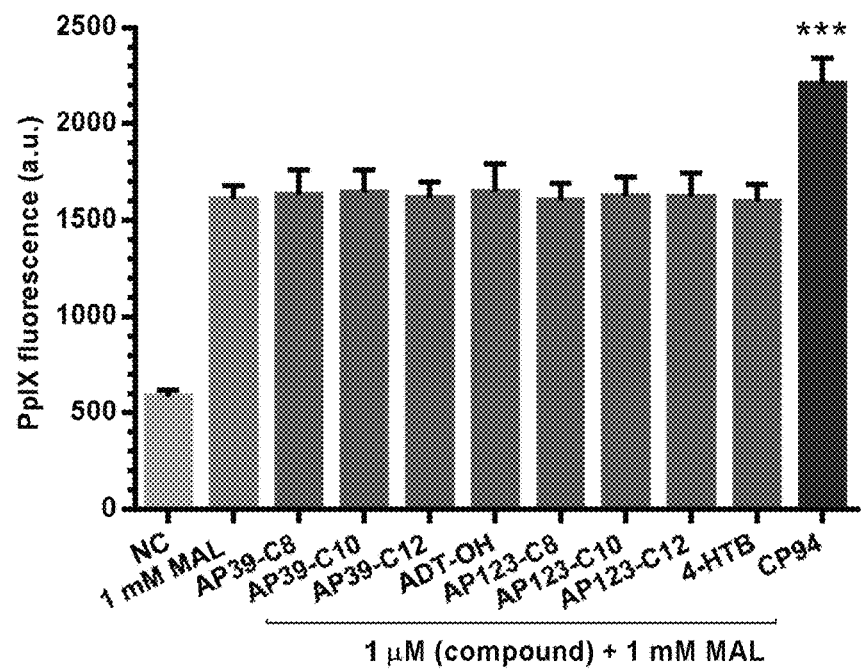

FIG. 20 shows PpIX accumulation in A431 cells following treatment with MAL in the absence and presence of non-targeted and mitochondria-targeted slow-releasing hydrogen sulfide donors. Data are expressed as mean±S.D. arbitrary fluorescence units. ***=p<0.001, Student's t-test c.f. 1 mM MAL. n=4.

Figure 21:
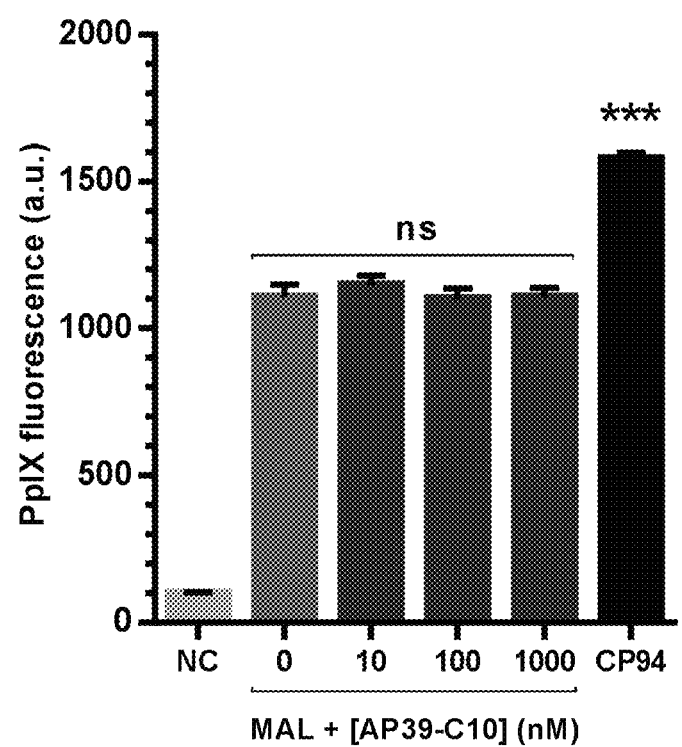

FIG. 21 shows the effects of AP39-C10 on MAL-induced PpIX accumulation in A431 cells. Data are expressed as mean±S.D. arbitrary fluorescence units. ***=p<0.001, Student's t-test c.f. 1 mM MAL. n=4.

Figure 22:
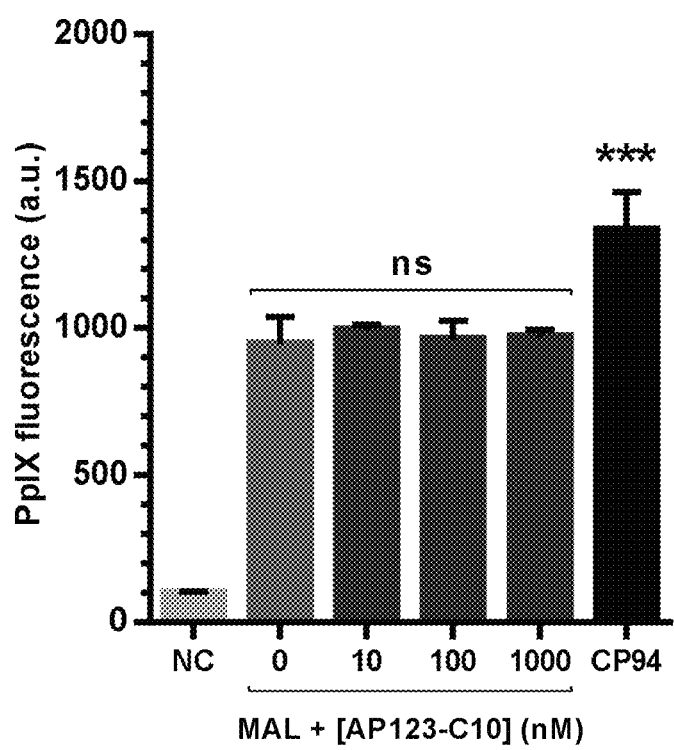

FIG. 22 shows the effects of AP123-C10 on MAL-induced PpIX accumulation in A431 cells. Data are expressed as mean±S.D. arbitrary fluorescence units. ***=p<0.001, Student's t-test c.f. 1 mM MAL. n=4.

Figure 23:
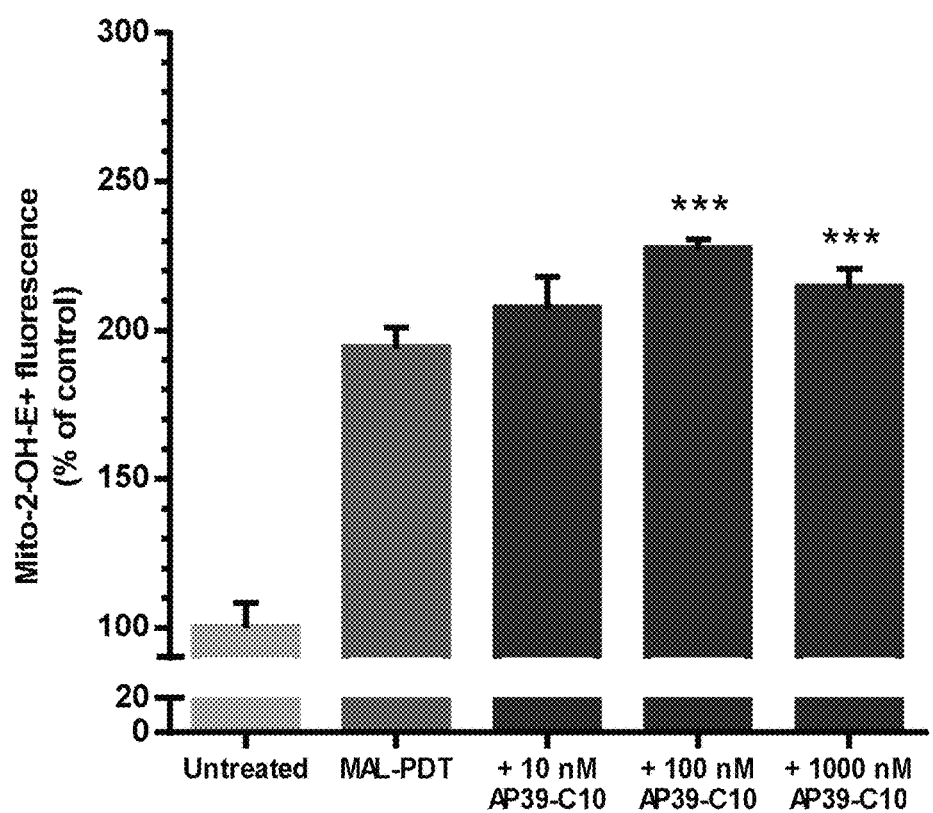

FIG. 23 shows the effects of AP39-C10 on reactive oxygen species generation during photodynamic irradiation of A431 cells pre-treated with MAL. Data are expressed as mean±S.D. percentage of untreated cells. ***=p<0.001, Student's t-test c.f. the MAL group. n=4.

Figure 24:
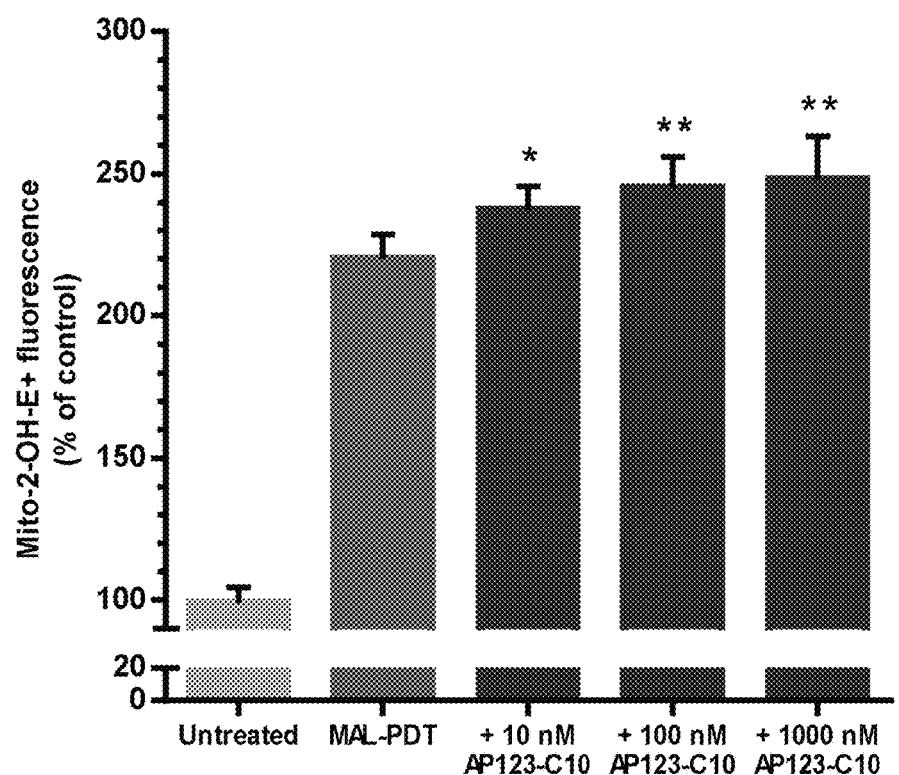

FIG. 24 shows the effects of AP123-C10 on reactive oxygen species generation during photodynamic irradiation of A431 cells pre-treated with MAL. Data are expressed as mean±S.D. percentage of untreated cells. ***=p<0.001, Student's t-test c.f. the MAL group. n=4.

Figure 25:
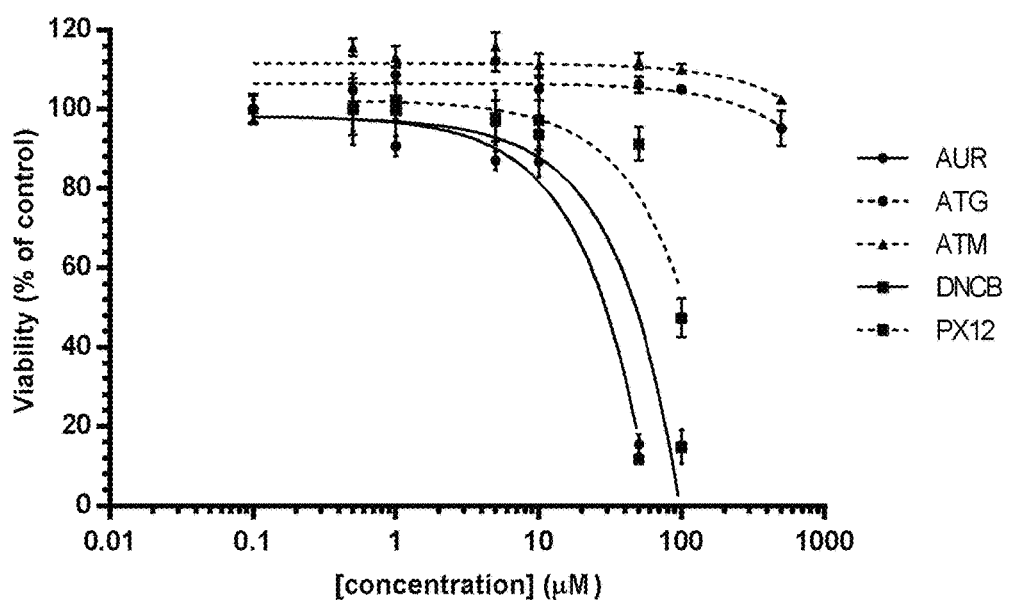

FIG. 25 shows a concentration-response plot of cell viability following treatment of A431 cells with inhibitors of the thioredoxin antioxidant system. Data are expressed as mean±S.D percentage of viability compared to untreated cells. n=3.

Figure 26:
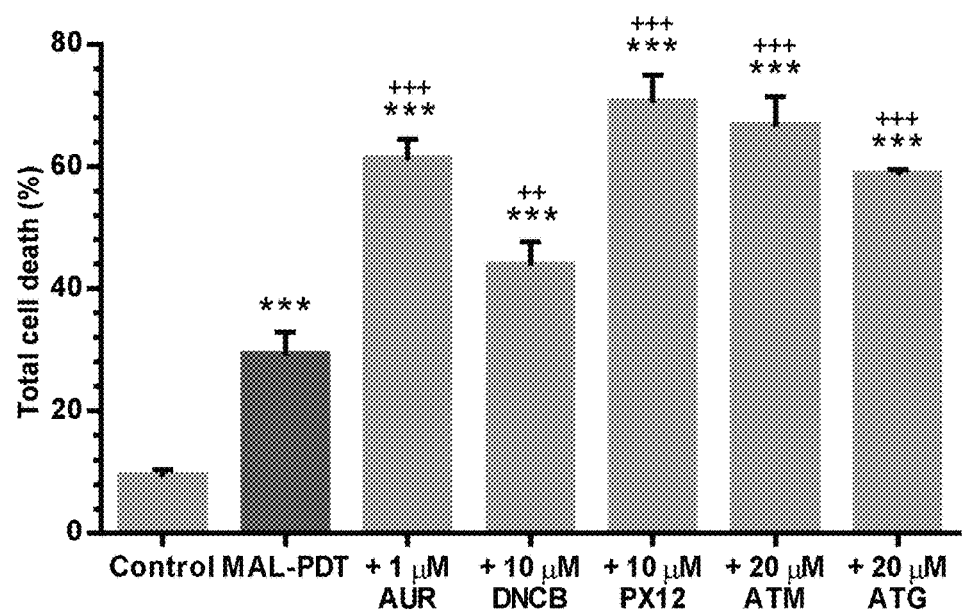

FIG. 26 shows A431 cell death induced by photodynamic cell killing following treatment with MAL in the absence and presence of thioredoxin antioxidant system inhibitors. Data are expressed mean±S.D. percentage of cell death. ***=p<0.001, Student's t-test c.f. untreated control. ++=p<0.01, +++=p<0.001, Student's t-test c.f. MAL-PDT. Error bars represent one standard deviation, n=4.

Figure 27:
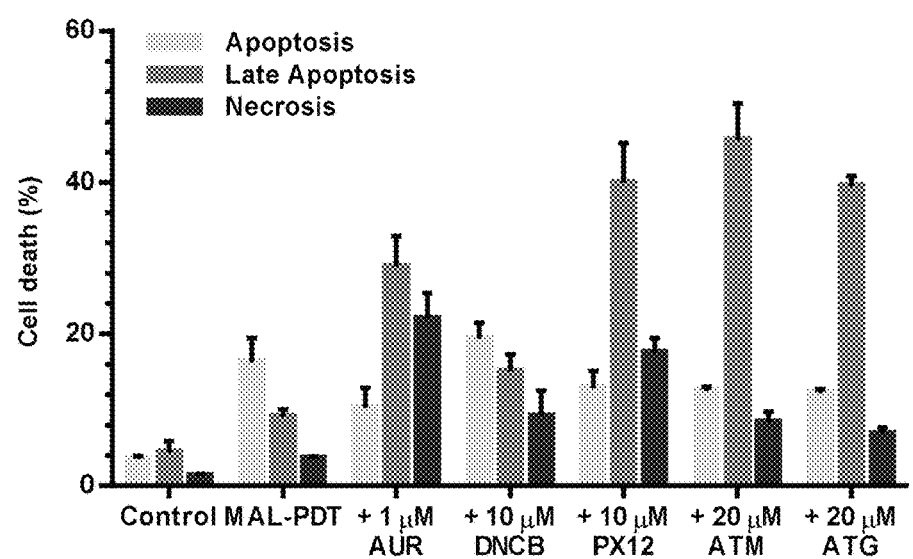

FIG. 27 shows modes of A431 cell death induced by photodynamic cell killing following treatment with MAL in the absence and presence of thioredoxin reductase inhibitors and thioredoxin inhibitors. Data are expressed mean±S.D. percentage of cell death. n=4.

Figure 28:
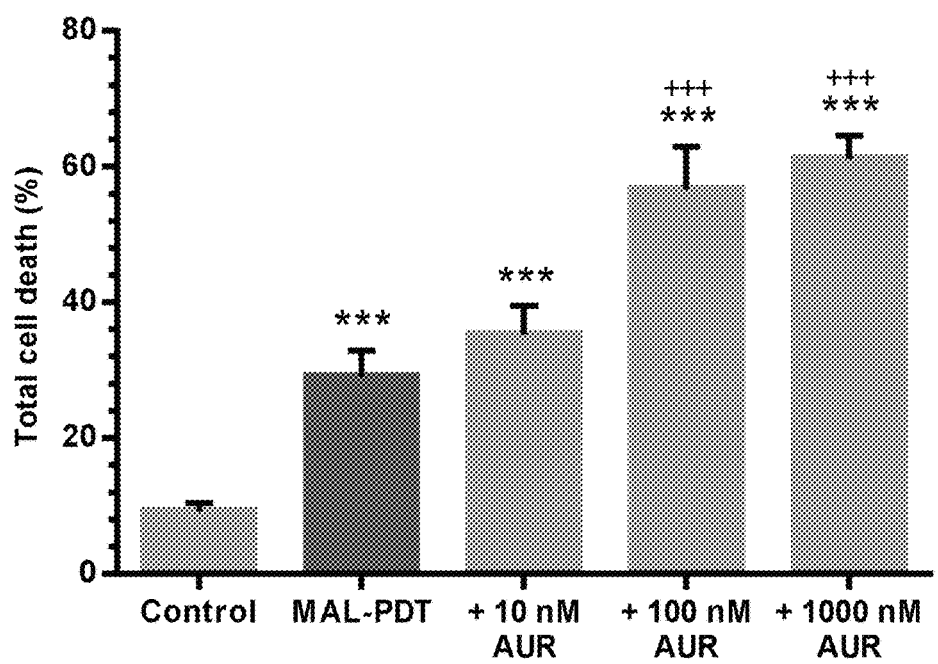

FIG. 28 shows A431 cell death induced by photodynamic cell killing following treatment with MAL in the absence and presence of different concentrations of auranofin. Data are expressed mean±S.D. percentage of cell death. ***=p<0.001 Student's t-test c.f. untreated control. +++=p<0.001 Student's t-test c.f. MAL alone. n=4.

Figure 29:
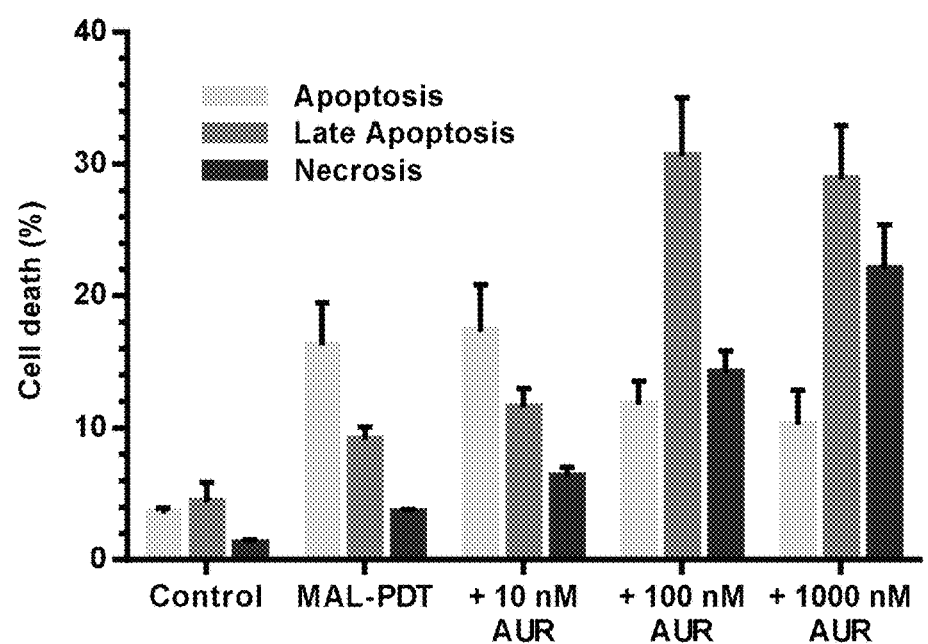

FIG. 29 shows modes of A431 cell death induced by photodynamic cell killing following treatment with MAL in the absence and presence of different concentrations of auranofin. Data are expressed mean±S.D. percentage of cell death. n=4.

Figure 30:
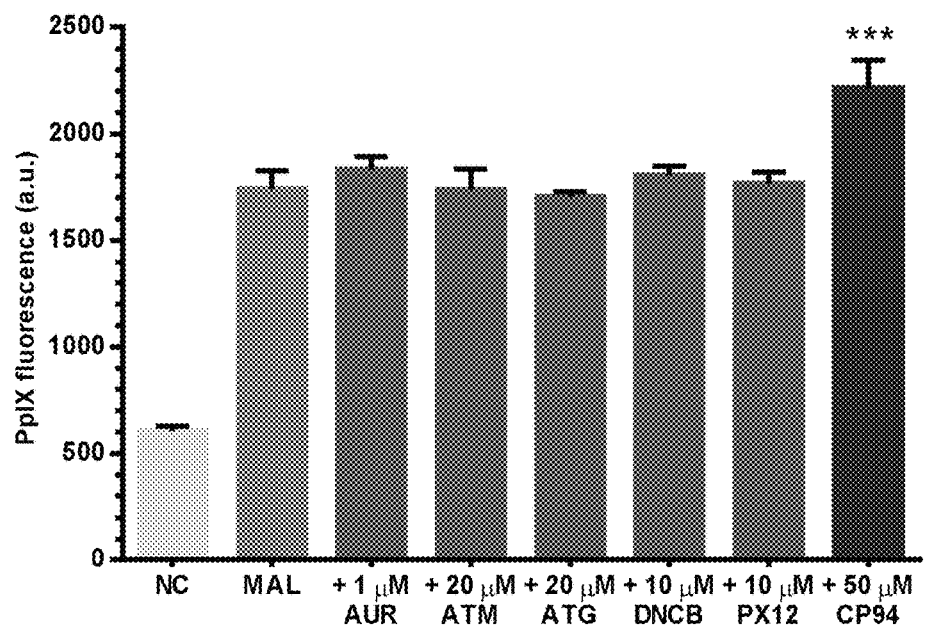

FIG. 30 shows PpIX accumulation in A431 cells following treatment with MAL in the absence and presence of thioredoxin antioxidant system inhibitors. Data are expressed as mean±S.D. arbitrary fluorescence units. ***=p<0.001, Student's t-test c.f. MAL alone. n=4. a.u.=arbitrary units.

Figure 31:
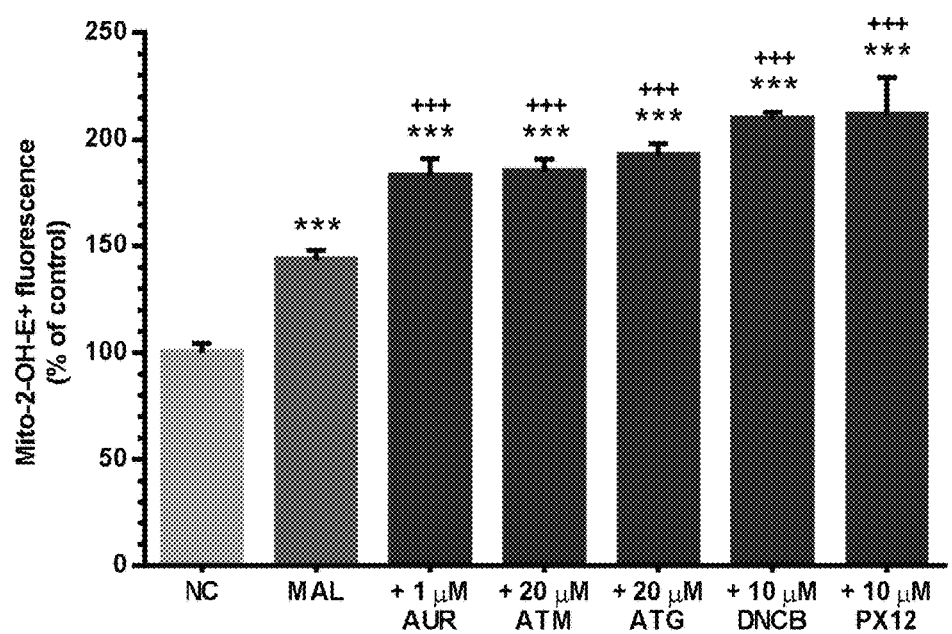

FIG. 31 shows the effects of thioredoxin antioxidant system inhibitors on reactive oxygen species generation during photodynamic irradiation of A431 cells pre-treated with MAL. Data are expressed mean±S.D. percentage of untreated cells. ***=p<0.001, Student's t-test c.f. untreated control, +++=p<0.001 c.f. MAL alone. n=5.

Figure 32:
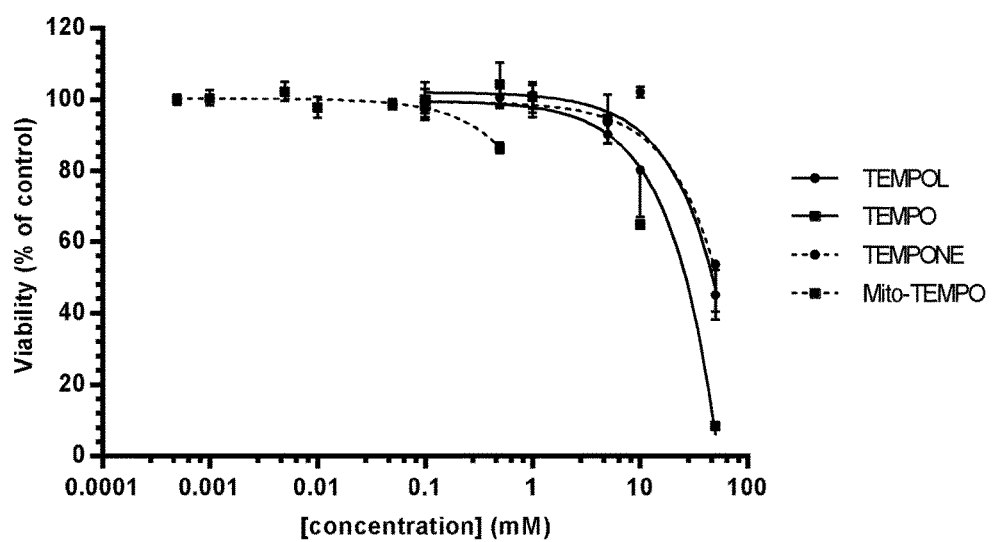

FIG. 32 shows a concentration-response plot of cell viability following treatment of A431 cells with the nitroxides TEMPO, TEMPOL, TEMPONE and MitoTEMPO. Data are expressed as mean±S.D percentage of viability compared to untreated cells. n=3.

Figure 33:
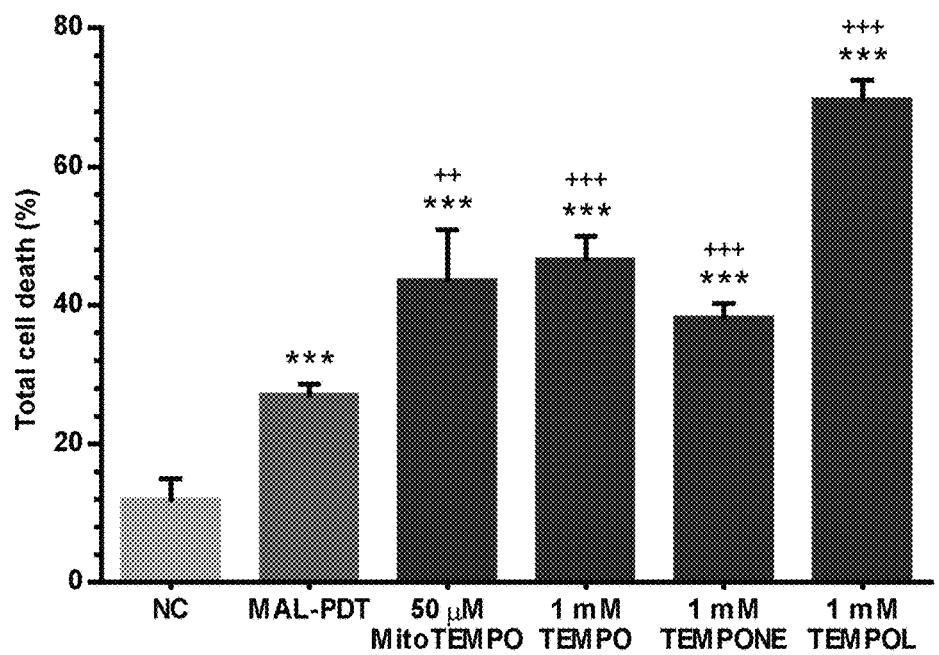

FIG. 33 shows A431 cell death induced by photodynamic cell killing following treatment with MAL in the absence and presence of nitroxides. ***=p<0.001, Student's t-test c.f. untreated control. ++=p<0.01, +++=p<0.001, Student's t-test c.f. MAL-PDT. Error bars represent one standard deviation, n=4.

Figure 34:
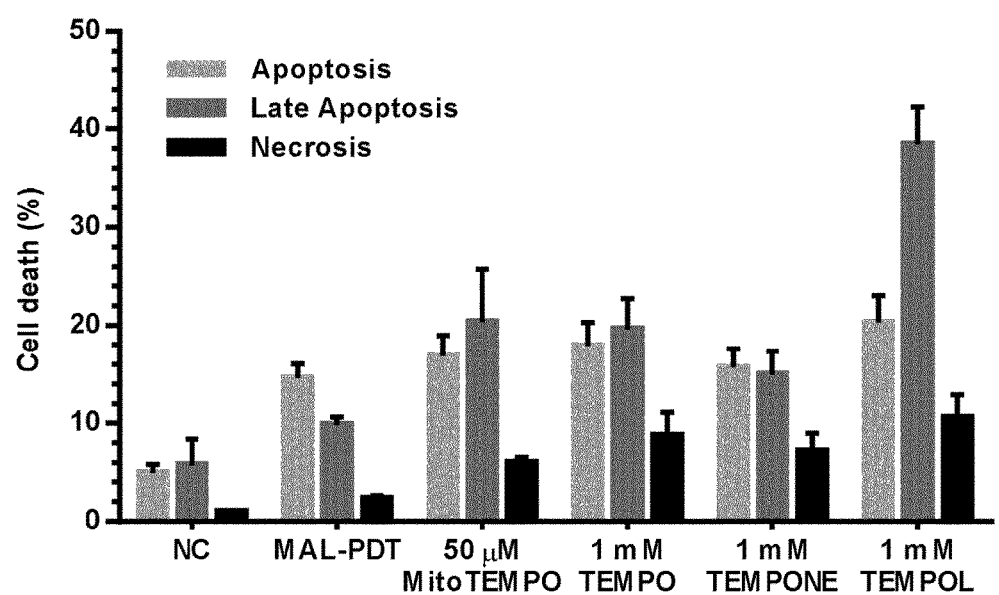

FIG. 34 legend shows modes of A431 cell death induced by photodynamic cell killing following treatment with MAL in the absence and presence of nitroxides. Data are expressed mean±S.D. percentage of cell death. n=4.

Figure 35:
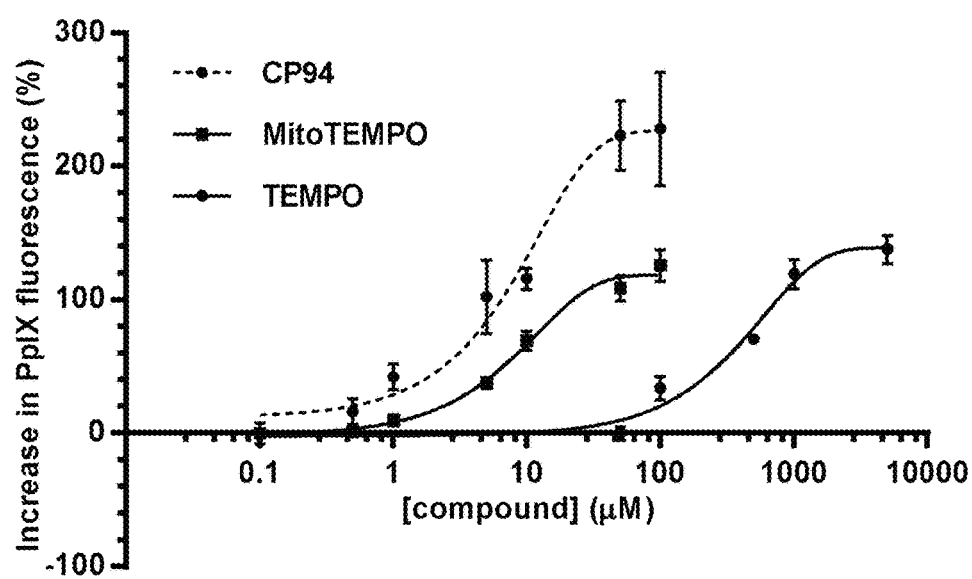

FIG. 35 shows a concentration-response plot showing the effects of TEMPO and MitoTEMPO on MAL-induced PpIX accumulation in A431 cells. Data are expressed mean±S.D. percentage increase in PpIX fluorescence compared to MAL alone. n=4.

Figure 36:
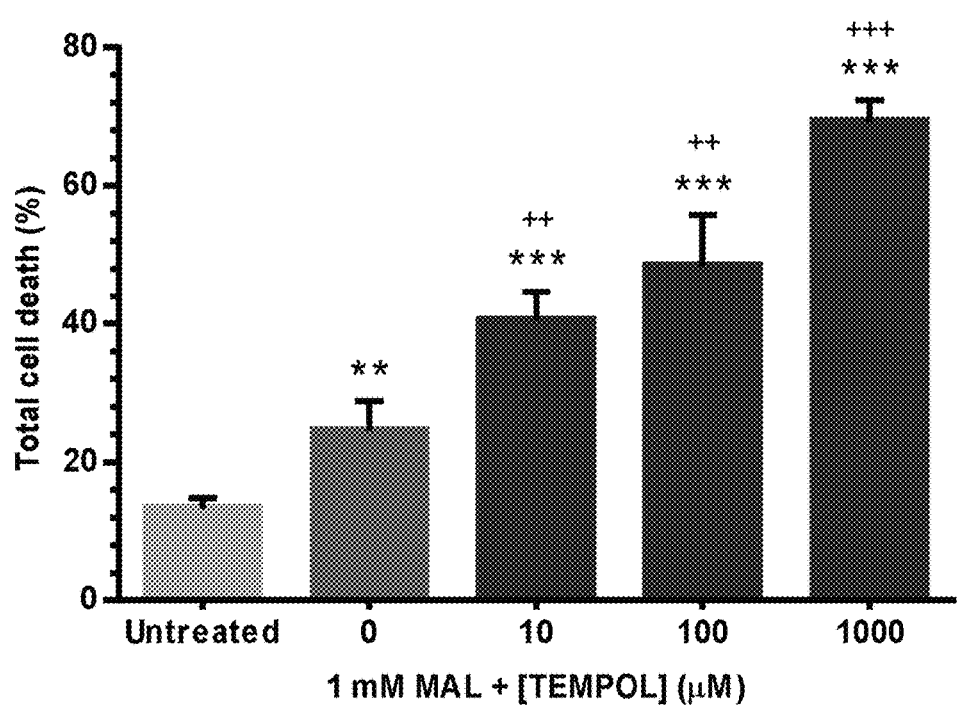

FIG. 36 shows A431 cell death induced by photodynamic cell killing following treatment with MAL in the absence and presence of different concentrations of TEMPOL. Data are expressed mean±S.D. percentage of cell death. =p<0.01, *=p<0.001 Student's t-test c.f. untreated control. ++=p<0.01, +++=p<0.001 Student's t-test c.f. MAL alone. n=4.

Figure 37:
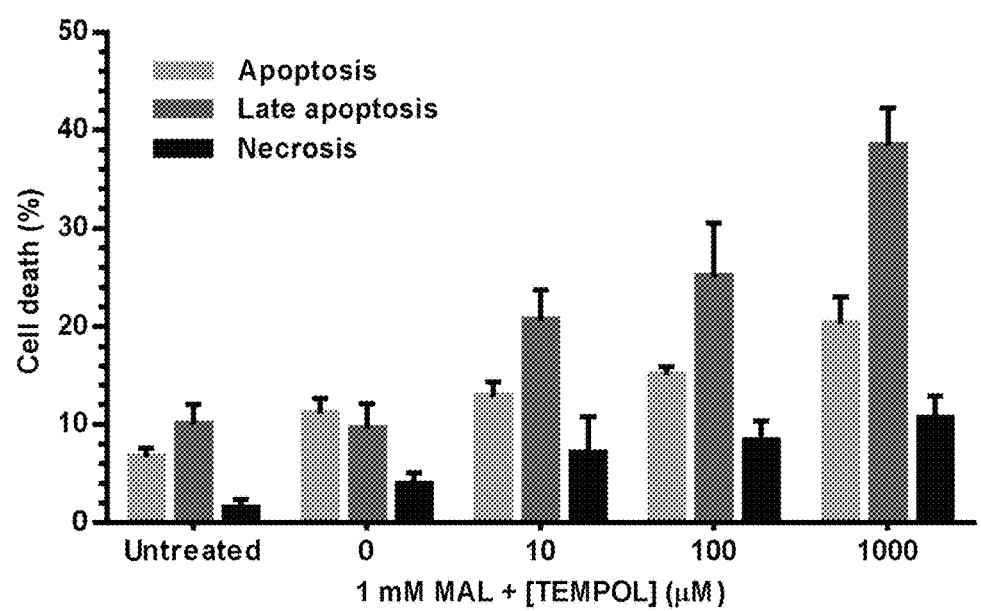

FIG. 37 shows modes of A431 cell death induced by photodynamic cell killing following treatment with MAL in the absence and presence of nitroxides. Data are expressed mean±S.D. percentage of cell death. n=4.

Figure 38:
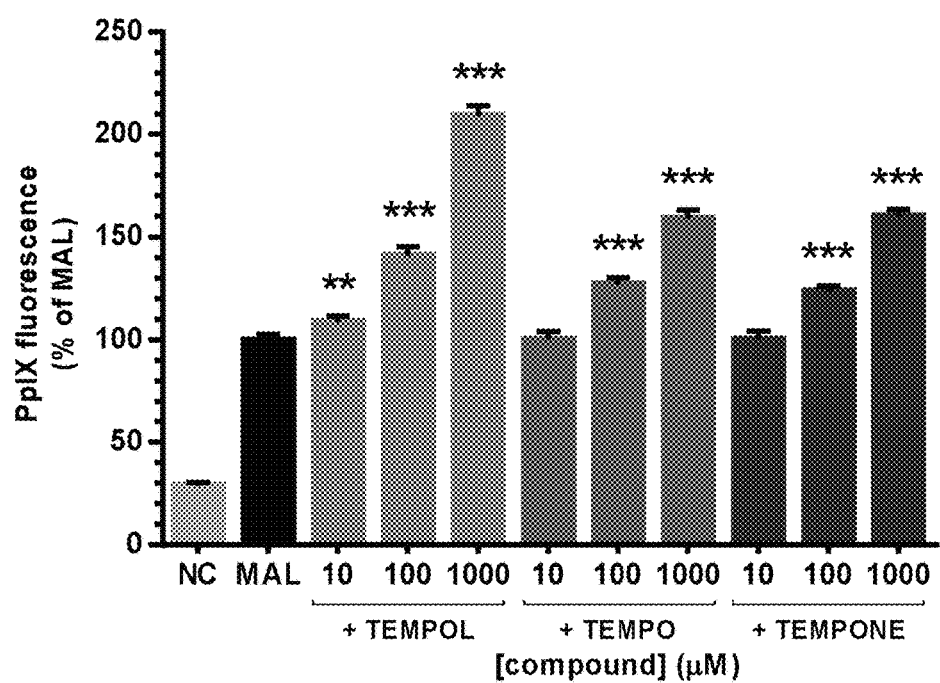

FIG. 38 shows a concentration-response plot showing the effects of TEMPOL, TEMPONE and TEMPO on MAL-induced PpIX accumulation in A431 cells. Data are expressed mean±S.D. percentage change in PpIX fluorescence compared to MAL alone. =p<0.01, *=p<0.001 c.f. MAL alone. n=4.

Figure 39:
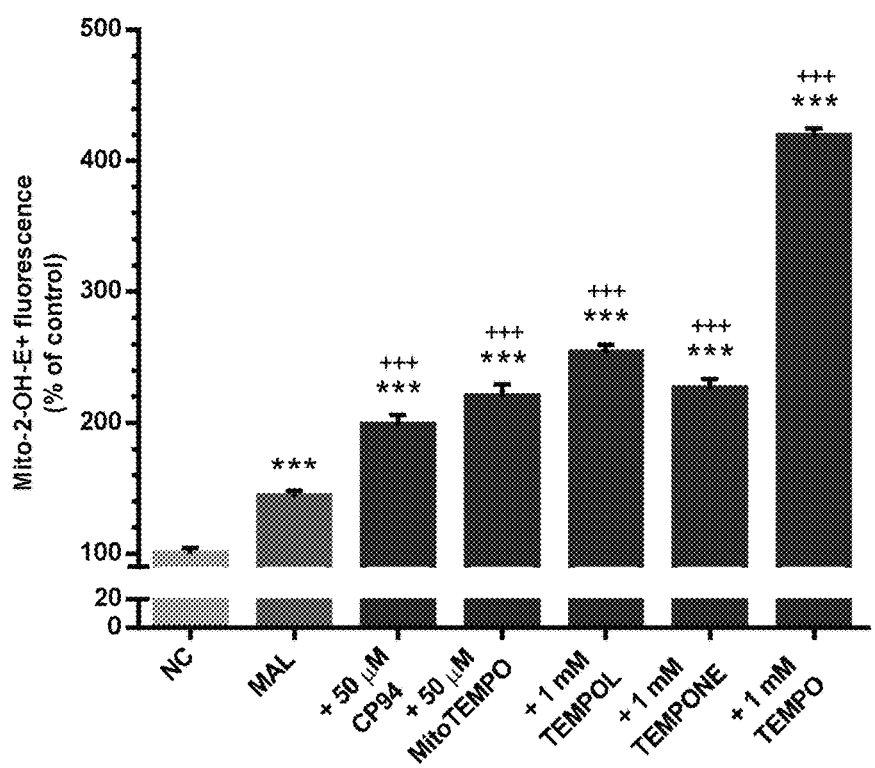

FIG. 39 shows the effects of nitroxides on reactive oxygen species generation during photodynamic irradiation of A431 cells pre-treated with MAL. Data are expressed mean±S.D. percentage of untreated cells. ***=p<0.001, Student's t-test c.f. untreated control, +++=p<0.001 c.f. MAL alone. n=5.

Figure 40:
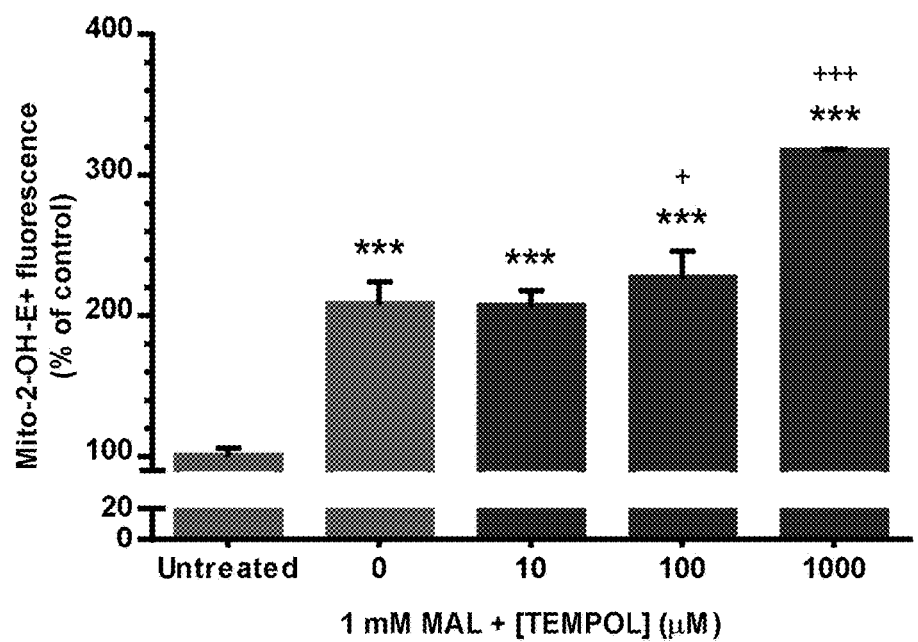

FIG. 40 shows the effects of different concentrations of TEMPOL on reactive oxygen species generation during photodynamic irradiation of A431 cells pre-treated with MAL. ***=p<0.001, Student's t-test c.f. untreated control, +=p<0.05, +++=p<0.001 c.f. MAL alone. Error bars represent one standard deviation, n=4.

EXPERIMENTAL METHODS

All solutions used in the following methods were pre-gassed with 2% $O_2$, 5% $CO_2$ and 93% $N_2$, to investigate effects under a physiological $[O_2]$ of 2%.

Concentration-Response Toxicity Tests

A431 cells were seeded at a density of $1\times10^5$ cells/ml in 96 well plates and incubated under 2% $O_2$ for 48 h prior to treatment. After 24 h, the culture medium was replaced and the cells were placed back into the incubators under 2% $O_2$. Following this incubation period, the culture medium was then removed and the plates were washed with PBS. The cells were then treated with 1 mM MAL in the absence or presence of one of the compounds of interest and then incubated again at 2% $O_2$ for 3 h. For experiments carried out with SRHDs, this treatment step was carried out for 5 h at 2% $O_2$. After treatment, the cells were washed with PBS, the culture medium was replaced and the cells were placed back under 2% $O_2$ for 3 h. Following this final incubation, cell death was analysed using the resazurin viability assay.

Resazurin Microtitre Cell Viability Assay

Resazurin (7-hydroxy-3H-phenoxazin-3-one 0-oxide) is a weakly fluorescent blue dye used primarily in oxidation-reduction cell viability assays. Irreversible NADH-dependent reduction by the mitochondria in mammalian cells leads to the production of resorufin, a highly fluorescent product with excitation at 571 nm, emission at 585 nm. As the reduction of resazurin to resorufin is primarily driven by mitochondria it can be used as an estimate of cell viability when investigating the toxicity of compounds, as dead or dying cells have a decreased mitochondrial activity, producing less resorufin and therefore less fluorescence. Using resazurin in conjunction with microtitre (96 well) plates allows high throughput screening of compounds, which can later be confirmed by other, more definitive methods such as flow cytometry.

A431 cells were seeded into 96 well plates at a density of $1.5*10^6$ cells per ml (200 μl per well, $3*10^5$ cells) and incubated for 24 h to adhere. Following incubation, the cells were washed and treated with the compound of interest for the relevant time, and then washed with PBS. 55 μM resazurin was diluted to 10% (5.5 μM) in fresh culture medium and applied to the cells. After a 2 h incubation, the fluorescence of each well was measured (excitation: 571 nm, emission: 585 nm) using a fluorescence plate reader. Data from these experiments was plotted as a percentage of cell viability compared to untreated control cells.

Photodynamic Cell Killing in the Presence of Slow Release Hydrogen Sulfide Donors (SRHDs)

A431 cells (human epithelial squamous cell carcinoma cells) were seeded at a density of $1 \times 10^6$ cells/ml in T12.5 cm$^2$ flasks and incubated under 2% $O_2$ for 48 h prior to treatment. After 24 h, the culture medium was replaced and the cells were placed back into the incubators under 2% $O_2$. Following this incubation period, the culture medium was then removed and the flasks were washed with PBS. The cells were then treated with one of the SRHDs and incubated at 2% $O_2$ for 2 h, after which MAL was added to a final concentration of 1 mM and the cells were incubated at 2% $O_2$ for 3 h. This meant in total, the cells were treated with the SRHDs for 5 h.

After this treatment, the cells were irradiated for 5 min (630 nm, 25 J/cm$^2$), then washed with PBS and the culture medium was replaced, after which the cells were placed back under 2% $O_2$ and incubated for a further 3 h. Following this final incubation, cell death was analysed by annexin V-FITC and propidium iodide staining in conjunction with flow cytometry.

Photodynamic Cell Killing in the Presence of Inhibitors of the Thioredoxin Antioxidant System or Nitroxides A431 cells (human epithelial squamous cell carcinoma cells) were seeded at a density of $1 \times 10^6$ cells/ml in T12.5 cm$^2$ flasks and incubated under 2% $O_2$ for 48 h prior to treatment. After 24 h, the culture medium was replaced and the cells were placed back into the incubators under 2% $O_2$. Following this incubation period, the culture medium was then removed and the flasks were washed with PBS. The cells were then treated with 1 mM MAL in the absence or presence of one of the chosen inhibitors of the thioredoxin antioxidant system, or nitroxides, and then incubated again at 2% $O_2$ for 3 h.

After this treatment, the cells were irradiated for 5 min (630 nm, 25 J/cm$^2$), then washed with PBS and the culture medium was replaced, after which the cells were placed back under 2% $O_2$ and incubated for a further 3 h. Following this final incubation, cell death was analysed by annexin V-FITC and propidium iodide staining in conjunction with flow cytometry.

Flow Cytometry of Annexin V-FITC and Propidium Iodide Stained Cells

Cell death analysis by flow cytometry was carried out using the annexin V-FITC/propidium iodide protocol. This protocol allows a quantitative assessment of cell death, particularly specific modes of death, and involves staining the cells with fluorescein isothiocyanate-conjugated annexin A5 (annexin V-FITC) and propidium iodide (PI). Positive staining with annexin V-FITC alone indicates an apoptotic cell; positive staining with PI alone indicates a necrotic cell and dual staining of both annexin V and PI indicates a "late apoptotic" cell.

From each flask being assessed, the old medium was removed and placed into a corresponding individual 15 ml Falcon tube in order to collect any cells that may have detached from the surface. The flask was washed once with 1 ml PBS; also deposited in the Falcon tubes. Trypsin (500 µl) was added to each flask and the flasks were returned to the incubator with their caps loosened. Cell detachment was monitored using an inverted light microscope, until 50% of the cells were detached. The flasks were then lightly tapped to detach the remainder of the cells. Medium (2 ml) was added to each flask in order to neutralise the trypsin present before being removed and dispensed into the Falcon tubes. One more wash with PBS was carried out in order to ensure any cells left in the flasks were collected. The Falcon tubes were then centrifuged at 490 g for 3 min, forming a pellet at the bottom of the tube. The supernatant was discarded, and the cells were re-suspended in 5 ml of PBS, in order to wash them, before being centrifuged again at 490 g for 3 min. The wash stage was carried out once more before re-suspending the cell pellet in 95 µl of ice cold calcium ($Ca^{2+}$) buffer (50 mM HEPES, 700 mM NaCl, 12.5 mM CaCl2, pH 7.4) and adding 5 µl 12.5 µg/ml of annexin V-FITC (final concentration, 1.25 µg/ml), under reduced light conditions to prevent bleaching of the FITC. The Falcon tubes were placed on ice and in the dark for 15 min to allow annexin V staining. After 15 min, 860 µl of $Ca^{2+}$ buffer (10 mM Hepes adjusted to pH 7.4, 140 mM NaCl and 2.5 mM $CaCl_2$) was added, followed by 40 µl of 1 mg/ml PI in water (final concentration, 0.04 mg/ml) to give a final volume of 1 ml. The samples were then ready to be assessed by flow cytometry.

The following flow cytometry process of sample detection was used. When using annexin V-FITC and PI, the detectors being used were FL1 ($\lambda_{max}$=520 nm) and FL3 ($\lambda_{max}$=670 nm), respectively, each with their own logarithmic histogram generated by the software. The intensity of the fluorescence detected is measured on a logarithmic scale on the x-axis and the y-axis represents the number of cells detected at a given fluorescence intensity. A plot of FL1/FL3 produces a 4-quadrant graph, where unstained and untreated cells are located in the bottom left quadrant, representing any cells found in the 1$^{st}$ decade of the single plot logarithmic histograms. Single staining with annexin V-FITC and PI are located in the bottom right and top left quadrant, respectively, and dual staining is located in the top right quadrant. These quadrants represent any cells detected above the 1$^{st}$ decade of the logarithmic histograms.

Effects of Irradiation of PpIX in the Presence of Slow Release Hydrogen Sulfide Donors (SRHDs) in a Cell Free System Fluorogenic probe WSP-1 (3'-methoxy-3-oxo-3H-spiro [isobenzofuran-1,9'-xanthen]-6'-yl 2-(pyridin-2-yldisulfanyl)benzoate) can be used to detect $H_2S$. WSP-1 reacts with $H_2S$ to form a fluorescent product (Liu, C. et al., Angew Chem. Int. Ed. Engl. 2011, 50, 10327-10329; Cortese-Krott, M. M. et al., Redox Biol. 2014, 2, 234-244.)

In a cell free system, solutions of the $H_2S$-detecting fluorogenic probe WSP-1 (100 µM) were made up in the absence and presence of AP39-C10 and AP123-C10 (100 µM) and in the absence and presence of PpIX (2 µM). For those solutions containing AP39-C10, the reducing agent DTT (100 µM) was also added as AP39-C10 does not release $H_2S$ in the absence of a reductant. The solution was pipetted into individual wells of a 96 well plate and the fluorescence of each well was measured (excitation 465 nm, emission 515 nm) using a SpectraMax M2e fluorescent plate reader, every 20 seconds for a period of 15 minutes (900 s). After this was completed, the wells were irradiated (636±5 nm, 25 J/cm$^2$). Following irradiation, a final fluorescent measurement was recorded for each well (t=1200 s).

Effects of Nitroxides on PpIX Accumulation

A431 cells were seeded into 96 well plates at a density of $1.5 \times 10^6$ cells per ml (200 µl per well, $3 \times 10^5$ cells) and incubated for 24 h to adhere. The cells were then treated with 1 mM MAL in the absence or presence of a range of concentrations of TEMPOL or TEMPO and incubated again at 2% $O_2$ for 3 h. After treatment, the cells were washed with PBS and a final 100 µl PBS was pipetted into each well for fluorescence readings. The fluorescence of PpIX was measured using a BMG Pherastar plate reader with a 410 nm excitation filter and a 630 nm emission filter.

EXAMPLE 1

Effects of Slow Release Hydrogen Sulfide Donors on Photodynamic Cell Killing Compounds Tested The effects of slow-releasing $H_2S$ donors (SRHDs) on photodynamic cell killing were investigated by using mitochondrially targeted compounds containing a triphenylphosphonium cation ($TPP^+$) as the mitochondrial targeting group with two different $H_2S$ releasing moieties and differing chain lengths.

"AP39" compounds AP39-C8, AP39-C10 and AP39-C12 are related mitochondrially targeted slow-releasing $H_2S$ donors with differing chain lengths, which have the following structures:

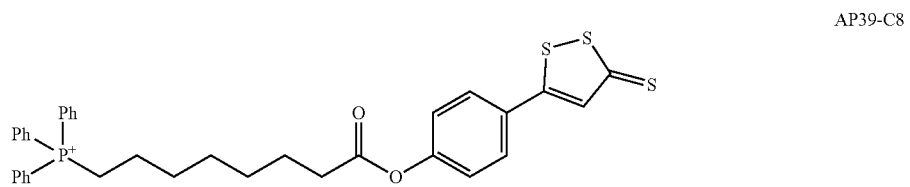
AP39-C8

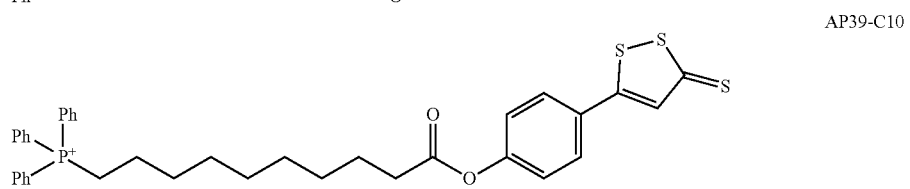
AP39-C10

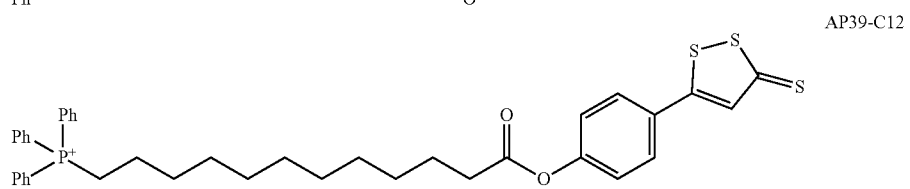
AP39-C12

"AP123" compounds AP123-C8, AP123-C10 and AP123-C12 are related mitochondrially targeted slow-releasing $H_2S$ donors with differing chain lengths, which have the following structures:

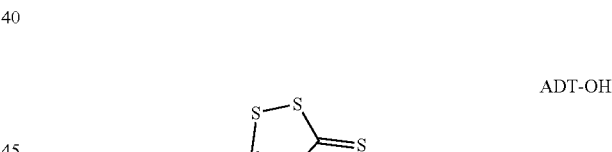
AP123-C8

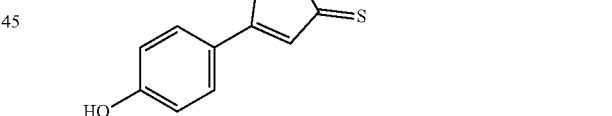
AP123-C10

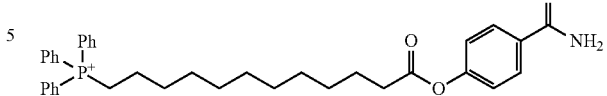
AP123-C12

The AP39 and AP123 compounds can be prepared using the method described in WO 2013/045951.

Additionally, the $H_2S$ releasing moieties of the AP39 and AP123 compounds, 5-(4-hydroxyphenyl)-3H-1,2-dithiole-3-thione (ADT-OH) and 4-hydroxythiobenzamide (4-HTB) were also used for comparison.

ADT-OH

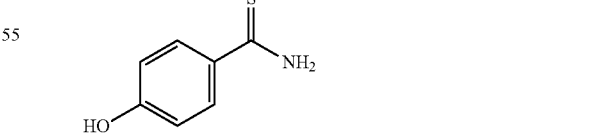
4-HTB

ADT-OH can be prepared using the method described in US 2008/0004245.

4-HTB is commercially available from Sigma-Aldrich.

Slow-releasing $H_2S$ donor GYY4137 was also used for comparison. GYY4137 is a non-targeted slow-releasing $H_2S$ donor of the following structure:

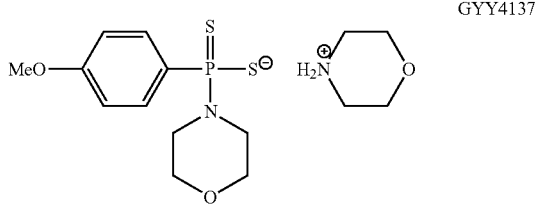 [SMILES: COc1ccc(P(=S)([S-])N2CCOCC2)cc1 ; C1COCC[NH2+]1]

GYY4137

GYY4137 is commercially available or can be prepared using the method described in Li L et al., Circulation 2008, 117:2351-2360.

Results

A431 cells were treated with 1 mM MAL in the absence and presence of an SRHD (1 μM) and with or without irradiation. Cell viability was assessed 3 hours post-irradiation/post-treatment. For the cells treated with MAL in the presence of an SRHD, in order to allow for $H_2S$ to accumulate, incubation with the SRHD was carried out for a total of 5 hours. The cells were treated with the SRHDs 2 hours prior to addition of MAL, followed by incubation with MAL for 3 h. The cells were then irradiated and cell viability was measured 3 hours post-irradiation.

Figure 1:
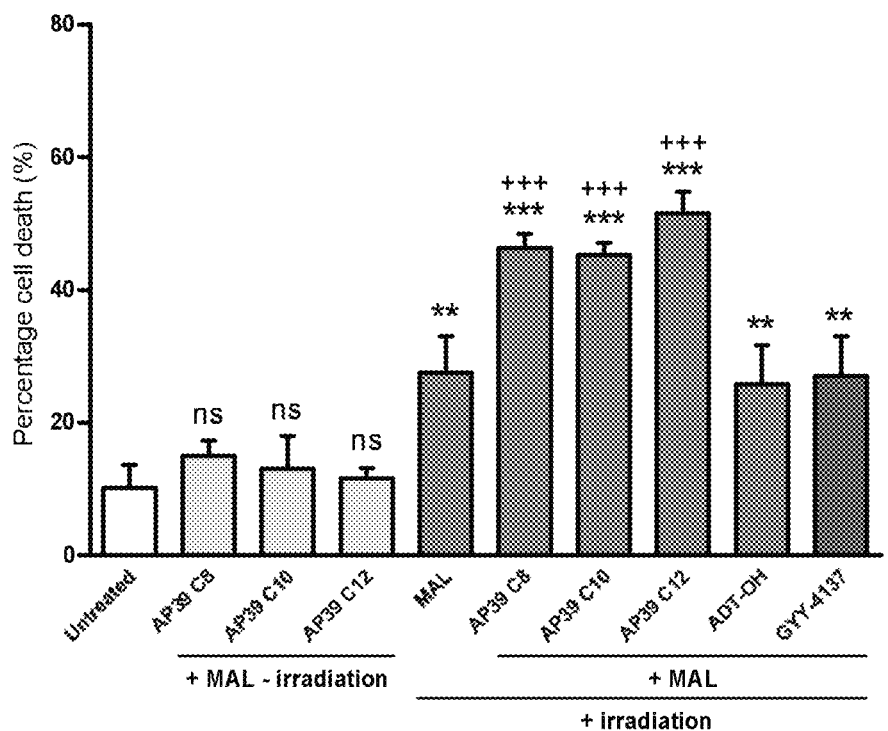
Figure 2:
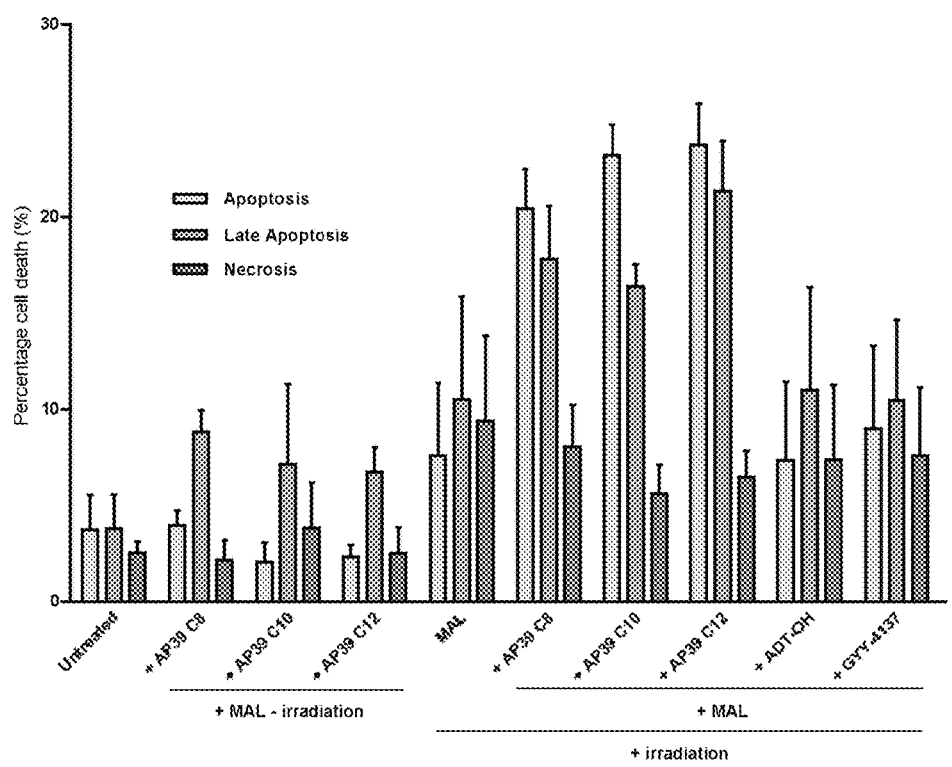
FIG. 2 shows modes of A431 cell death induced by photodynamic cell killing following treatment with MAL in the absence and presence of the slow release hydrogen sulfide donor ADT-OH and its mitochondrially targeted derivatives (AP39-C8, AP39-C10 and AP39-C12). Error bars represent one standard deviation, n=4.

Measurements of total cell death following treatment of the cells with ADT-OH and its AP39 derivatives have been plotted in FIG. 1, and a breakdown of the cell death types has been plotted in FIG. 2. Measurements of total cell death following treatment of the cells with 4-HTB and its AP123 derivatives have been plotted in FIG. 3, and a breakdown of the cell death types has been plotted in FIG. 4. The data for these experiments were collected at the same time but have been split up in order to present the results for ADT-OH and its AP39 derivatives and for 4-HTB and its AP123 derivatives in a clear way. As these experiments were carried out at the same time, data for the untreated controls, MAL, and GYY4137 is the same in FIGS. 1 and 3, and in FIGS. 2 and 4.

Figure 3:
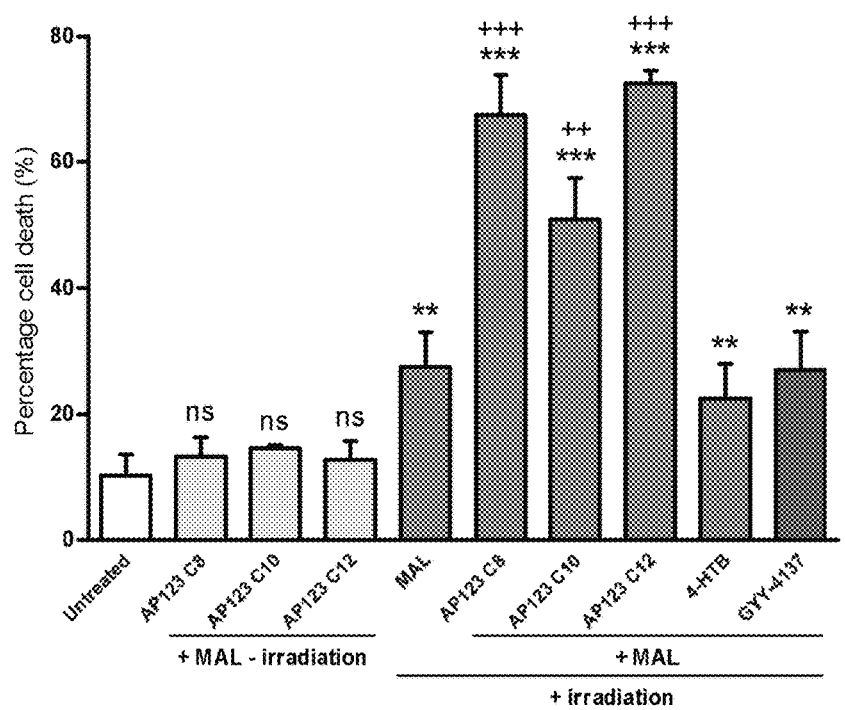
FIG. 3 shows percentage A431 cell death induced by photodynamic cell killing following treatment with MAL in the absence and presence of the slow release hydrogen sulfide donor 4-HTB and its mitochondrially targeted derivatives (AP123-C8, AP123-C10 and AP123-C12).

As can be seen from FIGS. 1 and 3, the mean cell death of the untreated control group was 10.1±3.4%.

Dark toxicity tests (without irradiation) of the ADT-OH derivatives found that these compounds did not induce any statistically significant changes in cell viability compared with the untreated control group. Cell death was found to be 14.9±2.3%, 12.1±4.9% and 11.7±1.5% for AP39-C8, AP39-C10 and AP39-C12, respectively (FIG. 1).

Dark toxicity tests (without irradiation) of the 4-HTB derivatives also found no statistically significant changes in cell viability compared with the untreated control group. Cell death was found to be 13.2±3.1%, 14.5±0.5% and 12.7±3.0% for AP123-C8, AP123-C10 and AP123-C12, respectively (see FIG. 3).

None of the SRHDs were toxic in the absence of irradiation, suggesting that they were well tolerated by A431 cells during the 5 h incubation.

Treatment with 1 mM MAL and irradiation in the absence of any SRHD resulted in 27.5±5.5% cell death ($p<0.01$ compared to untreated control) (see FIGS. 1 and 3).

Co-treatment with 1 mM MAL and irradiation in the presence of ADT-OH induced 25.7±6% ($p>0.05$ compared to MAL and irradiation) cell death (see FIG. 1).

Co-treatment with 1 mM MAL and irradiation in the presence of 4-HTB resulted in 22.5±5.5% ($p>0.05$ compared to MAL and irradiation) cell death (see FIG. 3).

A co-treatment of 1 mM MAL with GYY4137 did not significantly alter cell viability (27.1±6.0%, $p>0.05$) compared to treatment with MAL and irradiation (see FIGS. 1 and 3).

Co-treatment with 1 mM MAL and irradiation in the presence of the AP39 compounds induced 46.3±2.1% ($p<0.001$), 45.3±1.9% ($p<0.001$) and 51.6±3.2% ($p<0.001$) cell death for AP39-C8, AP39-C10 and AP39-C12, respectively.

Co-treatment with 1 mM MAL and irradiation in the presence of the AP123 compounds resulted in 67.5±6.4% ($p<0.001$), 50.9±6.5% ($p<0.01$) and 72.5±2.0% ($p<0.001$) cell death for AP123-C8, AP123-C10 and AP123-C12, respectively.

Treatment with MAL and irradiation in the absence of the SRHDs significantly increased cell death compared to untreated controls ($p<0.01$). The non-targeted $H_2S$ releasing moieties of AP39 (ADT-OH) and AP123 (4-HTB) had no statistically significant effect on photodynamic cell killing, exhibiting similar levels of cell death compared to MAL and irradiation only ($p>0.05$). GYY4137 was also found to have no effect on photodynamic cell killing ($p>0.05$). All derivatives of AP39 and AP123, however, significantly increased cell killing compared to MAL only with irradiation ($p<0.001$).

As mentioned above, FIGS. 2 and 4 show a breakdown of the cell death types. Annexin V-FITC and propidium iodide staining was used to assess the modes of cell death.

Treatment with 1 mM MAL and irradiation resulted in an increase in all types of cell death compared to untreated controls. Co-treatment with the AP39 derivatives primarily increased total cell death through increased early apoptosis, with smaller increases in late apoptosis. Necrotic cell death in the presence of AP39 derivatives appeared to decrease (see FIG. 2). The C8 and C10 AP123 derivatives increased total cell death through increases in early and late apoptosis, with little effect on necrosis. AP123-C12 had less effect on early apoptosis, instead increasing late apoptosis and necrosis (see FIG. 4). ADT-OH, 4-HTB and GYY4137 had no effect on the types of cell death observed compared to treatment with MAL and irradiation, with each treatment resulting in similar levels of early and late apoptosis and necrosis.

Further experiments were carried out to investigate the effects of irradiation on the release of $H_2S$ by $H_2S$ donors AP39-C10 and AP123-C10 in the absence and presence of PpIX. Experiments were carried out in a cell-free system and monitored by using the $H_2S$-sensitive fluorogenic probe WSP-1. The results of are set out in FIGS. 5 and 6.

As can be seen from FIGS. 5 and 6, prior to irradiation, $H_2S$ release by the C10 variants of AP39 and AP123 appears to be unaffected by the presence of PpIX. Irradiation of the donors in the absence of PpIX also does not have any significant effect on the release of $H_2S$. In the presence of PpIX, however, irradiation significantly increases the release of $H_2S$ by both AP39 and AP123 ($p<0.001$).

FIGS. 5 and 6 also show that the ADT-OH derivative AP123-C10 releases more $H_2S$ than the 4-HTB derivative AP39-C10.

EXAMPLE 1A

Mitochondria-Targeted Slow Release Hydrogen Sulfide Donors (SRHDs) Potentiate Methyl Aminolaevulinic Acid-Based Photodynamic Cell Killing The data covered in this Example build on the previously identified abilities of mitochondria-targeted hydrogen sulfide donors to potentiate methyl aminolaevulinic acid (MAL; Metvix®) photodynamic cell killing.

In short, these data show that the mitochondria-targeted derivatives of ADT-OH (AP39-C8, AP39-C10 and AP39-C12) and 4-HTB (AP123-C8, AP123-C10 and AP123-C12) are well tolerated across a large range of concentrations and only begin to exhibit cytotoxicity well outside of the "therapeutic" concentration. This tolerance is exhibited over periods relevant to the photodynamic experiments carried out (5 hours) and over prolonged periods of exposure (72 hours), suggesting the compounds are safe.

AP39-C10 and AP123-C10 exhibit a potentiating effect at concentrations as low as 10 nM, where a ~2-fold increase in cell killing is observed compared to the use of MAL alone. This is significantly more potent (5000-fold) than CP94 (50 µM) which exerts a similar degree of potentiation. The observed increases in total cell death were driven by increases in early and late apoptosis, with little-to-no effect on necrosis.

By measuring the effects of these compounds on MAL-induced protoporphyrin IX (PpIX) accumulation, it was possible to establish that these compounds do not exert their effects through the "traditional" method of increasing PpIX accumulation (which is how CP94 exerts its effects).

A small (but statistically significant) increase in mitochondrial oxidant generation was detected following photodynamic irradiation of cells co-treated with MAL and AP39-C10 or AP123-C10. This increase in oxidant generation appears to occur in a concentration-dependent manner.

FIG. 15—Dark Toxicity of Non-Targeted Slow Releasing Hydrogen Sulfide Donor ADT-OH and its Mitochondria-Targeted Derivatives, as Measured by the Viability of Treated A431 Cells A431 cells were treated with the non-targeted slow releasing hydrogen sulfide donor ADT-OH and its mitochondria-targeted derivatives (AP39-C8, AP39-C10 and AP39-C12) at a range of concentrations of each compound (0.1-500 µM), for 5 hours. Following this treatment, viability was measured using a resazurin-based fluorescence assay. The mean viability of the cells following treatment was calculated as a percentage of cell viability compared to the untreated controls.

The data in FIG. 15 show that treatment with each compound was well tolerated up to a concentration of 100 µM. At 500 µM, all compounds exhibited statistically significant cytotoxicity, with ADT-OH, AP39-C8, AP39-C10 and AP39-C12 decreasing viability to 76.7±1.3% ($p<0.01$), 20.1±4.5% ($p<0.001$), 59.3±13.3% ($p<0.05$) and 13.3±1.8% of untreated control ($p<0.01$), respectively.

FIG. 16—Dark Toxicity of Non-Targeted Slow Releasing Hydrogen Sulfide Donor 4-HTB and its Mitochondria-Targeted Derivatives, as Measured by the Viability of Treated A431 Cells A431 cells were treated with the non-targeted slow releasing hydrogen sulfide donor 4-HTB and its mitochondria-targeted derivatives (AP123-C8, AP123-C10 and AP123-C12) at a range of concentrations of each compound (0.1-500 µM), for 5 hours. Following this treatment, viability was measured using a resazurin-based fluorescence assay. The mean viability of the cells following treatment was calculated as a percentage of cell viability compared to the untreated controls.

The data in FIG. 16 show that treatment with each compound was well tolerated up to a concentration of 100 µM. 4-HTB was also tolerated up to 500 µM, whilst AP123-C8, AP123-C10 and AP123-C12 exhibited statistically significant cytotoxicity at this concentration, decreasing viability to 13.2±1.8% ($p<0.001$), 62.6±9.1% ($p<0.05$) and 17.0±0.7% of untreated control ($p<0.001$), respectively.

FIG. 17—Viability of A431 Cells Following Treatment with AP39-C10 and AP123-C10 for 72 Hours: AP39-C10 and AP123-C10 Did not Induce Significant Cytotoxicity in A431 Cells Following a 72 Hour Treatment with Selected "Therapeutic" Concentrations To ensure that these compounds were not toxic at selected "therapeutic" concentrations during prolonged treatment, A431 cells were treated with a range of concentrations (0-1000 nM) of each of AP39-C10 and AP123-C10 for 72 hours, after which viability was assessed using a resazurin-based fluorescence assay. A positive control, where cells were treated with 30 µM etoposide for 24 hours was also carried out.

The mean viability of the cells following treatment was calculated as a percentage of viability compared to the untreated controls (0 nM—AP39-C10; 100.0±2.6%, AP123-C10; 100.0±5.4%).

The data in FIG. 17 show that, over 72 hours, treatment with AP39-C10 and AP123-C10 was well tolerated at each concentration tested. When treated with 1000 nM AP39-C10, cell exhibited a small, but statistically significant, decrease in viability (94.1±2.6%, $p<0.05$ c.f. control). A positive control, where cells were treated with the chemotherapeutic agent etoposide (30 µM), significantly decreased cell viability ($p<0.001$ c.f. control).

FIG. 18—A431 Cell Death Induced by Photodynamic Cell Killing Following Treatment with MAL in the Absence and Presence of the Slow Release Hydrogen Sulfide Donors AP39-C10 and AP123-C10: AP39-C10 and AP123-C10 Significantly Increase MAL-Based Photodynamic Cell Killing A431 cells were treated concurrently with AP39-C10 or AP123-C10 (10, 100 or 1000 nM) for 5 hours and MAL (1 mM) for 3 hours, after which cells were irradiated for 5 minutes (630 nm, 25 J/cm$^2$) and then incubated for further 3 hours. Cell viability was then assessed by annexin V-FITC and propidium iodide staining in conjunction with flow cytometry. Co-treatment with CP94 (50 µM) (a clinically used iron chelator) was used as a positive control and for comparison. Results are set out in FIG. 18.

The mean cell death of the untreated control group was 13.8±1.6%. Treatment with 1 mM MAL in the absence of any SRHD resulted in a significant increase in cell death (32.8±2.5%, $p<0.001$ c.f. control). Carrying out photodynamic treatment with 1 mM MAL in the presence of 10, 100 or 1000 nM of AP39-C10 resulted in further increases in cell death, with 50.7±3.1% ($p<0.001$ c.f. MAL), 53.1±2.3% ($p<0.001$) and 50.2±4.9% ($p<0.001$) cell death, respectively.

Photodynamic treatment with 1 mM MAL in the presence of 10, 100 or 1000 nM of AP123-C10 also resulted in further increases in cell death, with 57.2±1.3% ($p<0.001$ c.f. MAL alone), 56.5±2.7% ($p<0.001$ c.f. MAL alone) and 66.7±5.6% ($p<0.001$ c.f. MAL alone) cell death, respectively.

FIG. 19—Modes of A431 Cell Death Induced by Photodynamic Cell Killing Following Treatment with MAL in the Absence and Presence of the Slow Release Hydrogen Sulfide Donors AP39-C10 and AP123-C10: AP39-C10 and AP123-C10 Significantly Increase MAL-Based Photodynamic Cell Killing Through Selective Promotion of Apoptotic Cell Death Annexin V-FITC and propidium iodide staining was used to assess the modes of cell death following irradiation of A431 cells treated with 1 mM MAL in absence and presence of AP39-C10 or AP123-C10 (10, 100 or 1000 nM). Co-treatment with CP94 (50 μM) was used as a positive control and for comparison. Results are set out in FIG. 19.

Photodynamic irradiation of A431 cells pre-treated with 1 mM MAL resulted in an increase in all types of cell death compared to the untreated controls. Co-treatment with AP39-C10 or AP123-C10 at 10, 100 or 1000 nM resulted in a further increase in apoptosis and late apoptosis, with no apparent effect on necrotic cell death.

FIG. 20—PpIX Accumulation in A431 Cells Following Treatment with MAL in the Absence and Presence of Non-Targeted and Mitochondria-Targeted Slow-Releasing Hydrogen Sulfide Donors: Slow Releasing Hydrogen Sulfide Donors Did not Increase MAL-Induced Protoporphyrin IX Accumulation A431 cells were treated concurrently with slow-releasing hydrogen sulfide donors (1 μM) for 5 hours and MAL (1 mM) for 3 hours, after which PpIX accumulation was measured by fluorescence plate reader (excitation 410 nm, excitation 630 nm). Co-treatment with CP94 (50 μM) was used as a positive control and for comparison.

The effects of ADT-OH, 4-HTB and their mitochondria-targeted derivatives (1 μM) on PpIX accumulation were investigated. The data presented in FIG. 20 show the measured relative fluorescence of PpIX. 1 mM MAL significantly increased PpIX accumulation compared to untreated controls ($p<0.001$). In sharp contrast to CP94 (an iron chelator and well-known enhancer of PpIX accumulation used clinically), none of the slow-releasing hydrogen sulfide donors exhibited any effects on PpIX accumulation ($p>0.05$ c.f. 1 mM MAL) e.g. inhibition or further accumulation. CP94 significantly increased PpIX accumulation compared to 1 mM MAL alone ($p<0.001$).

FIG. 21—the Effects of AP39-C10 on MAL-Induced PpIX Accumulation in A431 Cells: AP39-C10 had No Effect on MAL-Induced Protoporphyrin IX Accumulation A431 cells were treated concurrently with AP39-C10 (10, 100 or 1000 nM) for 5 hours and MAL (1 mM) for 3 hours, after which PpIX accumulation was measured by fluorescence plate reader (excitation 410 nm, excitation 630 nm). Co-treatment with CP94 (50 μM) was used as a positive control and for comparison.

The effects of AP39-C10 (10, 100 and 1000 nM) on PpIX accumulation were investigated. The data presented in FIG. 21 show the measured relative fluorescence of PpIX. 1 mM MAL significantly increased PpIX accumulation compared to untreated controls ($p<0.001$). AP39-C10 had no effect on PpIX accumulation across any of the tested concentrations ($p>0.05$ c.f. 1 mM MAL). A positive control, the iron chelator CP94, significantly increased PpIX accumulation compared to 1 mM MAL alone ($p<0.001$).

FIG. 22—the Effects of AP123-C10 on MAL-Induced PpIX Accumulation in A431 Cells: AP123-C10 had No Effect on MAL-Induced Protoporphyrin IX Accumulation A431 cells were treated concurrently with AP123-C10 (10, 100 or 1000 nM) for 5 hours and MAL (1 mM) for 3 hours, after which PpIX accumulation was measured by fluorescence plate reader (excitation 410 nm, excitation 630 nm). Co-treatment with CP94 (50 μM) was used as a positive control and for comparison.

The effects of AP123-C10 (10, 100 and 1000 nM) on PpIX accumulation were investigated. The data presented in FIG. 22 show the measured relative fluorescence of PpIX. 1 mM MAL significantly increased PpIX accumulation compared to untreated controls ($p<0.001$). AP123-C10 had no effect on PpIX accumulation across any of the tested concentrations ($p>0.05$ c.f. 1 mM MAL). A positive control, the iron chelator CP94, significantly increased PpIX accumulation compared to 1 mM MAL alone ($p<0.001$).

FIG. 23—the Effects of AP39-C10 on Reactive Oxygen Species Generation During Photodynamic Irradiation of A431 Cells Pre-Treated with MAL: AP39-C10 Increases Mitochondrial Oxidant Generation During MAL-Based Photodynamic Cell Killing A431 cells were treated concurrently with AP39-C10 (10, 100 or 1000 nM) for 5 hours, MAL (1 mM) for 3 hours and MitoSOX (2.5 μM) for 1 hour, after which they were irradiated for 5 min (630 nm, 25 J/cm$^2$) and MitoSOX (mito-2-OH-E$^+$) fluorescence, indicative of mitochondrial oxidant production, was immediately analysed by flow cytometry. Results are set out in FIG. 23.

Mitochondria-targeted dihydroethidium (i.e. MitoSOX) was used to assess the production of mitochondrial reactive oxygen species (ROS) by PpIX photochemical reactions and to determine the effects of AP39-C10 on this process. All of the results are represented as a percentage of the untreated controls (100.0±8.5%). The fluorescence of the photoirradiated cells, which had been pre-treated with MAL, was 193.7±7.3% ($p<0.001$ c.f. untreated controls). Co-treatment of MAL with 10 nM AP39-C10 resulted in a small, statistically non-significant, increase in this fluorescence to 207.3±10.7% ($p>0.05$ c.f. MAL). Co-treatment of MAL with 100 or 1000 nM AP39-C10 resulted in significant increases to 227.1±3.5% ($p<0.001$) and 214.3±6.4% ($p<0.001$).

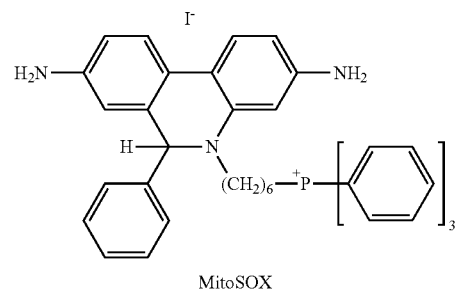

MitoSOX

FIG. 24—the Effects of AP123-C10 on Reactive Oxygen Species Generation During Photodynamic Irradiation of A431 Cells Pre-Treated with MAL: AP123-C10 Increases Mitochondrial Oxidant Generation During MAL-Based Photodynamic Cell Killing A431 cells were treated concurrently with AP123-C10 (10, 100 or 1000 nM) for 5 hours, MAL (1 mM) for 3 hours and MitoSOX (2.5 μM) for 1 hour, after which they were irradiated for 5 min (630 nm, 25 J/cm$^2$) and MitoSOX (mito-2-OH-E$^+$) fluorescence, indicative of mitochondrial oxidant production, was immediately analysed by flow cytometry. Results are set out in FIG. 24.

Mitochondria-targeted dihydroethidium was used to assess the production of mitochondrial reactive oxygen species (ROS) by PpIX photochemical reactions and to determine the effects of AP123-C10 on this process. All of the results are represented as a percentage of the untreated controls (100.0±5.4%). The fluorescence of the photoirradiated cells, which had been pre-treated with MAL, was 220.1±8.5% ($p<0.001$ c.f. untreated controls). Co-treatment of MAL with 10, 100 or 1000 nM AP123-C10 resulted in significant increases in this fluorescence to 237.4±8.2% ($p<0.01$ c.f. MAL), 245.3±10.6% ($p<0.01$) and 248.1±15.1% ($p<0.01$), respectively.

EXAMPLE 2

Effects of Thioredoxin Reductase Inhibitors on Photodynamic Cell Killing

Compounds Tested

The effects of thioredoxin reductase inhibitors on photodynamic cell killing were investigated by using the thioredoxin reductase inhibitors auranofin and 2,4-dinitrochlorobenzene (DNCB), which have the following structures:

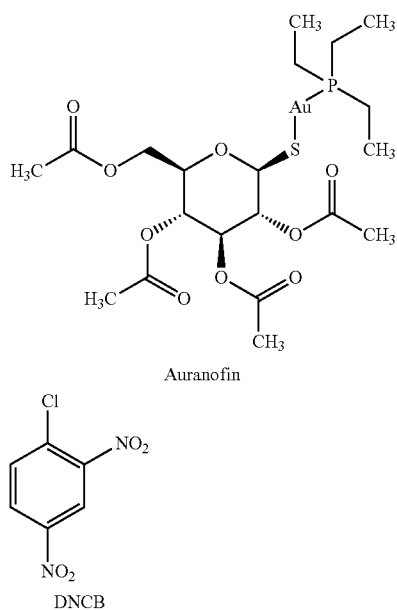

Auranofin

DNCB

Auranofin is commercially available from Sigma Aldrich and Enzo Life Sciences.

DNCB is commercially available from Sigma Aldrich.

Toxicity of Thioredoxin Reductase Inhibitors Auranofin and 2,4-Dinitrochlorobenzene (DNCB)

Initial experiments were carried out to establish the toxicity of auranofin and DNCB under 2% $O_2$ as measured using a resazurin oxidation assay, to provide an estimation of viability based on cellular metabolic activity.

A431 cells were treated with 1 mM MAL±DNCB (0-50 µM) for 3 hours, after which cell viability was measured using a resazurin-based fluorescence assay (FIG. 7). The mean viability of cells following treatment was calculated as a percentage of viability compared to the untreated control cells (100.0±11.1%). Treatment with DNCB at concentrations of 1, 5 and 10 µM did not significantly affect cell viability, with 97.4±6.9%, 99.4±7.3% and 98.6±6.2% viability, respectively. In the presence of DNCB at a concentration of 25 µM cell viability statistically significantly decreased to 79.0±4.3% (p<0.01) and 50 µM DNCB decreased viability further, to 57.7±1.4% (p<0.001).

A431 cells were treated with 1 mM MAL±auranofin (0-2000 nM) for 3 hours, after which cell viability was measured using a resazurin-based fluorescence assay (FIG. 8). The mean viability of cells following treatment was calculated as a percentage of viability compared to the untreated control cells (100.0±8.2%). Cells treated with 100, 250, 500, 1000 and 2000 nM auranofin exhibited 95.8±3.6%, 96.7±7.8%, 96.2±3.7%, 100.0±6.1% and 100.1±5.9% viability, respectively. None of these results were statistically significantly different compared to untreated control cells.

From these experiments, concentrations of 100 nM auranofin and 10 µM DNCB were chosen for further experimentation.

The Effects of Co-Treatment with Thioredoxin Reductase Inhibitors DNCB or Auranofin on MAL-Based Photodynamic Cell Killing A431 cells were treated with 1 mM MAL in absence and presence of auranofin (100 nM) or DNCB (10 µM) for 3 h, after which cells were irradiated for 5 min (630 nm, 25 $J/cm^2$) and then incubated for further 3 h, so A431 cell viability was assessed 3 hours post-irradiation. Viability was assessed by annexin V-FITC and propidium iodide staining in conjunction with flow cytometry.

Measurements of total cell death following treatment of the cells with MAL in the absence and presence of the thioredoxin reductase inhibitors auranofin or DNCB have been plotted in FIG. 9. The mean cell death of the untreated control group was 9.0±2.0%.

Treatment with 1 mM MAL and irradiation in the absence of co-treatment resulted in 32.5±3.6% cell death; a statistically significant increase compared to untreated controls (p<0.001).

Co-treatment with 1 mM MAL, 10 µM DNCB or 100 nM auranofin and irradiation resulted in 46.3±4.0% and 65.5±1.7% cell death, respectively. In the presence of 10 µM DNCB, photodynamic cell killing was significantly increased compared to MAL and irradiation only (p<0.01). In the presence of 100 nM auranofin, cell killing was also significantly increased compared to MAL and irradiation only (p<0.001). Auranofin also increased cell killing more than DNCB (p<0.001), indicating that its sensitising effects are considerably more potent than DNCB as a greater effect was observed using a concentration 100 times lower.

A breakdown of A431 cell death for each treatment has been plotted in FIG. 10. Annexin V-FITC and propidium iodide staining was used to assess the modes of cell death.

Treatment with 1 mM MAL and irradiation resulted in an increase in all types of cell death compared to untreated controls.

Co-treatment with either DNCB or auranofin followed by irradiation primarily increased necrotic cell death (propidium iodide staining) compared to 1 mM MAL and irradiation. Co-treatment with auranofin also slightly increased late apoptotic cell death compared to 1 mM MAL and irradiation.

EXAMPLE 2A

Thioredoxin Reductase Inhibitors and Thioredoxin Inhibitors Potentiate Methyl-Aminolaevulinic Acid-Based Photodynamic Cell Killing The data covered in this Example build on the previously identified abilities of inhibitors of the thioredoxin antioxidant system to potentiate methyl-aminolaevulinic acid (MAL; Metvix®) photodynamic cell killing.

This work includes the use of compounds known as gold (I) thiolates, which covers auranofin (AUR), aurothiomalate (ATM) and aurothioglucose (ATG) as well as an alkylating agent, dinitrochlorobenzene (DNCB). These 4 compounds are known to inhibit thioredoxin reductase. Additionally, the thioredoxin inhibitor PX12 (2-[(1-Methylpropyl)dithio]-1H-imidazole) has been investigated.

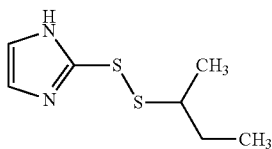

PX12

These data show that each of the inhibitors are well tolerated across a large range of concentrations and only begin to exhibit cytotoxicity outside of the "therapeutic" concentration. This tolerance is exhibited over periods relevant to the photodynamic experiments carried out (24 hours), suggesting the compounds are safe at the concentrations carried forward into further investigation.

DNCB exhibits a mild potentiating effect, whilst AUR, ATM, ATG and PX12 exhibit a more robust potentiating effect. The observed increases in total cell death were driven by increases in late apoptosis and necrosis, with little-to-no effect on early apoptosis. Further investigation revealed that the potentiating effects of AUR are concentration-dependent and a concentration of 100 nM exerted a similar degree of potentiation as CP94 (50 µM), making AUR 500-fold more potent.

By measuring the effects of these compounds on MAL-induced protoporphyrin IX (PpIX) accumulation, it was possible to establish that none of the inhibitors of the thioredoxin antioxidant system exert their effects through the "traditional" method of increasing PpIX accumulation (which is how CP94 exerts its effects).

A significant increase in mitochondrial oxidant generation was detected following photodynamic irradiation of cells co-treated with MAL and each of the inhibitors, providing a mechanism by which these potentiating effects are exerted.
Key:
AUR=auranofin
ATM=aurothiomalate
ATG=aurothioglucose
DNCB=dichloronitrobenzene
FIG. 25—Dark Toxicity of Thioredoxin Reductase Inhibitors and Thioredoxin Inhibitors, as Measured by the Viability of Treated A431 Cells A431 cells were treated with either one of the gold (I) thiolates auranofin (AUR), aurothiomalate (ATM) or aurothioglucose (ATG), the alkylating agent dichloronitrobenzene (DNCB) or the thioredoxin inhibitor PX12 for 24 hours with a range of concentrations of each compound (0.1-50 µM AUR; 0.1-500 µM ATG and ATM; 0.5-100 µM DNCB and PX12). Following treatment, cell viability was measured using a resazurin-based fluorescence assay. The mean viability of the cells following treatment was calculated as a percentage of cell viability compared to the untreated controls.

The data in FIG. 25 show that both ATM and ATG were well tolerated at all concentrations tested. ATG exhibited a small (but statistically significant) increase in cytotoxicity at 500 µM (95.2±4.4%, p<0.01). AUR was generally well tolerated up to a concentration of 10 µM. AUR exhibited a small (but statistically significant) increase in cytotoxicity at 1 (90.6±2.6%, p<0.05 c.f. untreated control) and 5 µM (87.1±2.4%, p<0.05). At 50 µM there was an almost complete loss of cell viability, with only 15.5±2.4% (p<0.001) viability compared to untreated control.

DNCB exhibited no cytotoxicity at concentrations up to 10 µM. At 50 µM and 100 µM DNCB induced significant cytotoxicity, with 11.7±0.8% (p<0.01 c.f. untreated control) and 14.8±4.2% (p<0.01) viability, respectively. PX12 was also well tolerated, with no cytotoxicity observed up to a concentration of 100 µM. At 500 µM there was a significant increase in cytotoxicity, with 47.5±4.9% (p<0.01 c.f. untreated control) cell viability.

FIG. 26—A431 Cell Death Induced by Photodynamic Cell Killing Following Treatment with MAL in the Absence and Presence of Thioredoxin Antioxidant System Inhibitors: Thioredoxin Reductase Inhibitors and Thioredoxin Inhibitors Significantly Increase MAL-Based Photodynamic Cell Killing A431 cells were treated with MAL (1 mM) in the absence and presence of the thioredoxin antioxidant system inhibitors AUR (1 µM), ATM (20 µM), ATG (20 µM), DNCB (10 µM) or PX12 (10 µM) for 3 hours, after which cells were irradiated for 5 minutes (630 nm, 25 J/cm$^2$) and then incubated for further 3 hours. Cell viability was assessed by annexin V-FITC and propidium iodide staining in conjunction with flow cytometry. Results are set out in FIG. 26.

The mean cell death of the untreated control group was 9.3±1.2%. Photo-irradiation of cells treated with MAL in the absence of any inhibitor resulted in a significant increase in cell death (29.1±3.8%, p<0.001 c.f. control).

Photo-irradiation of A431 cells with MAL and thioredoxin antioxidant system inhibitors lead to a significant increase in cell death compared to MAL alone. Gold (I) thiolates ATM and ATG increased cell death to 66.7±4.9% (p<0.001 c.f. MAL alone) and 58.7±0.8% (p<0.001), respectively. AUR increased cell death to 61.3±3.3% (p<0.001) compared to MAL alone. The thioredoxin inhibitor, PX12, increased cell death to 70.5±4.5% (p<0.001 c.f. MAL alone) and the alkylating agent, DNCB, increased cell death to 43.8±3.9% (p<0.01).

FIG. 27—Modes of A431 Cell Death Induced by Photodynamic Cell Killing Following Treatment with MAL in the Absence and Presence of Thioredoxin Reductase Inhibitors and Thioredoxin Inhibitors: Thioredoxin Reductase Inhibitors and Thioredoxin Inhibitors Significantly Increase MAL-Based Photodynamic Cell Killing Through Promotion of Primarily Apoptotic Cell Death Annexin V-FITC and propidium iodide staining was used to assess the modes of cell death following irradiation of A431 cells treated with MAL (1 mM) in the absence and presence of AUR (1 µM), ATM (20 µM), ATG (20 µM), DNCB (10 µM) or PX12 (10 µM). Results are set out in FIG. 27.

Photodynamic irradiation of A431 cells pre-treated with MAL (1 mM) resulted in an increase in all types of cell death compared to the untreated controls. Co-treatment of MAL with the thioredoxin system inhibitors resulted in further increases in cell death, primarily late apoptosis and necrosis, with little effect on apoptotic cell death.

FIG. 28—A431 Cell Death Induced by Photodynamic Cell Killing Following Treatment with MAL in the Absence and Presence of Different Concentrations of Auranofin (AUR): Auranofin, Another Thioredoxin Reductase Inhibitor, Potentiates MAL-Induced Photodynamic Cell Killing in a Concentration-Dependent Manner A431 cells were treated with MAL (1 mM) in the absence and presence of different concentrations of AUR (10, 100 or 1000 nM) for 3 hours, after which cells were irradiated for 5 minutes (630 nm, 25 J/cm$^2$) and then incubated for further 3 hours. Cell viability was assessed by annexin V-FITC and propidium iodide staining in conjunction with flow cytometry. Results are set out in FIG. 28.

The mean cell death of the untreated control group was 9.3±1.2%.

The data show that treatment with MAL alone resulted in a significant increase in cell death (29.1±3.8%, p<0.01 c.f. untreated control). Co-treatment of A431 cells with MAL and 10 nM lead to a small (non-significant) increase in cell death (35.3±4.2%, p>0.05 c.f. MAL alone). Co-treatment of MAL with AUR at concentration of 100 or 1000 nM lead to statistically significant increases in cell death compared to MAL alone, with 56.7±6.3% (p<0.001) and 61.3±3.3% (p<0.001) cell death observed, respectively.

FIG. 29—Modes of A431 Cell Death Induced by Photodynamic Cell Killing Following Treatment with MAL in the Absence and Presence of Different Concentrations of Auranofin (AUR): Auranofin Potentiates MAL-Induced Photodynamic Cell Killing in a Concentration-Dependent Manner Through Promotion of Apoptotic and Necrotic Cell Death Annexin V-FITC and propidium iodide staining was used to assess the modes of cell death following irradiation of A431 cells treated with MAL (1 mM) in the absence and presence of AUR (10, 100 and 1000 nM). Results are set out in FIG. 29.

Photodynamic irradiation of A431 cells pre-treated with MAL (1 mM) resulted in an increase in all types of cell death compared to the untreated controls. Co-treatment with AUR lead to concentration-dependent increases in late apoptosis and necrosis, with little effect on early apoptosis.

FIG. 30—PpIX Accumulation in A431 Cells Following Treatment with MAL in the Absence and Presence of Thioredoxin Antioxidant System Inhibitors: Thioredoxin Reductase Inhibitors and Thioredoxin Inhibitors Did not Increase MAL-Induced Protoporphyrin IX Accumulation A431 cells were treated concurrently with MAL (1 mM) in the absence and presence of AUR (1 µM), ATM (20 µM), ATG (20 µM), DNCB (10 µM) or PX12 (10 µM) for 3 hours, after which PpIX accumulation was measured by fluorescence plate reader (excitation 410 nm, excitation 630 nm). CP94 (50 µM) was used as a positive control and for comparison. Results are set out in FIG. 30.

The effects of thioredoxin antioxidant system inhibitors, AUR (1 µM), ATM (20 µM), ATG (20 µM), DNCB (10 µM) and PX12 (10 µM) on PpIX accumulation were investigated. The data presented in FIG. 30 show the measured relative fluorescence of PpIX. MAL (1 mM) significantly increased PpIX accumulation compared to untreated controls (p<0.001). In sharp contrast to CP94 (an iron chelator and well-known enhancer of PpIX accumulation used clinically), none of the thioredoxin antioxidant system inhibitors tested exhibited any effects on PpIX accumulation (p>0.05 c.f. 1 mM MAL) e.g. inhibition or further accumulation. CP94 significantly increased PpIX accumulation compared to MAL alone (p<0.001).

FIG. 31—the Effects of Thioredoxin Antioxidant System Inhibitors on Reactive Oxygen Species Generation During Photodynamic Irradiation of A431 Cells Pre-Treated with MAL: Thioredoxin Reductase Inhibitors and Thioredoxin Inhibitors Increase Mitochondrial Oxidant Generation During MAL-Based Photodynamic Cell Killing A431 cells were treated concurrently with MAL (1 mM) in the absence and presence of AUR (1 µM), ATM (20 µM), ATG (20 µM), DNCB (10 µM) or PX12 (10 µM) for 3 hours and MitoSOX (2.5 µM) for 1 hour, after which they were irradiated for 5 min (630 nm, 25 J/cm$^2$) and MitoSOX (mito-2-OH-E$^+$) fluorescence, indicative of mitochondrial oxidant production, was immediately analysed by flow cytometry. Results are set out in FIG. 31.

Mitochondria-targeted dihydroethidium was used to assess the production of reactive oxygen species (ROS) by PpIX photochemical reactions and to determine the effects of thioredoxin reductase inhibitors and thioredoxin inhibitors on this process. All of the results are represented as a percentage of untreated cells (100.0±4.3%).

The fluorescence of the photoirradiated cells, which had been pre-treated with MAL alone, was 143.3±4.8% (p<0.001 c.f. untreated controls). Co-treatment of MAL with AUR (1 µM) resulted in a further increase in MitoSOX fluorescence to 182.6±8.3% (p<0.001, c.f. MAL alone). ATM and ATG also significantly increased MitoSOX fluorescence to 192.4±5.6% (p<0.001) and 184.9±5.9% (p<0.001), respectively.

Co-treatment of MAL with DNCB also increased MitoSOX fluorescence to 209.5±3.2% (p<0.001, c.f. MAL alone) and PX12 increased fluorescence to 211.4±17.6% (p<0.001).

EXAMPLE 3

Effects of Nitroxides on Photodynamic Cell Killing

Compounds Tested

The effects of nitroxides on photodynamic cell killing were investigated by using the nitroxides TEMPO and TEMPOL, which have the following structures:

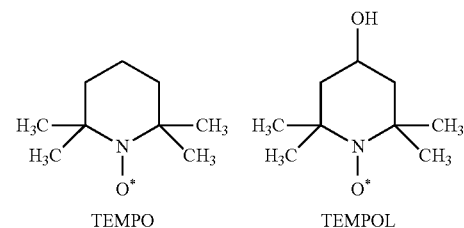

TEMPO       TEMPOL

TEMPO (2,2,6,6-tetramethyl-1-piperidinyloxy) is commercially available from Sigma Aldrich and Enzo Life Sciences.

TEMPOL (4-hydroxy-2,2,6,6-tetra methylpiperidine 1-oxyl) is commercially available from Sigma Aldrich and Enzo Life Sciences.

Toxicity of Nitroxides TEMPO and TEMPOL

A431 cells were treated with 1 mM MAL±TEMPOL or TEMPO (0-10 mM) for 3 hours, after which cell viability was measured using a resazurin-based fluorescence assay (FIG. 11). The mean viability of cells following treatment was calculated as a percentage of viability compared to the untreated control cells (TEMPOL—100.0±5.5% and TEMPO—100.0±3.1%).

Treatment with TEMPOL at concentrations of 0.25, 0.5, 1 or 2 mM did not significantly affect cell viability, with 99.3±4.4%, 102.0±3.6%, 99.8±2.9% and 104.2±3.3%, respectively. Similarly, viability of cells treated with TEMPO over the same range was 97.8±3.4%, 97.5±1.7%, 98.6±6.8% and 97.4±6.2%, respectively.

Treatment with 5 mM TEMPOL resulted in a statistically significant increase in viability, to 116.2±2.7% (p<0.01), whilst 10 mM resulted in significant decrease in viability, to 77.8±4.7% (p<0.001). Treatment with 5 and 10 mM TEMPO led to significant decreases in viability, with 92.9±6.6% (p<0.05) and 79.9±8.5% (p<0.01), respectively.

The Effects of Co-Treatment with Nitroxides TEMPO or TEMPOL on MAL-Based Photodynamic Cell Killing A431 cells were treated with 1 mM MAL in absence and presence of TEMPO (1 mM) or TEMPOL (1 mM) for 3 h, after which cells were irradiated for 5 min (630 nm, 25

J/cm²) and then incubated for further 3 h, so A431 cell viability was assessed 3 hours post-irradiation. Viability was assessed by annexin V-FITC and propidium iodide staining in conjunction with flow cytometry.

Measurements of total cell death following treatment of the cells with MAL in the absence and presence of TEMPO or TEMPOL have been plotted in FIG. 12. The mean cell death of the untreated control group was 10.7±2.3%.

Treatment with 1 mM MAL and irradiation alone (in the absence of co-treatment) resulted in 34.4±3.2% cell death; a statistically significant increase compared to untreated control ($p<0.001$).

Co-treatment with 1 mM MAL, 1 mM TEMPO or 1 mM TEMPOL and irradiation resulted in 52.0±8.3% and 50.8±6.8% cell death, respectively. These increases in cell death were statistically significant compared to untreated control ($p<0.001$) and 1 mM MAL and irradiation ($p<0.001$).

A breakdown of A431 cell death for each treatment has been plotted in FIG. 13. Annexin V-FITC and propidium iodide staining was used to assess the modes of cell death.

Treatment with MAL and irradiation resulted in an increase in all types of cell death compared to untreated controls.

Co-treatment with TEMPO resulted in an increase in apoptotic and late apoptotic cell death, whilst co-treatment with TEMPOL resulted in an increase in late apoptotic and necrotic cell death.

Further experiments were carried out to investigate the effects of TEMPOL and TEMPO on MAL-induced PpIX accumulation. A431 cells were treated with 1 mM MAL in absence and presence of TEMPOL or TEMPO (0.01-1 mM) for 3 h, after which PpIX accumulation was measured by fluorescence plate reader (excitation 410 nm, excitation 630 nm). FIG. 3.17 shows the measured relative fluorescence of PpIX. As the concentration of TEMPOL or TEMPO was increased, a corresponding increase in PpIX fluorescence was detected. TEMPOL and TEMPO at 0.01 mM increased PpIX fluorescence slightly, but this was not statistically significant. At 0.1 mM and 1 mM, TEMPOL significantly increased PpIX accumulation further ($p<0.05$ and $p<0.001$, respectively). Similar results were observed with TEMPOL at 0.1 mM and 1 mM ($p<0.05$ and $p<0.01$, respectively). With both antioxidants, addition of 1 mM resulted in a ~2-fold increase in PpIX fluorescence.

EXAMPLE 3A

Nitroxides Potentiate Methyl-Aminolaevulinic Acid-Based Photodynamic Cell Killing The data covered in this Example builds on the previously identified abilities of a class of stable radicals, known as nitroxides, to potentiate methyl-aminolaevulinic acid (MAL; Metvix®) photodynamic cell killing.

In short, these data show that several nitroxides are well tolerated across a large range of concentrations and only begin to exhibit cytotoxicity outside of the "therapeutic" concentration. This tolerance is exhibited over periods relevant to the photodynamic experiments carried out (24 hours), suggesting the compounds are safe at the concentrations carried forward into further investigation.

TEMPONE exhibits a mild potentiating effect, whilst TEMPO and TEMPOL exhibit a more robust potentiating effect. The observed increases in total cell death were driven by increases in late apoptosis and necrosis, with little-to-no effect on early apoptosis. The mitochondria-targeted nitroxide, MitoTEMPO also exhibited a potentiating effect, equivalent to the non-targeted TEMPO at a concentration 20-fold lower. Further investigation with TEMPOL revealed that these potentiating effects are concentration-dependent.

By measuring the effects of these compounds on MAL-induced protoporphyrin IX (PpIX) accumulation, it has been established that all tested nitroxides significantly increased PpIX accumulation in a concentration-dependent manner. Previous work has highlighted that this effect is not elicited through iron chelation (which is how CP94 exerts its effects), but rather through iron oxidation. MitoTEMPO was also found to be 20-fold more potent than TEMPO at increasing PpIX accumulation (to equivalent levels), supporting observations made when measuring effects on photodynamic cell killing.

Significant increases in mitochondrial oxidant generation were detected following photodynamic irradiation of cells co-treated with MAL and each of the nitroxides.

Further investigation with TEMPOL revealed that this increase in oxidant generation appears to occur in a concentration-dependent manner.

Whilst the potentiating effect of these nitroxides is observed at concentrations greater than CP94 (50 μM) which exerts a similar degree of potentiation, this work has established a novel mechanism by which the efficacy of PpIX-based photodynamic cell killing could be increased. Furthermore, we have established that targeting a nitroxide to the mitochondria is a valid method by which potency can be significantly increased.

FIG. 32—Dark Toxicity of Nitroxides, as Measured by the Viability of Treated A431 Cells A431 cells were treated with the nitroxides TEMPOL, TEMPONE, TEMPO and its mitochondria-targeted derivative, MitoTEMPO for 24 hours with a range of concentrations of each compound (0.1-50 mM TEMPOL, TEMPONE, TEMPONE; 0.5-500 μM MitoTEMPO), after which cell viability was measured using a resazurin-based fluorescence assay. The mean viability of the cells following treatment was calculated as a percentage of cell viability compared to the untreated controls.

The data in FIG. 32 show that treatment with Mito-TEMPO was well tolerated up to a concentration of 100 μM. At 500 μM, a small but statistically significant decrease in cell viability was observed (86.5±1.6%, $p<0.01$ c.f. control). TEMPONE and TEMPO did not exhibit any cytotoxicity up to a concentration of 5 mM. At higher concentrations, TEMPONE and TEMPO showed significant cytotoxicity, with 80.3±13.3% ($p=0.05$ c.f. control) and 64.9±0.1% ($p<0.01$) of untreated cells at 10 mM and 53.7±13.3% ($p=0.01$) and 8.5±0.2% ($p<0.001$) of untreated cells at 50 mM, respectively.

FIG. 33—A431 Cell Death Induced by Photodynamic Cell Killing Following Treatment with MAL in the Absence and Presence of Nitroxides: Nitroxides Significantly Increase MAL-Based Photodynamic Cell Killing A431 cells were treated with 1 mM MAL in the absence and presence of TEMPOL (1 mM) TEMPONE (1 mM), TEMPO (1 mM) or MitoTEMPO (50 μM) for 3 hours, after which cells were irradiated for 5 minutes (630 nm, 25 J/cm²) and then incubated for further 3 hours. Cell viability was assessed by annexin V-FITC and propidium iodide staining in conjunction with flow cytometry. Results are set out in FIG. 33.

The mean cell death of the untreated control group was 11.7±3.4%. Treatment with 1 mM MAL in the absence of any nitroxide resulted in a significant increase in cell death (26.8±1.9%, $p<0.001$ c.f. control). Co-treatment of A431 cells with MAL and TEMPOL, TEMPONE or TEMPO lead to statistically significant increases in cell death compared to MAL alone, with 69.3±3.1% ($p<0.001$), 37.9±2.3% ($p<0.001$) and 46.3±3.6% ($p<0.001$) cell death observed, respectively. Co-treatment with MitoTEMPO also lead to a statistically significant increase in cell death (43.3±7.7%, $p<0.01$) compared to MAL alone.

FIG. 34—Modes of A431 Cell Death Induced by Photodynamic Cell Killing Following Treatment with MAL in the Absence and Presence of Nitroxides: Nitroxides Significantly Increase MAL-Based Photodynamic Cell Killing Through Promotion of Apoptotic and Necrotic Cell Death Annexin V-FITC and propidium iodide staining was used to assess the modes of cell death following irradiation of A431 cells treated with MAL (1 mM) in absence and presence of the nitroxides TEMPOL (1 mM), TEMPONE (1 mM), TEMPO (1 mM) and MitoTEMPO (50 μM). Results are set out in FIG. 34.

Photodynamic irradiation of A431 cells pre-treated with 1 mM MAL resulted in an increase in all types of cell death compared to the untreated controls. Co-treatment with TEMPOL, TEMPONE, TEMPO or MitoTEMPO resulted in a further increase in late apoptosis and necrosis with little effect on apoptotic cell death.

FIG. 35—Concentration-Response Plot Showing the Effects of TEMPO and MitoTEMPO on MAL-Induced PpIX Accumulation in A431 Cells: The Mitochondria-Targeted MitoTEMPO is Significantly More Potent at Increasing MAL-Induced PpIX than its Non-Targeted Parent Compound, TEMPO A431 cells were treated concurrently with MAL (1 mM) and TEMPO (50-5000 μM), MitoTEMPO (0.1-100 μM) or CP94 (0.1-100 μM) for 3 hours. Following treatment, PpIX accumulation was measured by fluorescence plate reader (excitation 410 nm, excitation 630 nm).

The effects of TEMPO and MitoTEMPO on MAL-induced PpIX accumulation were investigated. CP94, a well-known enhancer of PpIX accumulation, was used as a positive control and for comparison. The data presented in FIG. 35 show the measured increase in relative fluorescence of PpIX, compared to treatment with MAL (1 mM) alone.

The data show that each compound increased PpIX accumulation in A431 cells in a typical concentration-response manner. MitoTEMPO is significantly more potent than TEMPO at increasing MAL-induced PpIX accumulation, but less so than CP94. For example, at 50 μM TEMPO did not have any statistically significant effect (0.0±4.9%), whilst MitoTEMPO induced a 109.1±9.6% increase in PpIX accumulation ($p<0.001$ c.f. 50 μM TEMPO) and CP94 increased PpIX by 223.2±26.1% ($p=0.001$ c.f. 50 μM MitoTEMPO).

The peak response for TEMPO was obtained at 5 mM (138.1±10.5%) and a peak response for MitoTEMPO was obtained at 100 μM (126.0±11.8%), a 50-fold lower concentration. The peak response for CP94 was also obtained at 100 μM, but this was significantly higher than the response from MitoTEMPO (228.1±42.3% $p<0.001$).

FIG. 36—A431 Cell Death Induced by Photodynamic Cell Killing Following Treatment with MAL in the Absence and Presence of Different Concentrations of TEMPOL: TEMPOL Potentiates MAL-Induced Photodynamic Cell Killing in a Concentration-Dependent Manner A431 cells were treated with MAL (1 mM) in the absence and presence of TEMPOL (10, 100 and 1000 μM) for 3 hours, after which cells were irradiated for 5 minutes (630 nm, 25 J/cm$^2$) and then incubated for further 3 hours. Cell viability was assessed by annexin V-FITC and propidium iodide staining in conjunction with flow cytometry.

The mean cell death of the untreated control group was 13.4±1.5%.

The data in FIG. 36 show that treatment with MAL alone resulted in a significant increase in cell death (24.6±4.2%, $p<0.01$ c.f. control). Co-treatment of A431 cells with MAL and 10, 100 or 1000 μM TEMPOL lead to statistically significant increases in cell death (in a concentration-dependent manner) compared to MAL alone, with 40.5±4.1% ($p<0.001$), 48.5±7.4% ($p<0.001$) and 69.3±3.1% ($p<0.001$) cell death observed, respectively.

FIG. 37—Modes of A431 Cell Death Induced by Photodynamic Cell Killing Following Treatment with MAL in the Absence and Presence of Nitroxides: TEMPOL Potentiates MAL-Induced Photodynamic Cell Killing in a Concentration-Dependent Manner Through Promotion of Apoptotic and Necrotic Cell Death Annexin V-FITC and propidium iodide staining was used to assess the modes of cell death following irradiation of A431 cells treated with MAL (1 mM) in absence and presence of the nitroxides TEMPOL (1 mM), TEMPONE (1 mM), TEMPO (1 mM) and MitoTEMPO (50 μM). Results are set out in FIG. 37.

Photodynamic irradiation of A431 cells pre-treated with MAL (1 mM) resulted in an increase in all types of cell death compared to the untreated controls. Co-treatment with TEMPOL lead to an increase in apoptosis and late apoptosis, with smaller increases in necrosis also observed. These increases were dependent on the concentration of TEMPOL.

FIG. 38—Concentration-Response Plot Showing the Effects of TEMPOL, TEMPONE and TEMPO on MAL-Induced PpIX Accumulation in A431 Cells: TEMPOL, TEMPONE and TEMPO Increase MAL-Induced PpIX Accumulation in a Concentration-Dependent Manner A431 cells were treated concurrently with MAL (1 mM) and either TEMPOL, TEMPONE or TEMPO (10, 100 or 1000 μM) for 3 hours. Following treatment, PpIX accumulation was measured by fluorescence plate reader (excitation 410 nm, excitation 630 nm).

The effects of TEMPOL, TEMPONE and TEMPO on MAL-induced PpIX accumulation were investigated. The data in FIG. 38 are presented as a percentage of the MAL alone treatment (100±2.8).

PpIX accumulation was significantly increased by TEMPOL at 10, 100 and 1000 μM, with 109.0±2.7% ($p<0.01$ c.f. MAL alone), 141.2±4.2% ($p<0.001$) and 209.2±5.1% ($p<0.001$) PpIX accumulation, respectively.

At 10 uM, neither TEMPO (100.3±3.8%) nor TEMPONE (100.3±4.0%) had any effect on PpIX accumulation ($p>0.05$). Statistically significant increases were induced by TEMPO at 100 and 1000 μM, with 127.0±3.3% ($p<0.001$ c.f. MAL alone) and 159.2±4.1% ($p<0.001$ c.f. MAL alone) PpIX observed, respectively. TEMPONE had similar effects, with 123.8±2.5% and 160.2±3.2% PpIX at 100 and 1000 μM, respectively.

FIG. 39—the Effects of Nitroxides on Reactive Oxygen Species Generation During Photodynamic Irradiation of A431 Cells Pre-Treated with MAL: Nitroxides Increase Mitochondrial Oxidant Generation During MAL-Based Photodynamic Cell Killing A431 cells were treated concurrently with TEMPOL, TEMPONE, TEMPO (1 mM), MitoTEMPO or CP94 (50 μM) and MAL (1 mM) for 3 hours and MitoSOX (2.5 μM) for 1 hour, after which they were irradiated for 5 min (630 nm, 25 J/cm$^2$) and MitoSOX (mito-2-OH-E$^+$) fluorescence, indicative of mitochondrial oxidant production, was immediately analysed by flow cytometry. Results are set out in FIG. 39.

Mitochondria-targeted dihydroethidium was used to assess the production of reactive oxygen species (ROS) by PpIX photochemical reactions and to determine the effects of nitroxides on this process. All of the results are represented as a percentage of untreated cells (100.0±4.3%).

The fluorescence of the photoirradiated cells, which had been pre-treated with MAL alone, was 143.3±4.8% ($p<0.001$ c.f. untreated controls). Co-treatment of MAL with CP94 or MitoTEMPO (50 µM) resulted in a further increase in MitoSOX fluorescence to 198.4±7.7% ($p<0.001$, c.f. MAL alone) and 220.3±9.0% ($p<0.001$), respectively. Co-treatment of MAL with TEMPOL, TEMPONE and TEMPO (1 mM) also increased MitoSOX fluorescence to 253.3±6.3% ($p<0.001$, c.f. MAL alone), 226.4±6.8% ($p<0.001$) and 418.8±6.3% ($p<0.001$), respectively.

FIG. 40—the Effects of Different Concentrations of TEMPOL on Reactive Oxygen Species Generation During Photodynamic Irradiation of A431 Cells Pre-Treated with MAL
TEMPOL Increases Mitochondrial Oxidant Generation During MAL-Based Photodynamic Cell Killing in a Concentration-Dependent Manner A431 cells were treated concurrently with TEMPOL (10, 100 or 1000 µM) and MAL (1 mM) for 3 hours and MitoSOX (2.5 µM) for 1 hour, after which they were irradiated for 5 min (630 nm, 25 J/cm$^2$) and MitoSOX (mito-2-OH-E$^+$) fluorescence, indicative of mitochondrial oxidant production, was immediately analysed by flow cytometry. Results are set out in FIG. 40.

Mitochondria-targeted dihydroethidium was used to assess the production of reactive oxygen species (ROS) by PpIX photochemical reactions and to determine the effects of nitroxides on this process. All of the results are represented as a percentage of untreated cells (100.0±5.8%).

The fluorescence of the photoirradiated cells, which had been pre-treated with MAL alone, was 207.4±16.7% ($p<0.001$ c.f. untreated controls). Co-treatment of MAL with 10 µM TEMPOL had no statistically significant effect on MitoSOX fluorescence (99.4±5.44% $p>0.05$ c.f. MAL alone). Co-treatment of MAL with 100 and 1000 µM TEMPOL significantly increased MitoSOX fluorescence, compared to MAL alone, with 226.5±19.4% ($p<0.05$) and 316.8±1.6% ($p<0.001$) fluorescence, respectively.

The invention claimed is:

1. A combination comprising:
   (i) an inhibitor of the thioredoxin antioxidant system selected from the group consisting of auranofin, aurothiomalate, aurothiosulfate, aurothioglucose, DNCB and PX12; and
   (ii) a photosensitizer or photosensitizer precursor selected from the group consisting aminolaevulinic acid (ALA), methyl aminolaevulinate (MAL), hexyl aminolaevulinate (HAL), and a combination thereof;
   for use in photodynamic therapy.

2. The combination according to claim 1 wherein the inhibitor is auranofin.

3. The combination according to claim 1, wherein the inhibitor is DNCB.

4. The combination for use according to claim 1, wherein the inhibitor is PX12.

5. The combination for use according to claim 1, wherein the photosensitizer precursor is methyl aminolaevulinate (MAL).

6. A method of treating cancer, comprising administering to a patient in need thereof: a photodynamic therapy with a combination set forth in claim 1.

7. A method of treating a condition, comprising administering to a patient in need thereof: a photodynamic therapy with a combination set forth in claim 1, wherein said condition is selected from the group consisting of scleroderma, lichen sclerosus, psoriasis, warts, chronic wounds, acne, a microbial infection, a parasitic infestation, rheumatoid arthritis or leukaemia.

8. A method of purging bone marrow, comprising administering to a patient in need thereof: a photodynamic therapy with a combination set forth in claim 1.

* * * * *